(12) United States Patent
Wang et al.

(10) Patent No.: US 11,384,069 B2
(45) Date of Patent: Jul. 12, 2022

(54) DIPHENYLAMINOPYRIMIDINE COMPOUND FOR INHIBITING KINASE ACTIVITY

(71) Applicant: Shenzhen TargetRx, Inc., Guangdong (CN)

(72) Inventors: Yihan Wang, Guangdong (CN); Huanyin Li, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 0 days.

(21) Appl. No.: 16/492,994

(22) PCT Filed: Sep. 30, 2018

(86) PCT No.: PCT/CN2018/109043
§ 371 (c)(1),
(2) Date: Sep. 11, 2019

(87) PCT Pub. No.: WO2019/140953
PCT Pub. Date: Jul. 25, 2019

(65) Prior Publication Data
US 2020/0071303 A1    Mar. 5, 2020

(30) Foreign Application Priority Data

Jan. 16, 2018 (CN) .......................... 201810039319.3

(51) Int. Cl.

| | | |
|---|---|---|
| *C07D 403/12* | (2006.01) | |
| *C07D 239/48* | (2006.01) | |
| *A61P 17/06* | (2006.01) | |
| *A61P 27/02* | (2006.01) | |
| *A61P 25/16* | (2006.01) | |
| *A61P 25/28* | (2006.01) | |
| *A61P 29/00* | (2006.01) | |
| *A61P 19/08* | (2006.01) | |
| *A61P 35/00* | (2006.01) | |
| *A61P 35/02* | (2006.01) | |
| *A61P 1/16* | (2006.01) | |
| *A61P 31/12* | (2006.01) | |
| *A61P 3/10* | (2006.01) | |
| *A61P 21/04* | (2006.01) | |
| *A61P 37/06* | (2006.01) | |
| *A61P 7/02* | (2006.01) | |
| *A61P 9/00* | (2006.01) | |
| *A61P 9/10* | (2006.01) | |
| *A61P 11/06* | (2006.01) | |

(52) U.S. Cl.
CPC ........ *C07D 403/12* (2013.01); *C07B 2200/05* (2013.01)

(58) Field of Classification Search
CPC .......................... C07D 239/48; C07D 403/12; C07B 2200/05; A61P 9/10; A61P 9/00; A61P 25/28; A61P 21/04; A61P 35/00; A61P 35/02; A61P 3/10; A61P 17/06; A61P 25/16; A61P 27/02; A61P 31/12; A61P 37/06; A61P 29/00; A61P 7/02; A61P 11/06; A61P 1/16; A61P 19/08

See application file for complete search history.

(56) References Cited

U.S. PATENT DOCUMENTS

2017/0174713 A1    6/2017   Du et al.

FOREIGN PATENT DOCUMENTS

| JP | 2009-513703 A | 4/2009 |
|---|---|---|
| JP | 2013-541595 A | 11/2013 |
| WO | WO 2012/060847 A1 | 5/2012 |

(Continued)

OTHER PUBLICATIONS

Deuterium, 2021, https://en.wikipedia.org/wiki/Deuterium.*

(Continued)

*Primary Examiner* — Sun Jae Yoo
(74) *Attorney, Agent, or Firm* — Wolf, Greenfield & Sacks, P.C.

(57) ABSTRACT

Provided in the present invention are a pharmaceutical composition of a substituted diphenylaminopyrimidine compound and a use thereof, wherein the compound is the compound as shown in formula (I), or a pharmaceutically acceptable salt, prodrug, hydrate or solvate, crystal form, N-oxide and various diastereomers thereof. The compound of the present invention can be used for treating diseases that can be treated with the JAK2 kinase inhibitor.

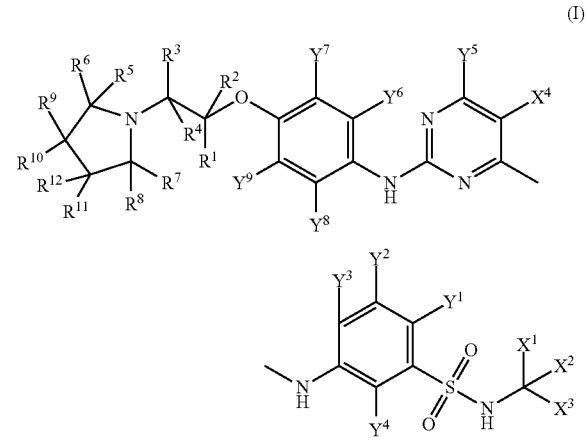

16 Claims, No Drawings

(56) References Cited

FOREIGN PATENT DOCUMENTS

| WO | WO 2017/059319 A2 | 4/2017 |
| WO | WO 2018/096525 A2 | 5/2018 |

OTHER PUBLICATIONS

RN 2227319-08-4, 2018, caplus an 2018:2227319-08-4.*
CancerPrevention, 2021, https://www.cancerresearchuk.org/about-cancer/causes-of-cancer/can-cancer-be-prevented-0.*
Ruxolitinib, 2021, https://hcp.jakafi.com/polycythemia-vera/p-vera-home?utm_source=google&utm_medium=cpc&utm_campaign=JAK-HCP_21_Healthcare-Industry_UB_PV_Treatment_Phrase_%3BS%3BPH%3BBR%3BHEM%3BHCP%3BTRE&utm_content=PV_Treatment_P&utm_term=polycythemia+vera+treatment&gclsrc=aw.ds&&gclid=Cj0KCQjw4eaJBhDMARIsANhrQ.*
Seif et al., 2020, Int ArchAllergy Immunol, 181, 467-475.*
Kvist-Hansen-et al., Dermatol Ther, 2020, 10, 29-42.*
Jiang et al., Application of deuteraticii in drug research. Qilu Pharmaceutical Affairs. 2010;29(11):682-4.
Qiao et al., Design, synthesis and bioactivities of 4-(3-sulfonylbenzene) amino-6-formylpyrrole [2,3-d] pyrimidine derivatives. J China Pharmaceutical University. 2017;48(5):554-62.
International Search Report and Written Opinion for PCT/CN2018/109043, dated Dec. 12, 2018.
Extended European Search Report for Application No. EP 18901461.6, dated Nov. 5, 2019.
Meanwell, Synopsis of some recent tactical application of bioisosteres in drug design. J Med Chem. 2011;54(8):2529-2591. doi:10.1021/jm1013693.
Qiao et al., Design, synthesis and bioactivities of 4-(3-sulfonylbenzene) amino-6-formylpyrrole[2,3-d ] pyrimidine derivatives. J China Pharmaceutical University. 2017;48(5):554-562.
Trelinski et al., JAK inhibitors: pharmacology and clinical activity in chronic myeloproliferative neoplasms. Curr Med Chem. 2013;20(9):1147-1161. doi:10.2174/0929867311320090004.
Japanese Office Action for Application No. 2020-539273, dated Oct. 5, 2021.
Author Unknown, Heavy Hydrogen. Chemistry Great Dictionary. Tokyo Kagaku Dojin. 1989: 1086-87.
JP 2020-539273, Oct. 5, 2021, Office Action and English translation thereof.

* cited by examiner

DIPHENYLAMINOPYRIMIDINE COMPOUND FOR INHIBITING KINASE ACTIVITY

CROSS REFERENCE TO RELATED APPLICATIONS

The present application is a national stage application of PCT/CN2018/109043 filed on Sep. 30, 2018, which claims the priority of Chinese Patent Application No. 201810039319.3 filed on Jan. 16, 2018. The Chinese Patent Application No. 201810039319.3 is incorporated herein by reference as part of the disclosure of the present application.

TECHNICAL FIELD

The present disclosure belongs to the pharmaceutical field, and in particular relates to a substituted diphenylamino pyrimidine compound, a composition comprising the same and the use thereof. More specifically, the present disclosure relates to certain deuterated N-(tert-butyl)-3-((5-methyl-2-((4-(2-(pyrrolidin-1-yl)ethoxy)phenyl)amino) pyrimidin-4-yl)amino)benzenesulfonamide. These deuterated compounds exhibit inhibition of JAK2 protein tyrosine kinase and are useful for the treatment of JAK2 kinase-mediated diseases. Moreover, these deuterated compounds have superior pharmacokinetic properties.

BACKGROUND OF THE PRESENT INVENTION

The JAK family of cellular protein tyrosinase includes four subtypes of kinase JAK1 to JAK3 and TYK2, which are highly homologous. They have seven homology domains (JH) from the carboxy terminus (C-terminus) to the amino terminus (N-terminus) and are usually divided into four functional domains. Among others, JH1 is the active kinase catalytic domain, and JH2 domain is a domain unique to the JAK family, known as the pseudokinase structural domain or the pseudokinase domain. Although it has no catalytic function, it plays an indispensable and key role in regulation through cooperation. SH2 domain consisting of JH3 and JH4 plays a role in stabilizing the kinase structure of JAK. The JH5 to JH7 moieties (FERM domain) interact directly with the intracellular structure of cytokine receptors and also interact with the JH1 domain.

Among others, JAK2 has a unique cytokine profile in the JAK family. In addition to being activated by the g-chain (gc) family of cytokine, it can also be activated by many other cytokines (for example, blood-related cytokines such as the bc family of cytokine, erythropoietin, and thrombopoietin). Its activity is essential for the process of hematopoiesis. Therefore, JAK2 can affect some basic functions of regulation erythropoietin (EPO) and granulocyte-macrophage colony-stimulating factor (GM-CSF), and is closely related to polycythemia vera (PV), anemia, essential thrombocythemia (ET) and other blood diseases. If it is seriously damaged, it is a fatal threat to an organism.

It has been demonstrated that the JAK pathway can be recruited in cell survival and proliferation. For example, in the case of cells that are positive in Philadelphia chromosomes that cause chronic myeloid leukemia (CML), there is evidence that the JAK2 pathway is recruited in constitutive activation. Thus, JAK2 inhibitors can be applied to CML, where it has been confirmed that the Philadelphia chromosome produces a hybrid Bcr-Abl, thereby keeping cells constitutively active.

More profoundly, in cases of resistant mutations produced by specific inhibitors of BCR-ABL, as in the case of the T315I gatekeeper mutation or any other mutation, it may be possible to use a JAK2 inhibitor targeting the BCR-ABL mutant (as in the case of BCR-ABL(T315I) mutation) of the JAK2 pathway. Thus JAK2 inhibitors may be used in the treatment of patients with resistance to known therapies where BCR-ABL is directly targeted, and drug resistance has now been demonstrated as the dominant (50%-90%) of all resistance in patients where existing therapies fail.

Accordingly, there is a need to develop compounds useful as inhibitors of kinases, particularly, JAK2 kinase, given the inadequate treatments available for the aforementioned diseases where the JAK2 signaling pathway is dysregulated, or recruited directly or indirectly.

Fedratinib (SAR-302503, TG-101348), developed by TargeGene, was acquired by Sanofi in 2010 and developed to the advanced clinical stage. The drug was later taken over by a startup, Impact Biopharmaceuticals, for continuation development. The company has now been acquired by Celgene. Fedratinib is a highly selective oral inhibitor of JAK2 protein kinase with the chemical name (N-(tert-butyl)-3-((5-methyl-2-((4-(2-(pyrrolidin-1-yl)ethoxy)phenyl) amino)pyrimidin-4-yl)amino)benzenesulfonamide. The clinical indications of Fedratinib are myelofibrosis (MF) and polycythemia vera (PV). Fedratinib showed excellent clinical benefit in the early clinical stage, but in 2013, Fedratinib was found to have severe neurological side effects.

Therefore, there remains a need in the art to develop compounds having selective inhibitory activity or better pharmacodynamics/pharmacokinetics for JAK2 kinase-mediated diseases useful as therapeutic agents. The present disclosure provides a novel JAK2 inhibitor which is obtained by deuteration modification of Fedratinib as a parent compound. The following benefits are achieved by the deuteration strategy: undesirable metabolites are reduced or eliminated; the half-life of the parent compound is increased; the number of doses required to achieve the desired effect is reduced; the amount of dose required to achieve the desired effect is reduced; the formation of active metabolites (if formed) is increased; the production of harmful metabolites in specific tissues is reduced; and drugs that are more effective and/or safe for multiple administrations (whether or not the multiple administrations are intended) are produced.

SUMMARY OF THE PRESENT INVENTION

In view of the above technical problems, disclosed herein are a novel deuterated diphenylpyrimidine compound, a composition containing the same and the use thereof. The deuterated diphenylpyrimidine compound has better activity of inhibiting JAK2 kinase and JAK2/V617F kinase, lower side effects, better pharmacodynamics/pharmacokinetic properties, and can be used to treat JAK2 kinase-mediated diseases.

In this regard, the present disclosure adopts the following technical solutions:

In the first aspect of the present disclosure, disclosed herein is a compound of Formula (I):

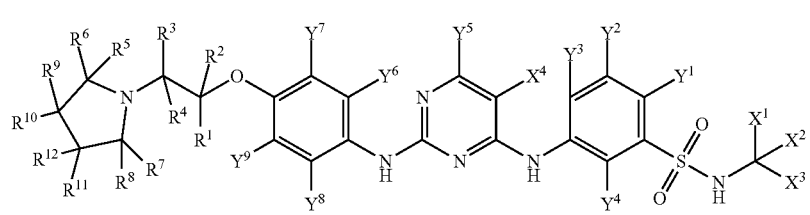

Formula (I)

wherein, $R^1$, $R^2$, $R^3$, $R^4$, $R^5$, $R^6$, $R^7$, $R^8$, $R^9$, $R^{10}$, $R^{11}$, $R^{12}$, $Y^1$, $Y^2$, $Y^3$, $Y^4$, $Y^5$, $Y^6$, $Y^7$, $Y^8$ and $Y^9$ are each independently selected from the group consisting of hydrogen and deuterium;

$X^1$, $X^2$, $X^3$, and $X^4$ are each independently selected from the group consisting of $CH_3$, $CD_3$, $CHD_2$, and $CH_2D$;

provided that if $X^1$, $X^2$, $X^3$, and $X^4$ are each $CH_3$, then at least one of $R^1$, $R^2$, $R^3$, $R^4$, $R^5$, $R^6$, $R^7$, $R^8$, $R^9$, $R^{10}$, $R^{11}$, $R^{12}$, $Y^1$, $Y^2$, $Y^3$, $Y^4$, $Y^5$, $Y^6$, $Y^7$, $Y^8$, and $Y^9$ is deuterium.

In another aspect, provided herein is a pharmaceutical composition comprising the compound disclosed herein and pharmaceutically acceptable excipients. In a particular embodiment, the compound disclosed herein is provided in the pharmaceutical composition in an effective amount. In a particular embodiment, the compound disclosed herein is provided in a therapeutically effective amount. In a particular embodiment, the compound disclosed herein is provided in a prophylactically effective amount.

In another aspect, provided herein is a method of preparing the pharmaceutical composition as described above, comprising the step of mixing pharmaceutically acceptable excipients with the compound disclosed herein to form the pharmaceutical composition.

In another aspect, the present disclosure is also directed to a method of treating a disease mediated at least in part by JAK2, comprising administering to a subject in need thereof a therapeutically effective amount of the compound disclosed herein. In a particular embodiment, provided herein is use of the compound disclosed herein in the manufacture of a medicament for the treatment of a disease mediated by JAK2 useful for a subject in need thereof. In a particular embodiment, provided herein is use of the compound disclosed herein in the manufacture of a medicament for the treatment of a disease mediated by JAK2/V617F useful for a subject in need thereof. In a particular embodiment, the compound is administered orally, subcutaneously, intravenously or intramuscularly. In a particular embodiment, the compound is administered for a long term. In a particular embodiment, the JAK2 mediated disease is selected from the group consisting of a proliferative disorder of bone marrow tissue, polycythemia vera, idiopathic thrombocytosis, myelofibrosis, any other disorder associated with bone marrow, proliferative diabetic retinopathy, cancer, eye disease, inflammation, psoriasis, any disease associated with angiogenesis and viral infection.

Other objectives and advantages of the present disclosure will be apparent to those skilled in the art from the following embodiments, examples and claims.

DETAILED DESCRIPTION OF THE PREFERRED EMBODIMENTS

Terms and Definitions

As used herein, unless otherwise specified, "deuterated" means that one or more hydrogens in a compound or group are replaced by deuterium; "deuterated" may be monosubstituted, disubstituted, polysubstituted or fully substituted with deuteriums. The term "one or more deuterated" is used interchangeably with "deuterated one or more times".

As used herein, unless otherwise specified, "non-deuterated compound" means a compound wherein the content of the deuterium atom is not higher than the natural content of the deuterium isotope (0.015%).

Also disclosed herein are isotopically labeled compounds to the extent of the original compounds disclosed herein. Examples of isotopes that can be listed in compounds disclosed herein include hydrogen, carbon, nitrogen, oxygen, phosphorus, sulfur, fluorine, and chlorine isotopes, such as $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds disclosed herein, or enantiomers, diastereoisomers, isomers, or pharmaceutically acceptable salts or solvates thereof, in which the isotopes as described above or other isotope atoms are contained, are within the scope disclosed herein. Certain isotopically labeled compounds disclosed herein, such as the radioisotopes of $^3H$ and $^{14}C$, are also among them and are useful in the tissue distribution experiments of drugs and substrates. Tritium, i.e., $^3H$, and carbon-14, i.e., $^{14}C$, are easier to be prepared and detected and are the first choice for isotopes. Isotopically-labeled compounds can be prepared using the schemes shown in the Examples by conventional methods by replacing the non-isotopic reagents with readily available isotopically labeled reagents.

Compounds described herein can comprise one or more asymmetric centers, and thus can exist in various "stereoisomeric" forms, e.g., enantiomers and/or diastereomers. For example, the compounds described herein can be in the form of an individual enantiomer, diastereomer or geometric isomer (such as cis- and trans-isomer), or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric synthesis.

As used herein, the term "compound disclosed herein" refers to a compound of Formula (I). The term also encompasses a pharmaceutically acceptable salt, a prodrug, a hydrate or a solvate, a N-oxide, a crystal form, a stereoisomer, an isotopic variation or various diastereoisomeric forms of the compound of Formula (I).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19.

Pharmaceutically acceptable salts of the compounds of the present disclosure include those derived from suitable inorganic and organic acids and inorganic and organic bases. Examples of pharmaceutically acceptable, nontoxic acid addition salts are salts of inorganic acids such as hydrochloric acid, hydrobromic acid, phosphoric acid, sulfuric acid and perchloric acid or salts of organic acids such as acetic acid, oxalic acid, maleic acid, tartaric acid, citric acid, succinic acid or malonic acid. Also included herein is the salt formed by using the conventional methods in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to a complex in which a compound disclosed herein coordinates with a solvent molecule in a particular ratio. "Hydrate" refers to a complex formed by coordination of a compound disclosed herein with water.

The term "prodrug" includes a class of compounds which may themselves be biologically active or inactive, and when taken by a suitable method, are converted into a compound of formula (I), or a salt or a solution of a compound of formula (I) by metabolism or chemical reaction in the human body. The prodrug includes, but is not limited to, the compounds in which an amino acid residue or a polypeptide chain consisting of one or more (e.g., 2, 3 or 4) amino acid residues is covalently linked by an amide or ester linkage on the free amino, hydroxyl or carboxyl group of the compound disclosed herein. The amino acid residue includes, but is not limited to, not only 20 natural amino acids usually represented by 3 letter symbols, but also 4-hydroxyproline, hydroxyl lysine, Demosine, isodemosine, 3-methylhistidine, norvaline, ornithine and methionine sulfone. Other types of prodrugs are also included. For example, a free carboxyl group can be derivatized as an amide or an alkyl ester. As described in Advanced Drug Delivery Reviews 1996, 19, 115, free hydroxyl groups are derivatized by the use of groups including, but not limited to, hemisuccinates, phosphates, dimethylaminoacetates, and phosphoryloxymethoxy carbonyl groups. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphoramides. All of these other moieties may incorporate groups including but not limited to ether, amine and carboxylic acid functionalities.

The term "crystalline form" refers to a different manner in which the molecules of a chemical drug are arranged, and is generally expressed as the form in which the pharmaceutical material is present in a solid state. One drug may exist in a plurality of crystalline forms. Different crystalline forms of the same drug may have different dissolution and absorption in the body, thereby affecting the dissolution and release of the formulation.

As used herein, the term "subject" includes, but is not limited to, humans (i.e., a male or female of any age group, e.g., a pediatric subject (e.g, infant, child, adolescent) or adult subject (e.g., young adult, middle-aged adult or elderly adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain other embodiments, the subject is a non-human animal.

"Disease," "disorder," and "condition" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound disclosed herein may vary depending on such factors as the desired biological endpoint, the pharmacokinetics of the compound, the disease being treated, the mode of administration, and the age, health, and condition of the subject. An effective amount encompasses therapeutically and prophylactically effective amount.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

"Combination" and related terms mean the simultaneous or sequential administration of a compound of the present disclosure. For example, a compound disclosed herein may be administered simultaneously or sequentially with another therapeutic agent in separate unit dosage forms, or together with another therapeutic agent in a single unit dosage form.

Specific Embodiments of the Present Invention

Compound

Provided herein is a compound of Formula (I), or a pharmaceutically acceptable salt, a prodrug, a hydrate or a solvate, a crystalline form, a N-oxide and various diastereoisomers thereof:

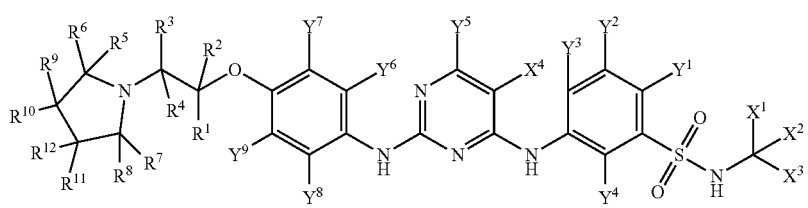

Formula (I)

wherein,
$R^1$, $R^2$, $R^3$, $R^4$, $R^5$, $R^6$, $R^7$, $R^8$, $R^9$, $R^{10}$, $R^{11}$, $R^{12}$, $Y^1$, $Y^2$, $Y^3$, $Y^4$, $Y^5$, $Y^6$, $Y^7$, $Y^8$ and $Y^9$ are each independently selected from the group consisting of hydrogen and deuterium;

$X^1$, $X^2$, $X^3$, and $X^4$ are each independently selected from the group consisting of $CH_3$, $CD_3$, $CHD_2$, and $CH_2D$;

provided that if $X^1$, $X^2$, $X^3$, and $X^4$ are each $CH_3$, then at least one of $R^1$, $R^2$, $R^3$, $R^4$, $R^5$, $R^6$, $R^7$, $R^8$, $R^9$, $R^{10}$, $R^{11}$, $R^{12}$, $Y^1$, $Y^2$, $Y^3$, $Y^4$, $Y^5$, $Y^6$, $Y^7$, $Y^8$ and $Y^9$ is deuterium;

As a preferred embodiment disclosed herein, the compound of Formula (I) has at least one deuterium atom, more preferably has one deuterium atom, more preferably two deuterium atoms, more preferably three deuterium atoms, more preferably four deuterium atoms, more preferably five deuterium atoms, more preferably six deuterium atoms, more preferably seven deuterium atoms, more preferably eight deuterium atoms, more preferably nine deuterium atoms, more preferably ten deuterium atoms, more preferably eleven deuterium atoms, more preferably twelve deuterium atoms, more preferably thirteen deuterium atoms, and more preferably fourteen deuterium atoms.

As a preferred embodiment disclosed herein, the content of deuterium isotope in the deuterated position is at least higher than the natural content of deuterium isotope (0.015%), preferably more than 30%, more preferably more than 50%, more preferably more than 75%, more preferably more than 95%, and more preferably more than 99%.

Specifically, the content of the deuterium isotope in each deuterated position of $R^1$, $R^2$, $R^3$, $R^4$, $R^5$, $R^6$, $R^7$, $R^8$, $R^9$, $R^{10}$, $R^{11}$, $R^{12}$, $Y^1$, $Y^2$, $Y^3$, $Y^4$, $Y^5$, $Y^6$, $Y^7$, $Y^8$, $Y^9$, $X^1$, $X^2$, $X^3$, and $X^4$ in the present disclosure is at least 5%, preferably more than 10%, more preferably more than 15%, more preferably more than 20%, more preferably more than 25%, more preferably more than 30%, more preferably more than 35%, more preferably more than 40%, more preferably more than 45%, more preferably more than 50%, more preferably more than 55%, more preferably more than 60%, more preferably more than 65%, more preferably more than 70%, more preferably more than 75%, more preferably more than 80%, more preferably more than 85%, more preferably more than 90%, more preferably more than 95%, and more preferably more than 99%.

In another particular embodiment, in $R^1$, $R^2$, $R^3$, $R^4$, $R^5$, $R^6$, $R^7$, $R^8$, $R^9$, $R^{10}$, $R^{11}$, $R^{12}$, $Y^1$, $Y^2$, $Y^3$, $Y^4$, $Y^5$, $Y^6$, $Y^7$, $Y^8$, $Y^9$, $X^1$, $X^2$, $X^3$, and $X^4$ in the compound of Formula (I), at least one, more preferably two, more preferably three, more preferably four, more preferably five, more preferably six, more preferably seven, more preferably eight, more preferably nine, more preferably ten, more preferably eleven, more preferably twelve, more preferably thirteen, more preferably fourteen, more preferably fifteen, more preferably sixteen, more preferably seventeen, more preferably eighteen, more preferably nineteen, more preferably twenty, more preferably twenty-one, more preferably twenty-two, more preferably twenty-three, more preferably twenty-four, more preferably twenty-five, more preferably twenty-six, more preferably twenty-seven, more preferably twenty-eight, more preferably twenty-nine, more preferably thirty, more preferably thirty-one, more preferably thirty-two, and more preferably thirty-three of contain deuterium. Specifically, the compound of Formula (I) contains at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, or thirty-three deuterium atoms.

In one embodiment of general formula (I), $R^1$, $R^2$, $R^3$, $R^4$, $R^5$, $R^6$, $R^7$, $R^8$, $R^9$, $R^{10}$, $R^{11}$, and $R^{12}$ are each independently selected from the group consisting of hydrogen and deuterium.

In another preferred embodiment, $R^1$ and $R^2$ are deuterium.

In another preferred embodiment, $R^3$ and $R^4$ are deuterium.

In another preferred embodiment, $R^1$, $R^2$, $R^3$, and $R^4$ are deuterium.

In another preferred embodiment, $R^5$, $R^6$, $R^7$, and $R^8$ are deuterium.

In another preferred embodiment, $R^9$, $R^{10}$, $R^{11}$, and $R^{12}$ are deuterium.

In another preferred embodiment, $R^5$, $R^6$, $R^7$, $R^8$, $R^9$, $R^{10}$, $R^{11}$, and $R^{12}$ are deuterium.

In one embodiment of general formula (I), $X^1$, $X^2$, $X^3$, and $X^4$ are each independently selected from the group consisting of $CH_3$, $CD_3$, $CHD_2$ and $CH_2D$.

In another preferred embodiment, $X^1$ is $CD_3$.
In another preferred embodiment, $X^2$ is $CD_3$.
In another preferred embodiment, $X^3$ is $CD_3$.
In another preferred embodiment, $X^4$ is $CD_3$.

In another preferred embodiment, $X^1$ and $X^2$ are both $CD_3$.

In another preferred embodiment, $X^1$, $X^2$, and $X^3$ are all $CD_3$.

In one embodiment of general formula (I), $Y^1$, $Y^2$, $Y^3$, $Y^4$, $Y^5$, $Y^6$, $Y^7$, $Y^8$ and $Y^9$ are each independently selected from the group consisting of hydrogen and deuterium.

In another preferred embodiment, $Y^5$ is deuterium.

One embodiment disclosed herein provides a compound of general formula (II):

Formula (II)

wherein,
$R^1$, $R^2$, $R^3$, $R^4$, $R^5$, $R^6$, $R^7$, $R^8$, $R^9$, $R^{10}$, $R^{11}$, $R^{12}$, $Y^5$, $X^1$, $X^2$, $X^3$, and $X^4$ are as defined above;
or a pharmaceutically acceptable salt, a prodrug, a hydrate or a solvate, a crystalline form, a N-oxide and various diastereoisomers thereof.

In one embodiment of general formula (II), $R^1$, and $R^2$ are deuterium, $R^3$, $R^4$, $R^5$, $R^6$, $R^7$, $R^8$, $R^9$, $R^{10}$, $R^{11}$, $R^{12}$, and $Y^5$ are each independently selected from the group consisting of hydrogen and deuterium, and $X^1$, $X^2$, $X^3$ and $X^4$ are each independently selected from the group consisting of $CH_3$, $CD_3$, $CHD_2$, and $CH_2D$.

In another preferred embodiment, $R^1$, and $R^2$ are deuterium, $R^3$, $R^4$, $R^5$, $R^6$, $R^7$, $R^8$, $R^9$, $R^{10}$, $R^{11}$, $R^{12}$, and $Y^5$ are each independently selected from the group consisting of hydrogen and deuterium, and $X^1$, $X^2$, $X^3$, and $X^4$ are each independently selected from the group consisting of $CH_3$ and $CD_3$.

In another preferred embodiment, $R^1$, $R^2$, $R^3$, and $R^4$ are deuterium, $R^5$, $R^6$, $R^7$, $R^8$, $R^9$, $R^{10}$, $R^{11}$, $R^{12}$, and $Y^5$ are each independently selected from the group consisting of hydrogen and deuterium, $X^1$, $X^2$, $X^3$, and $X^4$ are each independently selected from the group consisting of $CH_3$ and $CD_3$.

In one embodiment of general formula (II), $Y^5$ is deuterium, $R^1$, $R^2$, $R^3$, $R^4$, $R^5$, $R^6$, $R^7$, $R^8$, $R^9$, $R^{10}$, $R^{11}$, and $R^{12}$ are each independently selected from the group consisting of hydrogen and deuterium, and $X^1$, $X^2$, $X^3$ and $X^4$ are each independently selected from the group consisting of $CH_3$, $CD_3$, $CHD_2$, and $CH_2D$.

In another preferred embodiment, $Y^5$ is deuterium, $R^1$, $R^2$, $R^3$, $R^4$, $R^5$, $R^6$, $R^7$, $R^8$, $R^9$, $R^{10}$, $R^{11}$, and $R^{12}$ are each independently selected from the group consisting of hydrogen and deuterium, and $X^1$, $X^2$, $X^3$, and $X^4$ are each independently selected from the group consisting of $CH_3$ and $CD_3$.

In one embodiment of general formula (II), $Y^5$ is deuterium, $X^4$ is $CD_3$, $R^1$, $R^2$, $R^3$, $R^4$, $R^5$, $R^6$, $R^7$, $R^8$, $R^9$, $R^{10}$, $R^{11}$, and $R^{12}$ are each independently selected from the group consisting of hydrogen and deuterium, and $X^1$, $X^2$, and $X^3$ are each independently selected from the group consisting of $CH_3$, $CD_3$, $CHD_2$, and $CH_2D$.

In another preferred embodiment, $Y^5$ is deuterium, $X^4$ is $CD_3$, $R^1$, $R^2$, $R^3$, $R^4$, $R^5$, $R^6$, $R^7$, $R^8$, $R^9$, $R^{10}$, $R^{11}$, and $R^{12}$ are each independently selected from the group consisting of hydrogen and deuterium, and $X^1$, $X^2$ and $X^3$ are each independently selected from the group consisting of $CH_3$ and $CD_3$.

In one embodiment of general formula (II), $X^4$ is $CD_3$, $R^1$, $R^2$, $R^3$, $R^4$, $R^5$, $R^6$, $R^7$, $R^8$, $R^9$, $R^{10}$, $R^{11}$, $R^{12}$, and $Y^5$ are each independently selected from the group consisting of hydrogen and deuterium, and $X^1$, $X^2$ and $X^3$ are each independently selected from the group consisting of $CH_3$, $CD_3$, $CHD_2$, and $CH_2D$.

In another preferred embodiment, $X^4$ is $CD_3$, $R^1$, $R^2$, $R^3$, $R^4$, $R^5$, $R^6$, $R^7$, $R^8$, $R^9$, $R^{10}$, $R^{11}$, $R^{12}$, and $Y^5$ are each independently selected from the group consisting of hydrogen and deuterium, and $X^1$, $X^2$ and $X^3$ are each independently selected from the group consisting of $CH_3$ and $CD_3$.

In one embodiment of general formula (II), $X^1$ is $CD_3$, $R^1$, $R^2$, $R^3$, $R^4$, $R^5$, $R^6$, $R^7$, $R^8$, $R^9$, $R^{10}$, $R^{11}$, $R^{12}$, and $Y^5$ are each independently selected from the group consisting of hydrogen and deuterium, and $X^2$, $X^3$ and $X^4$ are each independently selected from the group consisting of $CH_3$, $CD_3$, $CHD_2$, and $CH_2D$.

In another preferred embodiment, $X^1$ is $CD_3$, $R^1$, $R^2$, $R^3$, $R^4$, $R^5$, $R^6$, $R^7$, $R^8$, $R^9$, $R^{10}$, $R^{11}$, $R^{12}$, and $Y^5$ are each independently selected from the group consisting of hydrogen and deuterium, $X^2$, $X^3$ and $X^4$ are each independently selected from the group consisting of $CH_3$ and $CD_3$.

In one embodiment of general formula (II), $X^1$ and $X^3$ are $CD_3$, $R^1$, $R^2$, $R^3$, $R^4$, $R^5$, $R^6$, $R^7$, $R^8$, $R^9$, $R^{10}$, $R^{11}$, $R^{12}$, and $Y^5$ are each independently selected from the group consisting of hydrogen and deuterium, and $X^2$ and $X^4$ are each independently selected from the group consisting of $CH_3$, $CD_3$, $CHD_2$, and $CH_2D$.

In another preferred embodiment, $X^1$ and $X^3$ are $CD_3$, $R^1$, $R^2$, $R^3$, $R^4$, $R^5$, $R^6$, $R^7$, $R^8$, $R^9$, $R^{10}$, $R^{11}$, $R^{12}$, and $Y^5$ are each independently selected from the group consisting of hydrogen and deuterium, and $X^3$ and $X^4$ are each independently selected from the group consisting of $CH_3$ and $CD_3$.

In one embodiment of general formula (II), $X^1$, $X^2$, and $X^3$ are $CD_3$, $R^1$, $R^2$, $R^3$, $R^4$, $R^5$, $R^6$, $R^7$, $R^8$, $R^9$, $R^{10}$, $R^1$, $R^{12}$, and $Y^5$ are each independently selected from the group consisting of hydrogen and deuterium, and $X^4$ is selected from the group consisting of $CH_3$, $CD_3$, $CHD_2$, and $CH_2D$.

In another preferred embodiment, $X^1$, $X^2$, and $X^3$ are $CD_3$, $R^1$, $R^2$, $R^3$, $R^4$, $R^5$, $R^6$, $R^7$, $R^8$, $R^9$, $R^{10}$, $R^{11}$, $R^{12}$, and $Y^5$ are each independently selected from the group consisting of hydrogen and deuterium, and $X^4$ is selected from the group consisting of $CH_3$ and $CD_3$.

In one embodiment of general formula (II), $R^5$, $R^6$, $R^7$ and $R^8$ are deuterium, $R^1$, $R^2$, $R^3$, $R^4$, $R^9$, $R^{10}$, $R^{11}$, $R^{12}$, and $Y^5$ are each independently selected from the group consisting of hydrogen and deuterium, and $X^1$, $X^2$, $X^3$ and $X^4$ are each independently selected from the group consisting of $CH_3$, $CD_3$, $CHD_2$, and $CH_2D$.

In another preferred embodiment, $R^5$, $R^6$, $R^7$ and $R^8$ are deuterium, $R^1$, $R^2$, $R^3$, $R^4$, $R^9$, $R^{10}$, $R^{11}$, $R^{12}$, and $Y^5$ are each independently selected from the group consisting of hydrogen and deuterium, and $X^1$, $X^2$, $X^3$, and $X^4$ are each independently selected from the group consisting of $CH_3$ and $CD_3$.

In one embodiment of general formula (II), $R^9$, $R^{10}$, $R^{11}$, and $R^{12}$ are deuterium, $R^1$, $R^2$, $R^3$, $R^4$, $R^5$, $R^6$, $R^7$, $R^8$ or $Y^5$ are each independently selected from the group consisting of hydrogen and deuterium, and $X^1$, $X^2$, $X^3$ and $X^4$ are each independently selected from the group consisting of $CH_3$, $CD_3$, $CHD_2$, and $CH_2D$.

In another preferred embodiment, $R^9$, $R^{10}$, $R^{11}$, and $R^{12}$ are deuterium, $R^1$, $R^2$, $R^3$, $R^4$, $R^5$, $R^6$, $R^7$, $R^8$ or $Y^5$ are each independently selected from the group consisting of hydrogen and deuterium, and $X^1$, $X^2$, $X^3$ and $X^4$ are each independently selected from the group consisting of $CH_3$ and $CD_3$.

In one embodiment of general formula (II), $R^5$, $R^6$, $R^7$, $R^8$, $R^9$, $R^{10}$, $R^{11}$, and $R^{12}$ are deuterium, $R^1$, $R^2$, $R^3$, $R^4$, or $Y^5$ are each independently selected from the group consisting of hydrogen and deuterium, and $X^1$, $X^2$, $X^3$ and $X^4$ are each independently selected from the group consisting of $CH_3$, $CD_3$, $CHD_2$, and $CH_2D$.

In another preferred embodiment, $R^5$, $R^6$, $R^7$, $R^8$, $R^9$, $R^{10}$, $R^{11}$, and $R^{12}$ are deuterium, $R^1$, $R^2$, $R^3$, $R^4$, and $Y^5$ are each independently selected from the group consisting of hydrogen and deuterium, and $X^1$, $X^2$, $X^3$, and $X^4$ are each independently selected from the group consisting of $CH_3$ and $CD_3$.

In a preferred embodiment disclosed herein, the compound is selected from the group consisting of the following compounds or pharmaceutically acceptable salts thereof:

Formula (1)

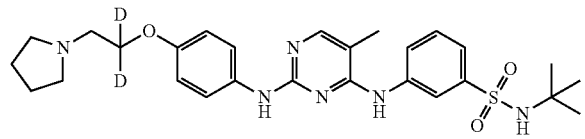

Formula (2)

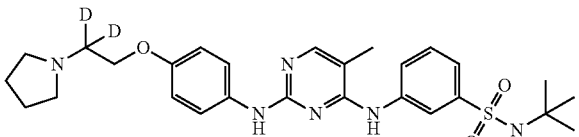

Formula (3)

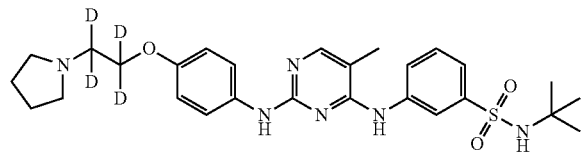

Formula (4)

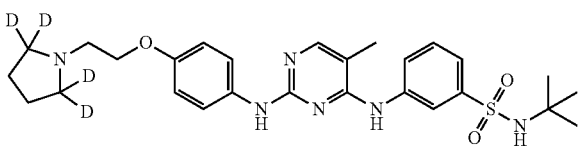

Formula (5)

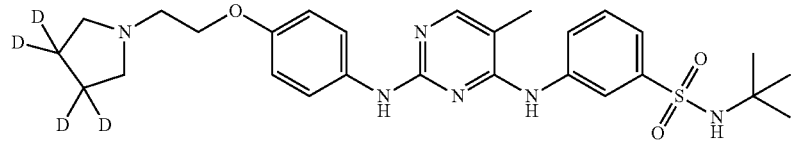

Formula (6)

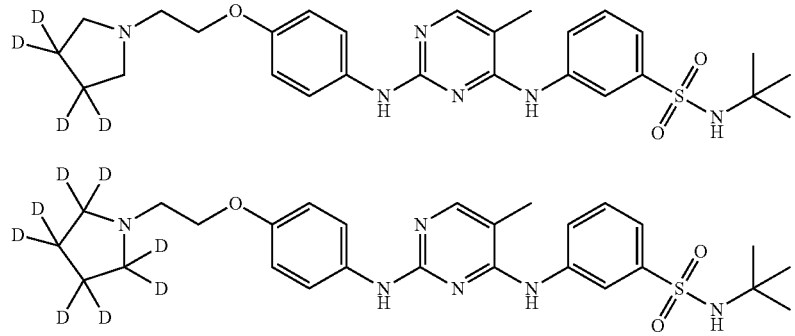

Formula (7)

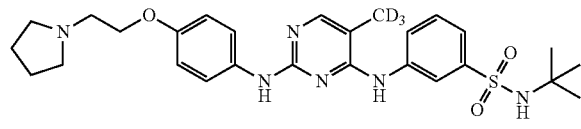

Formula (8)

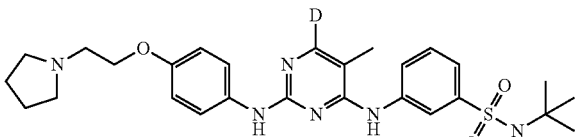

Formula (9)

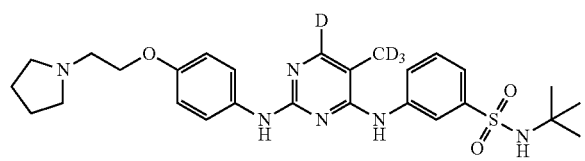

Formula (10)

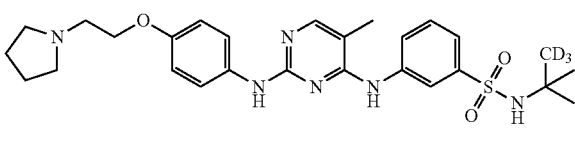

Formula (11)

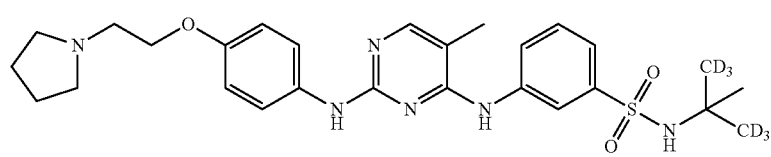

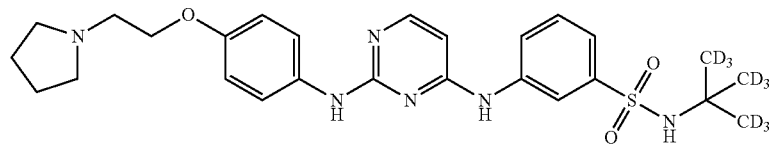
Formula (12)
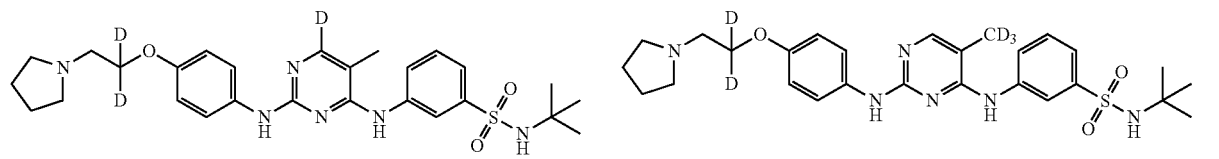
Formula (13)
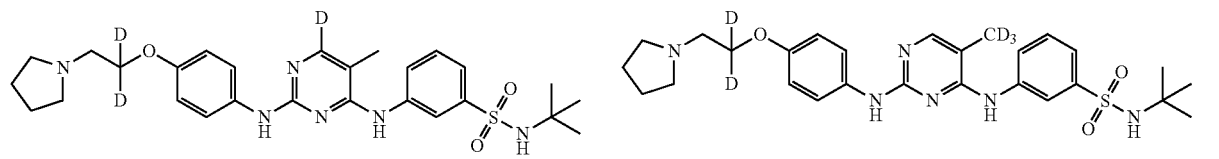
Formula (14)
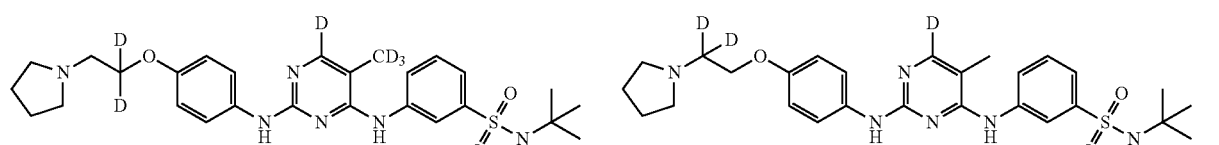
Formula (15)
Formula (16)
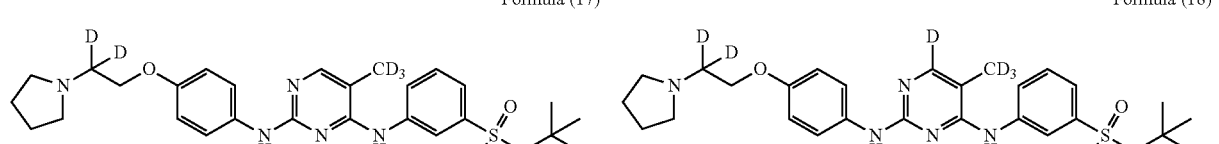
Formula (17)
Formula (18)
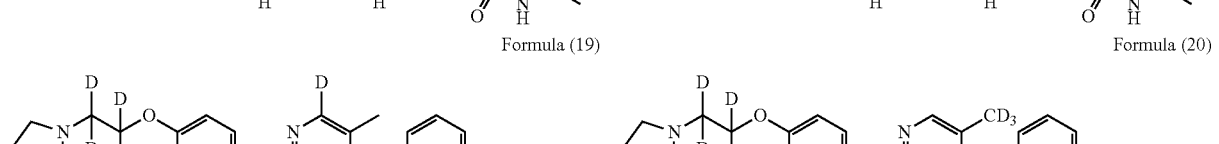
Formula (19)
Formula (20)
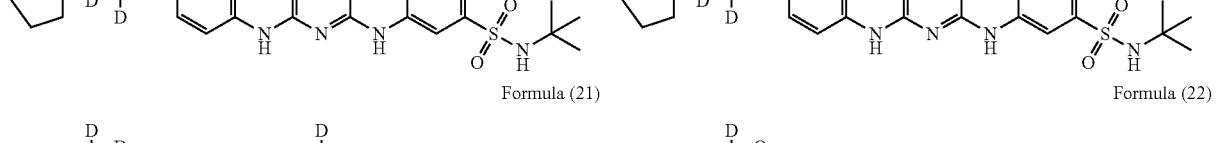
Formula (21)
Formula (22)
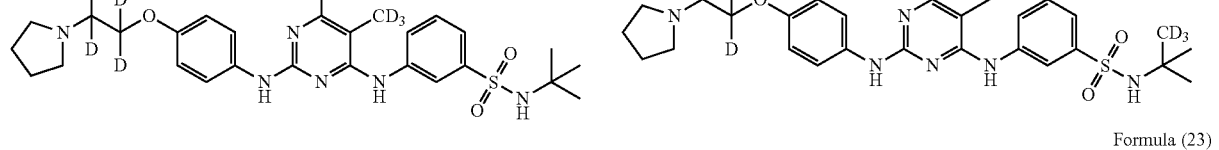
Formula (23)
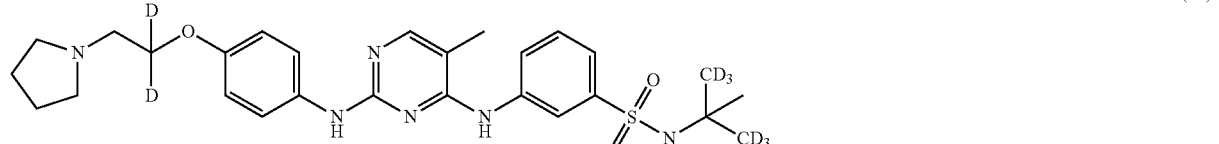
Formula (24)
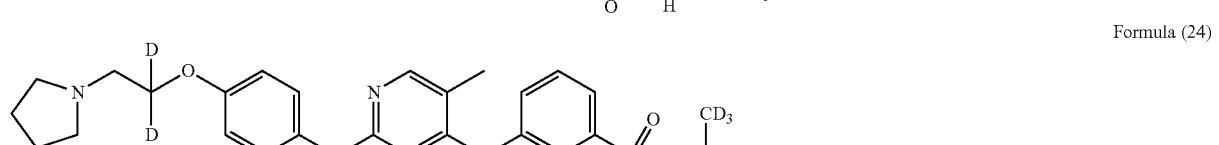
Formula (25)
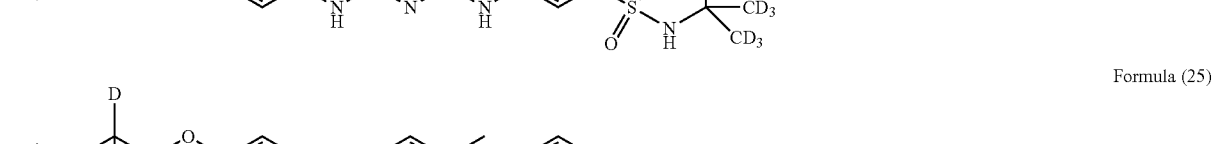
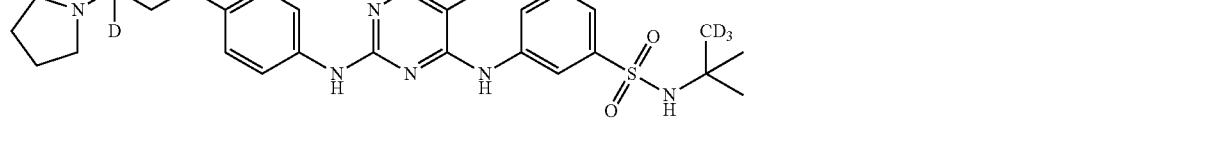

-continued
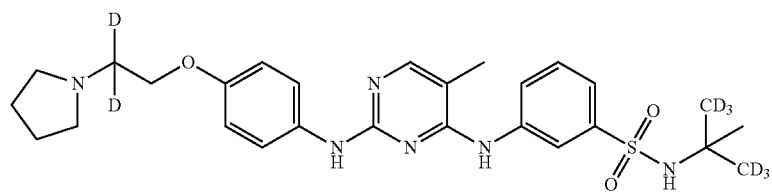
Formula (26)
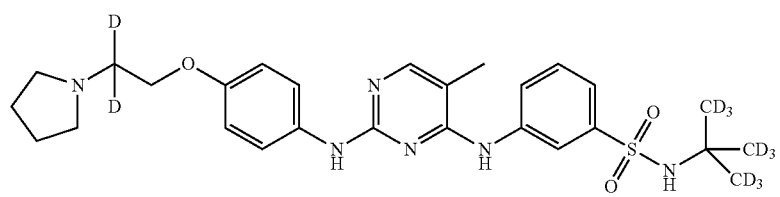
Formula (27)
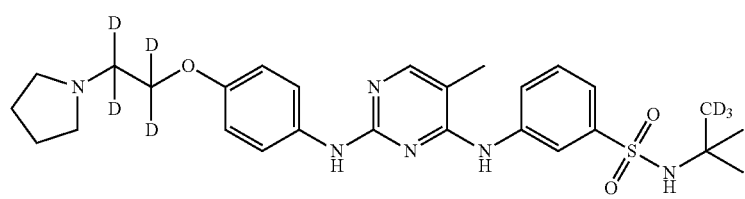
Formula (28)
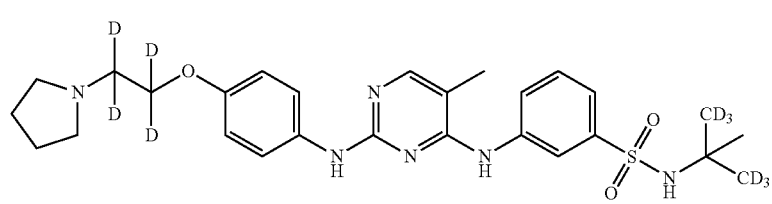
Formula (29)
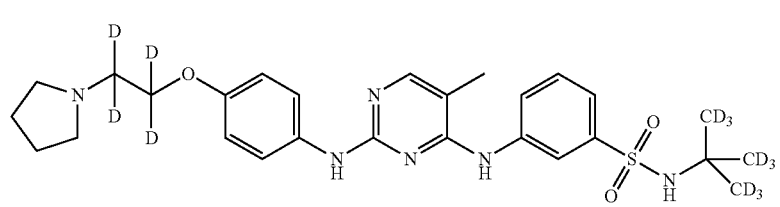
Formula (30)
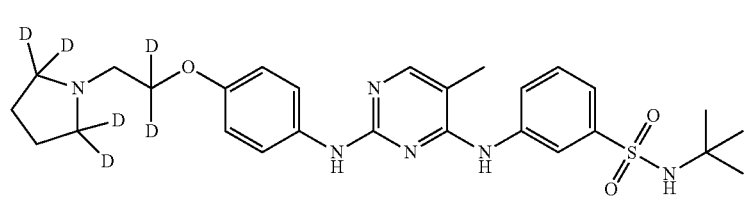
Formula (31)
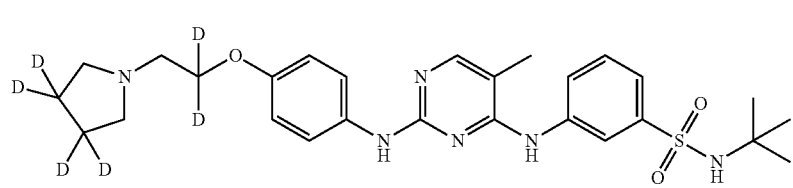
Formula (32)
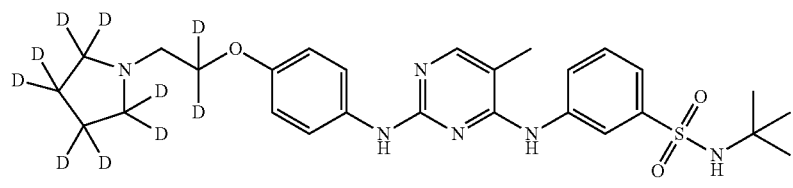
Formula (33)

-continued
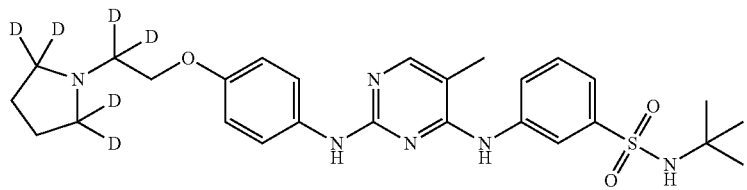
Formula (34)
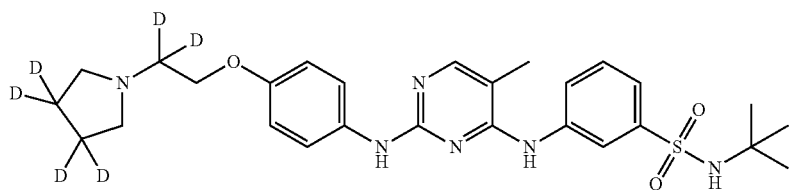
Formula (35)
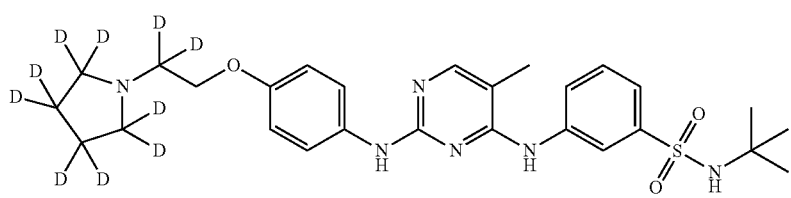
Formula (36)
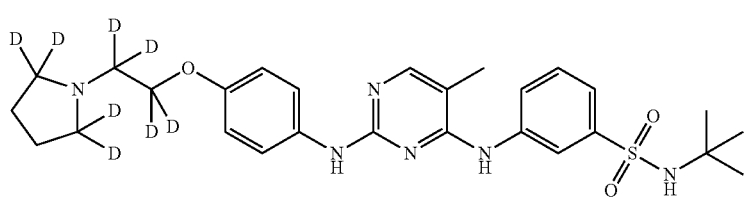
Formula (37)
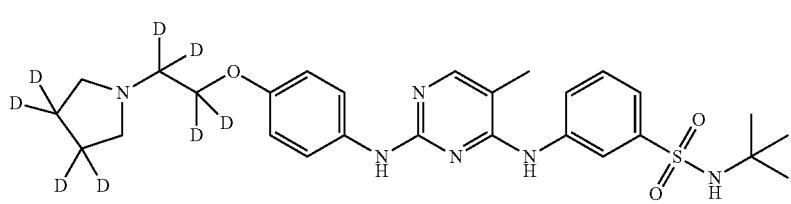
Formula (38)
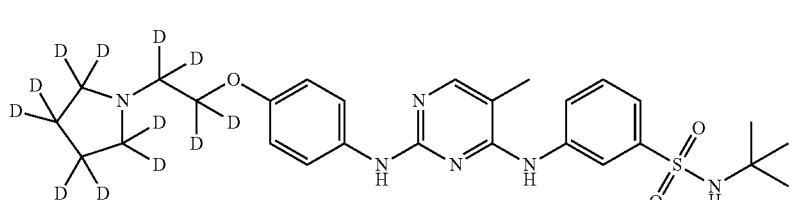
Formula (39)
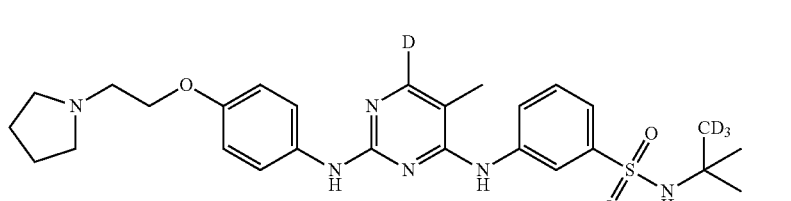
Formula (40)
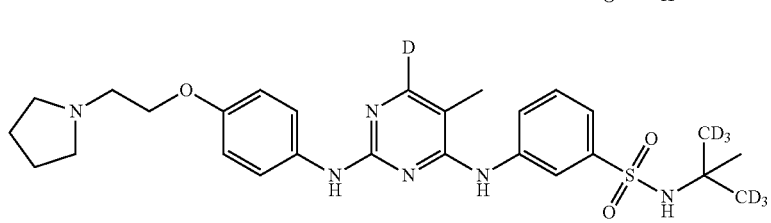
Formula (41)

-continued
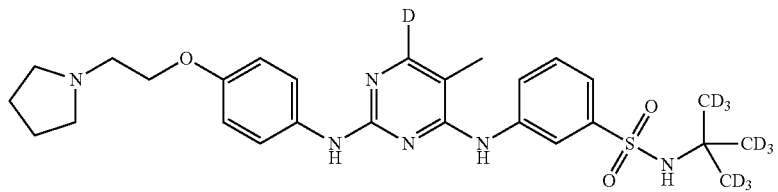
Formula (42)
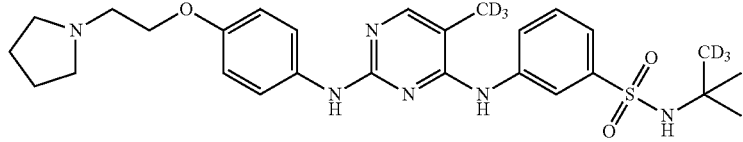
Formula (43)
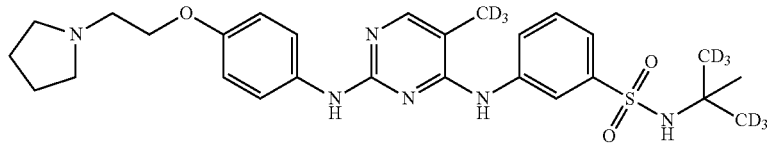
Formula (44)
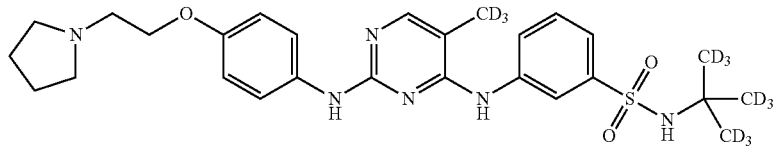
Formula (45)
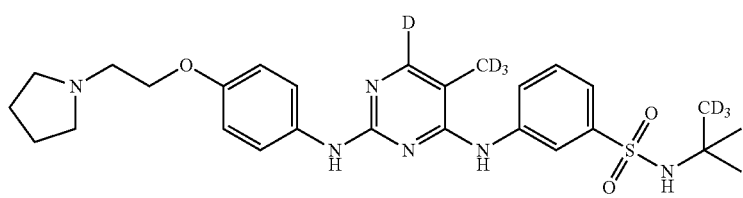
Formula (46)
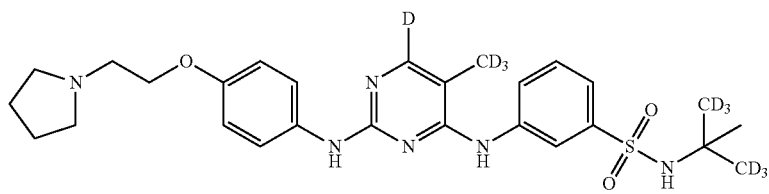
Formula (47)
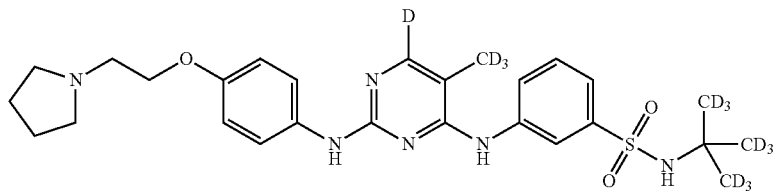
Formula (48)
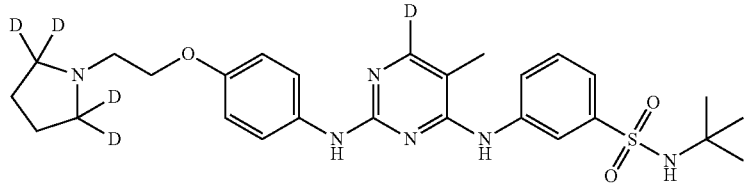
Formula (49)

-continued
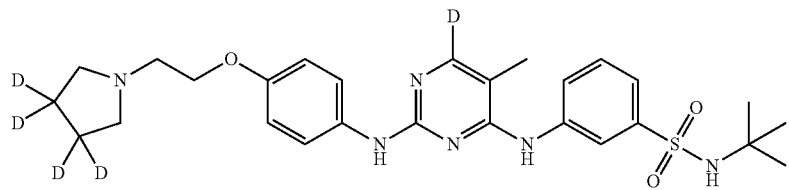
Formula (50)
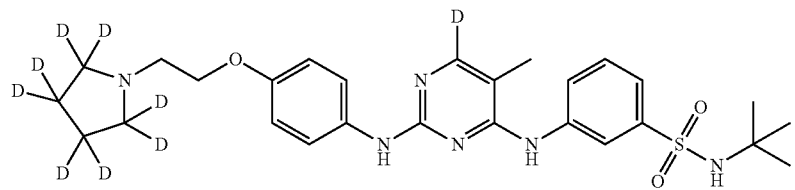
Formula (51)
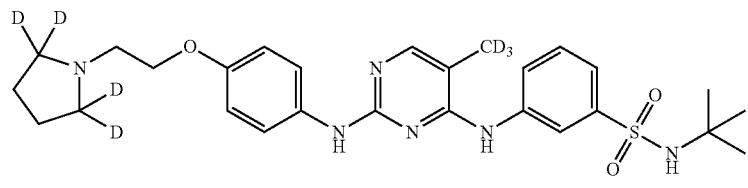
Formula (52)
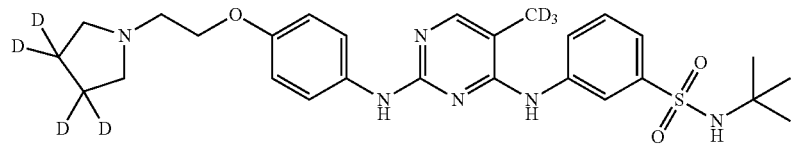
Formula (53)
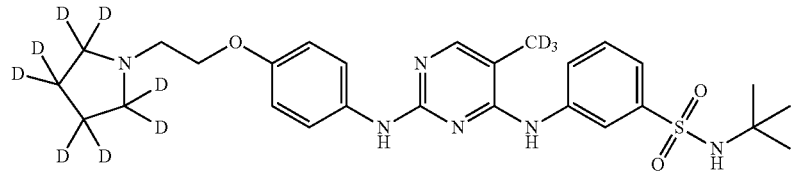
Formula (54)
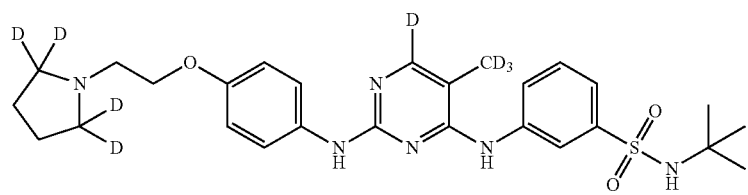
Formula (55)
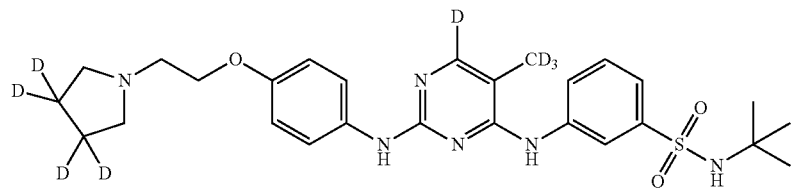
Formula (56)
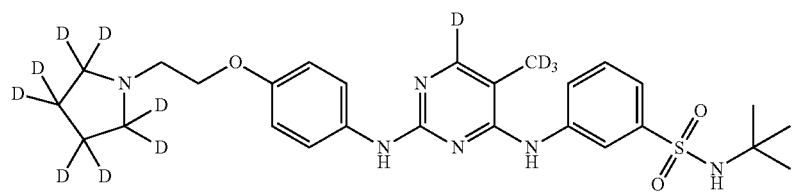
Formula (57)

-continued
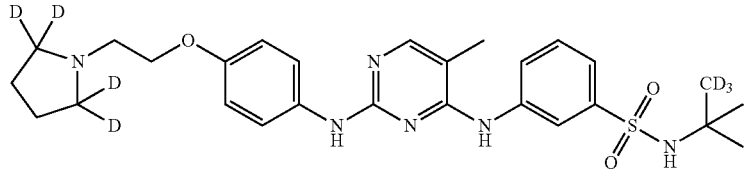
Formula (58)
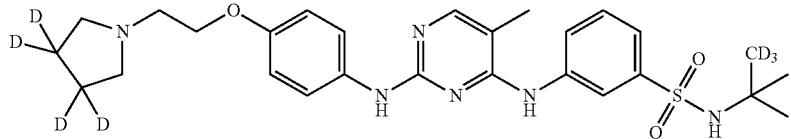
Formula (59)
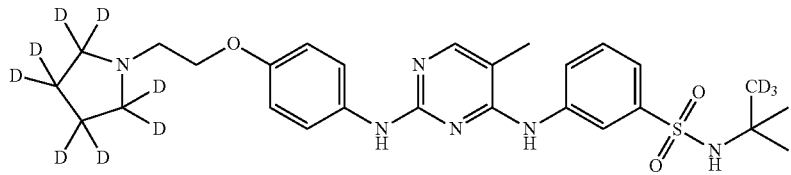
Formula (60)
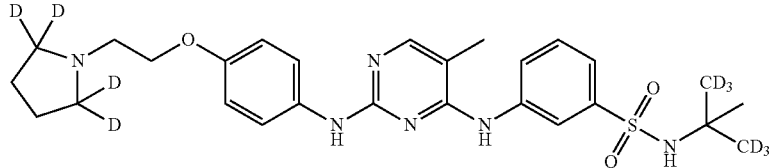
Formula (61)
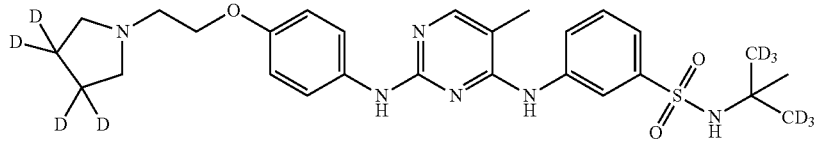
Formula (62)
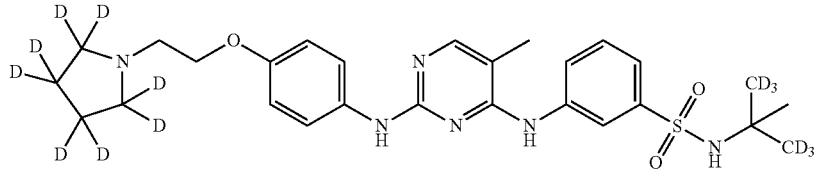
Formula (63)
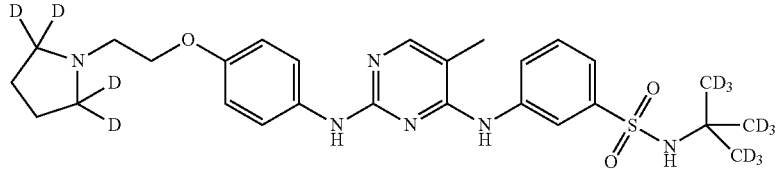
Formula (64)
Formula (65)
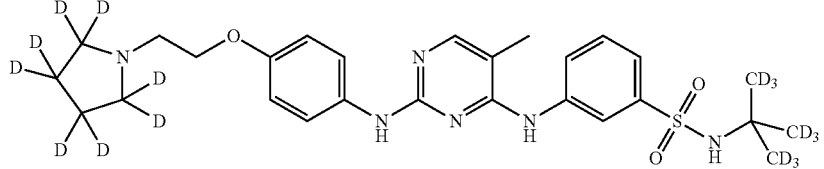
Formula (66)

-continued
Formula (67)
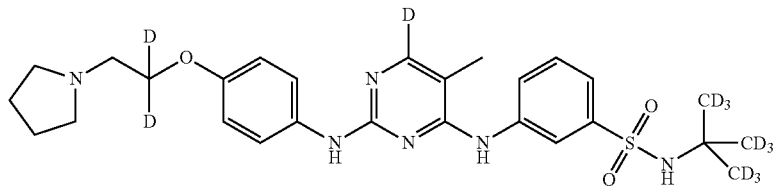
Formula (68)
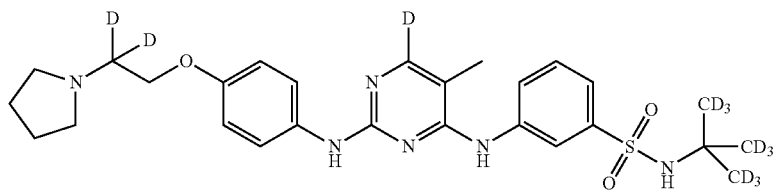
Formula (69)
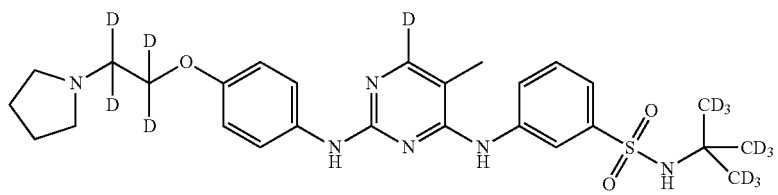
Formula (70)
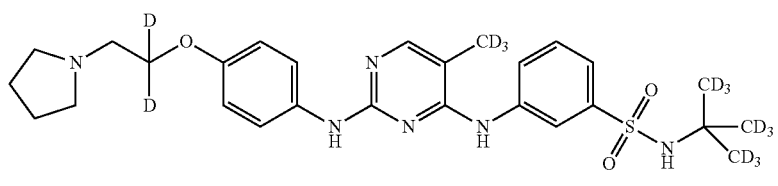
Formula (71)
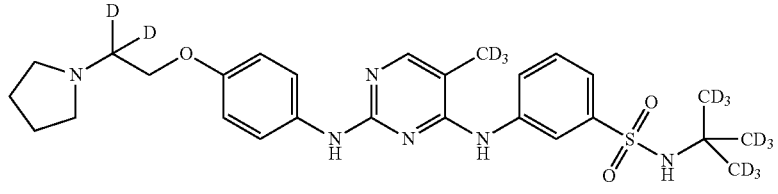
Formula (72)
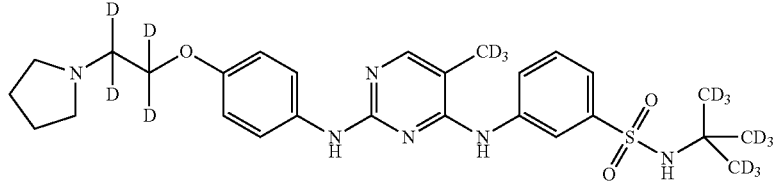
Formula (73)
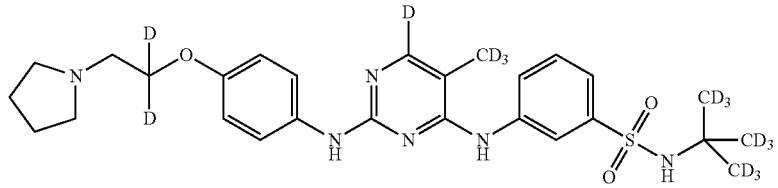
Formula (74)
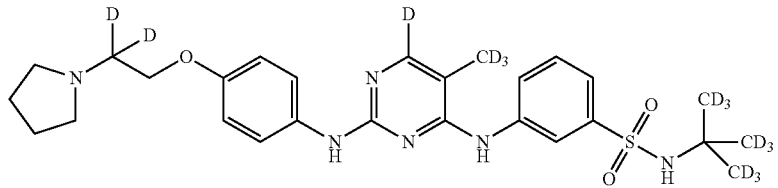

-continued
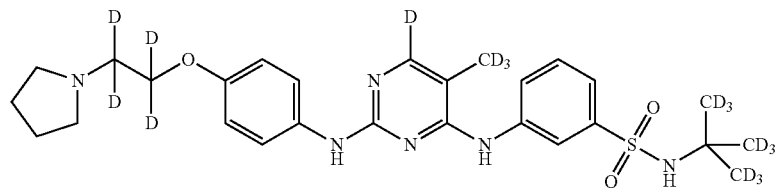
Formula (75)
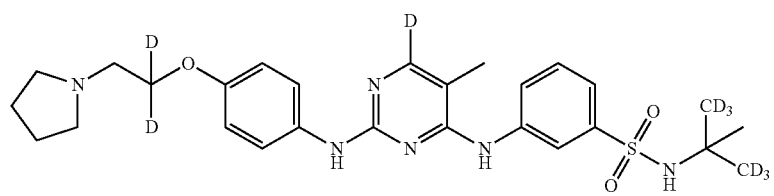
Formula (76)
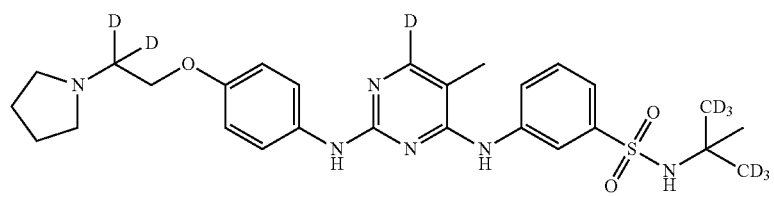
Formula (77)
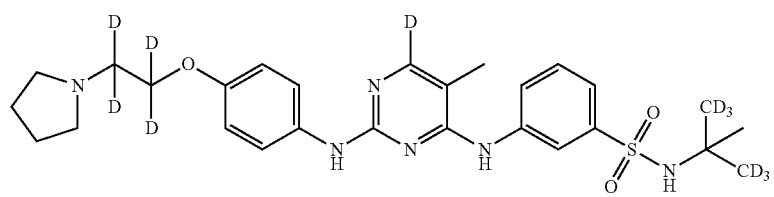
Formula (78)
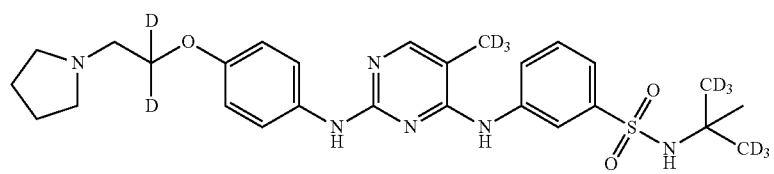
Formula (79)
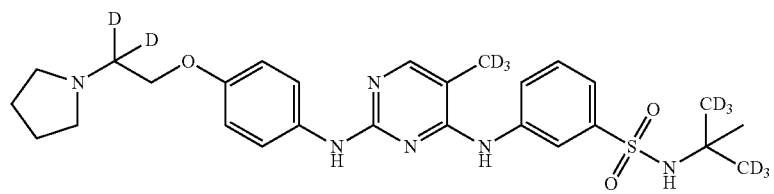
Formula (80)
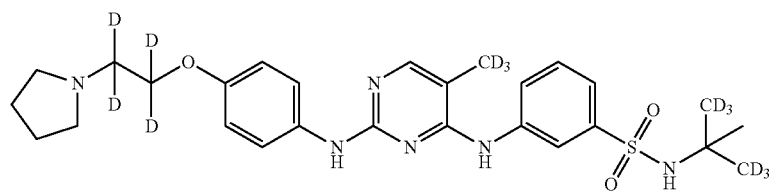
Formula (81)
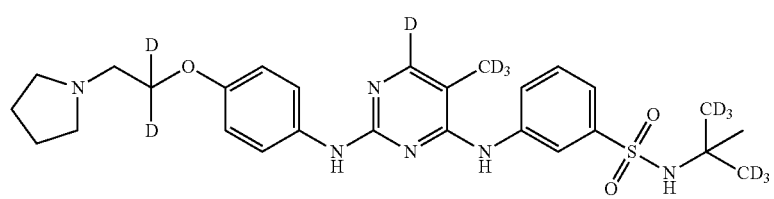
(Formula (82)

-continued
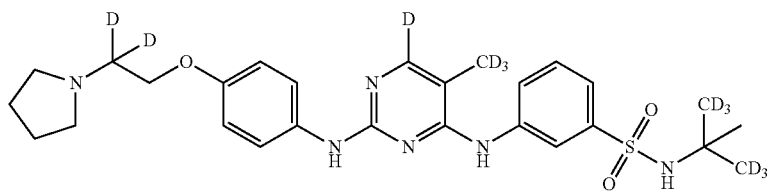
Formula (83)
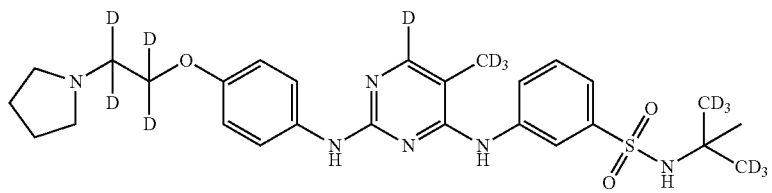
Formula (84)
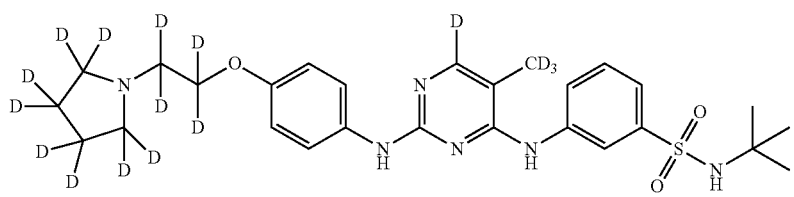
Formula (85)
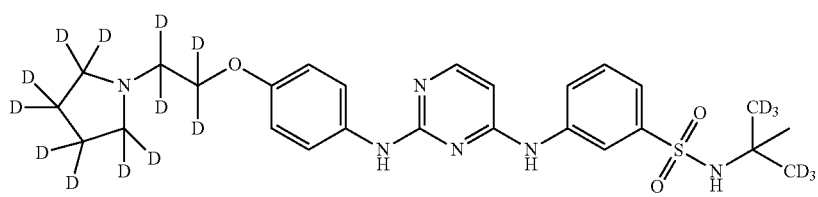
Formula (86)
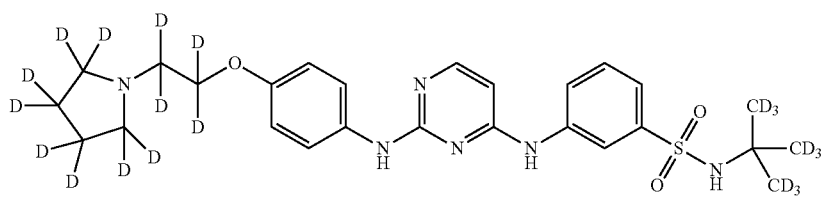
Formula (87)
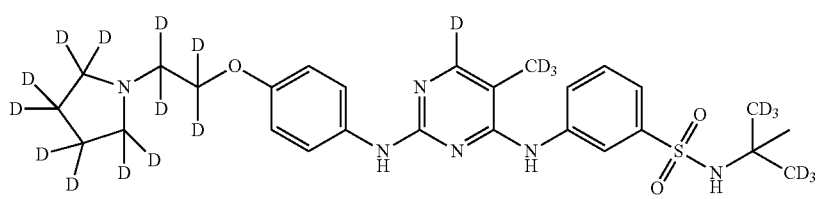
Formula (88)
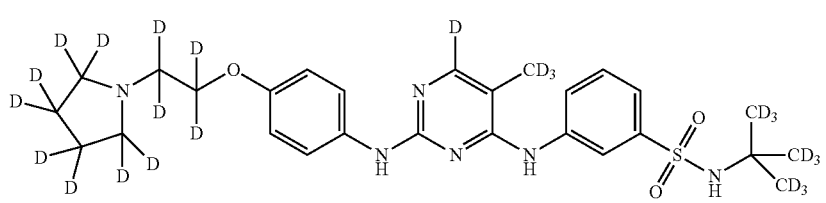
Formula (89)
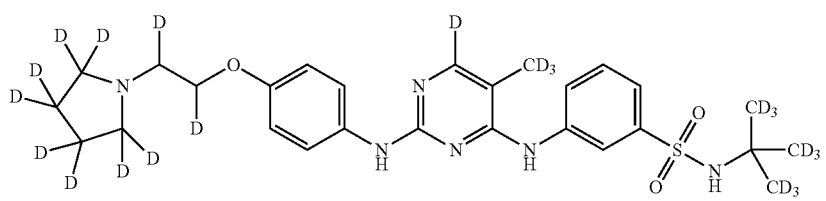
Formula (90)

-continued
Formula (91)
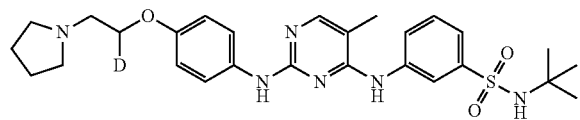
Formula (92)
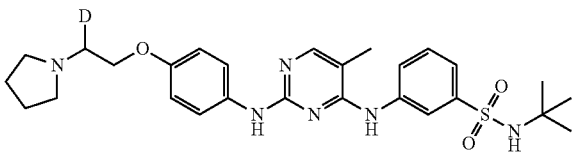
Formula (93)
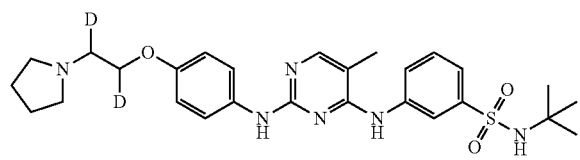
Formula (94)
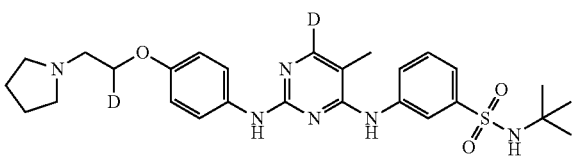
Formula (95)
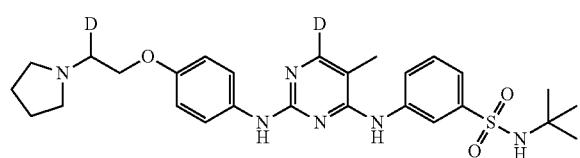
Formula (96)
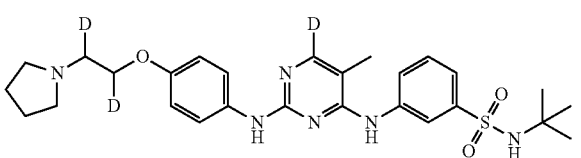
Formula (97)
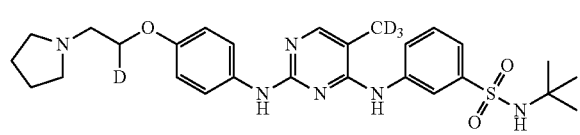
Formula (98)
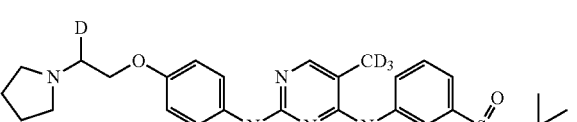
Formula (99)
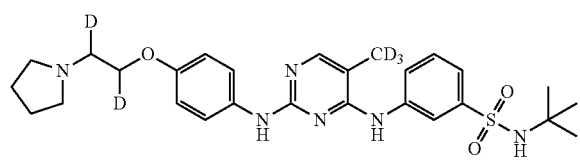
Formula (100)
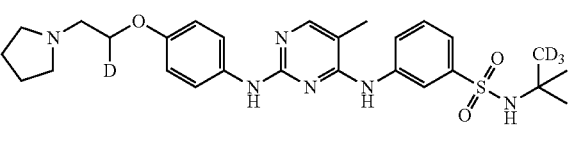
Formula (101)
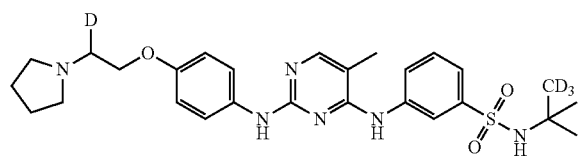
Formula (102)
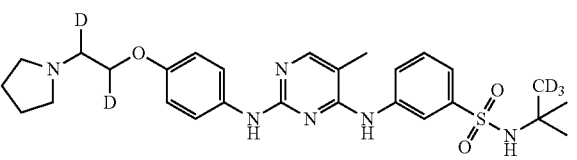
Formula (103)
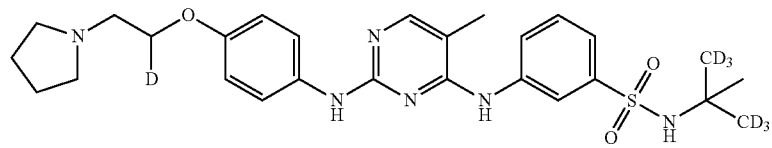
Formula (104)
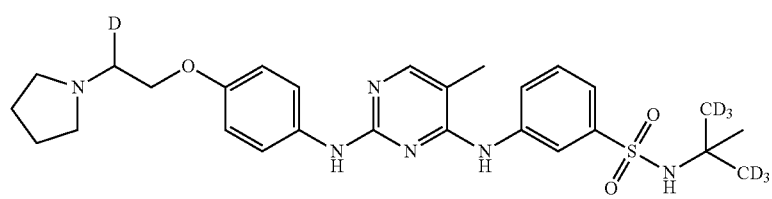

-continued
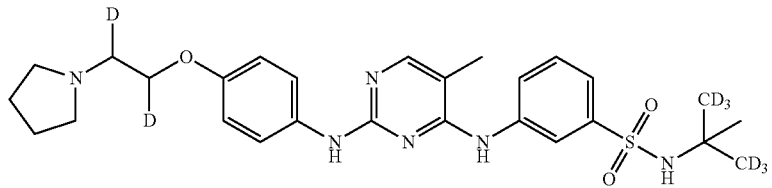
Formula (105)
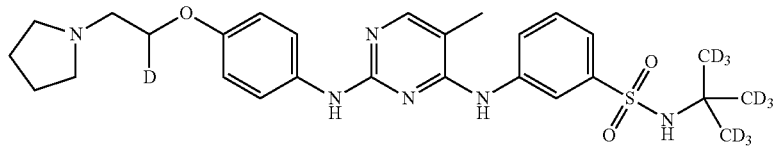
Formula (106)
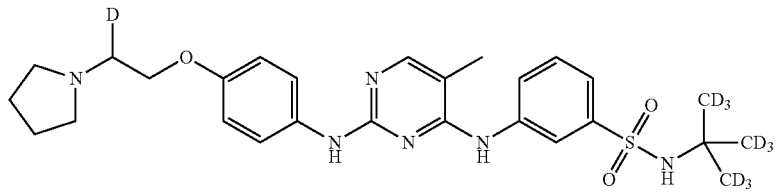
Formula (107)
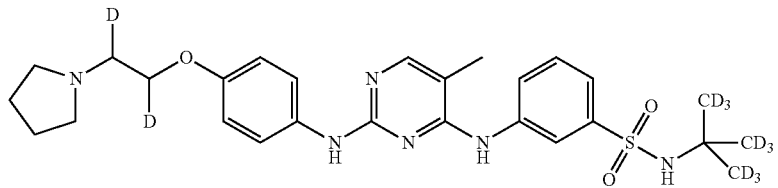
Formula (108)
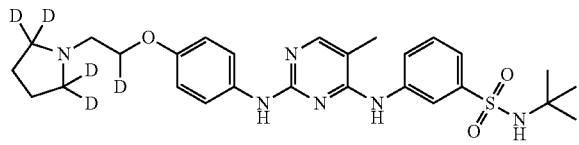
Formula (109)
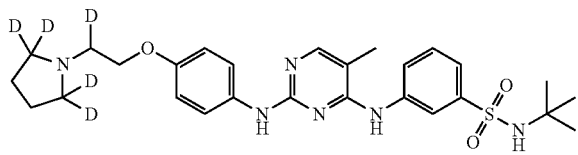
Formula (110)
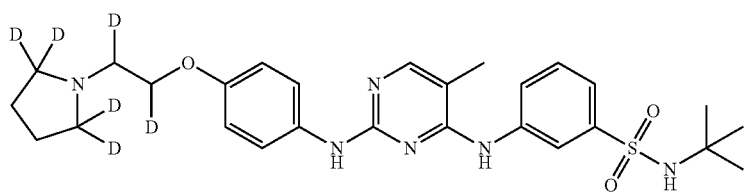
Formula (111)
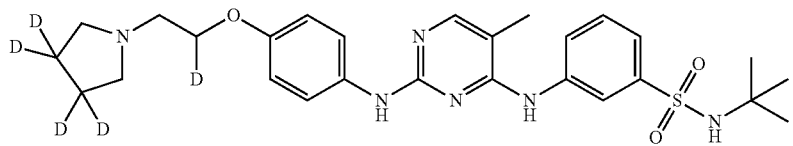
Formula (112)
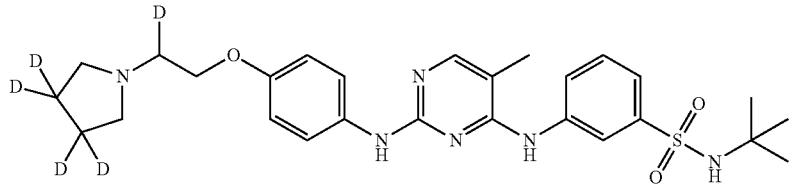
Formula (113)

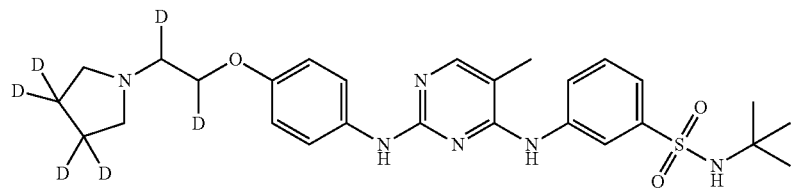

Formula (114)

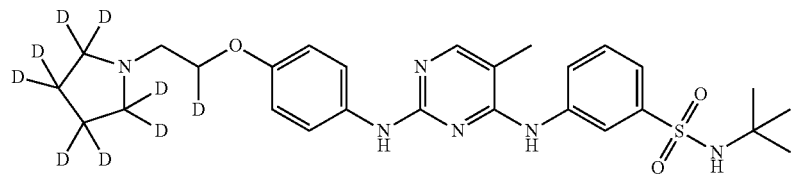

Formula (115)

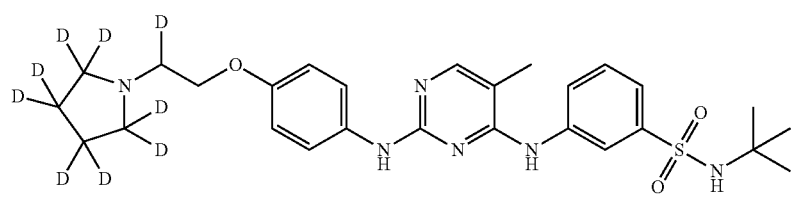

Formula (116)

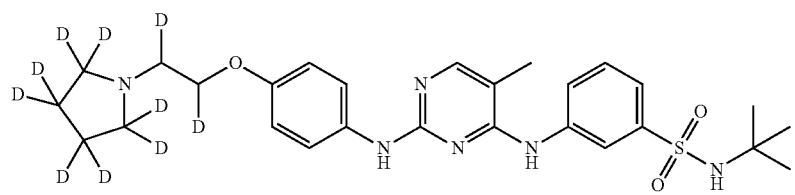

Formula (117)

In another preferred embodiment, the compound does not include a non-deuterated compound.

Pharmaceutical Composition and Method of Administration

In another aspect, provided herein is a pharmaceutical composition comprising the compound disclosed herein (also referred to as "active component") and pharmaceutically acceptable excipients. In some embodiments, the pharmaceutical composition comprises an effective amount of the active component. In some embodiments, the pharmaceutical composition comprises a therapeutically effective amount of the active component. In some embodiments, the pharmaceutical composition comprises a prophylactically effective amount of the active component.

The pharmaceutical composition disclosed herein comprises a safe and effective amount of the compound disclosed herein, or a pharmacologically acceptable salt thereof, and pharmacologically acceptable excipients or carrier. By "safe and effective amount" it is meant that the amount of the compound is sufficient to significantly improve the condition without causing serious side effects. In general, the pharmaceutical composition contains from 0.5 to 2000 mg of the compound disclosed herein per dose, more preferably from 1 to 500 mg of the compound disclosed herein per dose. Preferably, the "one dose" is one capsule or tablet.

"Pharmaceutically acceptable excipient" refers to a non-toxic carrier, adjuvant or vehicle that does not destroy the pharmacological activity of the compound formulated together. Pharmaceutically acceptable carriers, adjuvants, or vehicles that can be used in the compositions disclosed herein include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based substances, polyethylene glycol, sodium carboxymethyl cellulose, polyacrylate, wax, polyethylene-polyoxypropylene block polymer, polyethylene glycol and lanolin.

The pharmaceutical composition disclosed herein can be prepared by combining the compound disclosed herein with a suitable pharmaceutically acceptable excipient, for example, as a solid, semi-solid, liquid or gaseous preparation such as tablets, pills, capsules, powders, granules, ointments, emulsions, suspensions, solutions, suppositories, injections, inhalants, gels, microspheres, aerosols and the like.

Typical routes of administration of the compound disclosed herein or a pharmaceutical composition thereof include, but are not limited to, oral, rectal, transmucosal, enteral administration, or topical, transdermal, inhalation, parenteral, sublingual, intravaginal, intranasal, intraocular, intraperitoneal, intramuscular, subcutaneous, intravenous administration.

The pharmaceutical composition disclosed herein can be produced by a method well known in the art, such as a conventional mixing method, a dissolution method, a granulation method, a sugarcoating pill method, a grinding method, an emulsification method, a freeze drying method, and the like.

For oral administration, the pharmaceutical composition can be formulated by mixing the active compound with pharmaceutically acceptable excipients which are well known in the art. These excipients enable the compound disclosed herein to be formulated into tablets, pills, troches, dragees, capsules, liquids, gels, slurries, suspensions and the like for oral administration to a patient.

A solid oral composition can be prepared by a conventional mixing, filling or tabletting method. For example, it can be obtained by mixing the active compound with a solid excipient, optionally milling the resulting mixture, adding other suitable adjuvants if necessary, and then processing the mixture into granules, thereby obtaining a tablet or a core of dragee. Suitable excipients include, but are not limited to, binders, diluents, disintegrants, lubricants, glidants, sweeteners or flavoring agents, and the like, such as microcrystalline cellulose, glucose solution, acacia mucilage, gelatin solution, sucrose and starch paste; talc, starch, calcium stearate or stearic acid; lactose, sucrose, starch, mannitol, sorbitol or dicalcium phosphate; silica; cross-linked hydroxymethylcellulose sodium, pregelatinized starch, sodium starch glycolate, alginic acid, corn starch, potato starch, methyl cellulose, agar, hydroxymethyl cellulose, cross-linked polyvinyl pyrrolidone and the like. The core of the dragee may optionally be coated according to methods well known in the ordinary pharmaceutical practice, especially using enteric coatings.

The pharmaceutical compositions may also be suitable for parenteral administration, such as sterile solutions, suspensions or lyophilized products in a suitable unit dosage form. Suitable excipients such as fillers, buffers or surfactants can be used.

The compounds disclosed herein may be administered by any route and method of administration, for example by oral or parenteral (e.g., intravenous) administration. A therapeutically effective amount of the compound disclosed herein is from about 0.0001 to 20 mg/kg body weight per day, such as from 0.001 to 10 mg/kg body weight per day.

The dosing frequency of the compounds disclosed herein is determined by the needs of the individual patient, for example, once or twice daily, or more times per day. Administration may be intermittent, for example, wherein the patient receives a daily dose of the compound disclosed herein for a period of several days, and then the patient does not receive a daily dose of the compound disclosed herein for a period of several days or more.

Therapeutic Indications of the Compounds Disclosed Herein

The compounds disclosed herein exhibit inhibitory effects for a JAK2 protein tyrosine kinase. The compounds are used to treat various diseases, either alone or in combination with other active agents (e.g., chemotherapeutic agents or protein therapeutics described below), including, but not limited to: for example, proliferative disorder of bone marrow tissues, proliferative diabetic retinopathy, and other conditions associated with the formation of blood vessels, including solid tumors and other types of cancer, eye diseases, inflammation, psoriasis, and viral infections. Types of cancer that can be treated include, but are not limited to, digestive/gastrointestinal cancer, colon cancer, liver cancer, skin cancer, breast cancer, ovarian cancer, prostate cancer, lymphoma, leukemia (including acute myeloid leukemia and chronic myeloid leukemia), kidney cancer, lung cancer, muscle cancer, bone cancer, bladder cancer or brain cancer.

Some examples of diseases and conditions that can be treated include ocular neovascularization, infant hemangioma; organ hypoxia, vascular proliferation, organ transplant rejection, lupus, multiple sclerosis, rheumatoid arthritis, psoriasis, Type 1 diabetes and complications caused by diabetes, inflammatory diseases, acute pancreatitis, chronic pancreatitis, asthma, rhinitis, atopic dermatitis, autoimmune thyroid disease, ulcerative colitis, Crohn's disease, metastatic melanoma, Kaposi's sarcoma, multiple myeloma, cytokine-related disorders and other autoimmune gastritis, autoimmune hemolytic disease, autoimmune neutropenia, thrombocytopenia, atopic disease (for example, allergic asthma, atopic dermatitis or allergic rhinitis), chronic active hepatitis, myasthenia gravis, multiple sclerosis, inflammatory bowel disease, graft versus host disease, neurodegenerative disease, including motor neuron disease, Alzheimer's disease, Parkinson's disease, amyotrophic lateral sclerosis, Huntington's disease, cerebral ischemia or neurodegenerative disease caused by bruises, stroke, glutamate neurotoxicity or hypoxia; ischemia/reperfusion injury in stroke, myocardial ischemia, renal ischemia, heart attack, cardiac hypertrophy, atherosclerosis and arteriosclerosis, organ hypoxia, and platelet aggregation.

Examples of some additional diseases and disorders that can be treated also include cell mediated hypersensitivity (allergic contact dermatitis, hypersensitivity pneumonitis), rheumatic diseases (e.g., systemic lupus erythematosus, juvenile arthritis, Sjogren's Syndrome, scleroderma, polymyositis, ankylosing spondylitis, psoriatic arthritis), viral diseases (Epstein Barr Virus, Hepatitis B, Hepatitis C, HIV, HTLV1, Vaicella-Zoster Virus, Human Papilloma Virus), food allergy, cutaneous inflammation, and immune suppression induced by solid tumors.

In some embodiments, the compounds or the compositions disclosed herein are useful for treating primary myelofibrosis. In some embodiments, the compounds or the compositions disclosed herein are useful for treating myelofibrosis following polycythemia vera. In some embodiments, the compounds or the compositions disclosed herein are useful for treating myelofibrosis following idiopathic thrombocythemia. In some embodiments, the compounds or the compositions disclosed herein are useful for treating high-risk myelofibrosis. In some embodiments, the compounds or the compositions disclosed herein are useful for treating a moderate risk of myelofibrosis (e.g., a moderate risk level of 2). In some embodiments, the compounds disclosed herein are useful for treating myelofibrosis in which the mutation of valine 617 of JAK2 to phenylalanine (i.e., V617F) is positive. In some embodiments, the compounds disclosed herein are useful for treating myelofibrosis in which the mutation of valine 617 of JAK2 to phenylalanine (i.e., V617F) is negative.

Combination Therapy

The compounds disclosed herein are administered to a subject in need of such treatment with an anti-inflammatory agent, antihistamine, a chemotherapeutic agent, an immunomodulatory agent, a therapeutic antibody or a protein kinase inhibitor, such as a tyrosine kinase inhibitor. Although not required to be limiting, a chemotherapeutic agent includes antimetabolites such as methotrexate, DNA crosslinkers such as cisplatin/carboplatin; alkylating agents such as canbusil; topoisomerase I inhibitors such as dactinomycin; microtubule inhibitors such as Taxol (paclitaxol) and the like. Other chemotherapeutic agents include, for example, vinca alkaloids, mitomycin antibiotics, bleomycin antibiotics, antifolates, colchicine, demecoline, etoposide, taxanes, anthracycline antibiotics, doxorubicin, daunorubicin, carminomycin, epirubicin, idarubicin, mitoxanthrone, 4-dimethoxy-danomycin, 11-deoxydaunorubicin, 13-deoxydaunorubicin, adriamycin-14-benzoate, adriamycin-14- octanoate, adriamycin-14-naphthyl acetate, amsacrine, carmustine, cyclophosphamide, cytarabine, etoposide, lovastatin, melphalan, topotecan, oxalaplatin, chlorambucil, methtrexate, lomustine, thioguanine, asparaginase, vinblastine, vindesine, tamoxifen or mechlorethamine. Although not required to be limiting, therapeutic antibodies include antibodies directed to a HER2 protein, such as trastuzumab; antibodies directed to growth factors or growth factor receptors, such as bevacizumab targeting vascular endothelial growth factor and OSI-774 targeting epidermal growth factor; antibodies targeting integrin receptor, such as Vitaxin (also known as MEDI-522) and the like. Types of anticancer drugs suitable for the compositions and methods disclosed herein include, but are not limited to: 1) alkaloids, including microtubule inhibitors (e.g., vincristine, vinblastine, and vindesine, etc.), microtubule stabilizers (e.g., paclitaxel [taxol] and docetaxel, taxotere, etc.) and chromatin function inhibitors, including topoisomerase inhibitors, such as epipodophyllotoxin (e.g., etoposide [VP-16] and teniposide [VM-26], etc.) and active agents that target topoisomerase I (e.g., camptothecin and isirinotecan [CPT-11], etc.); 2) covalent DNA-binding agents [alkylating agents], including mechlorethamine (e.g., nitrogen mustard, chlorambucil, cyclophosphamide, ifosfamide, and busulfan [Busulphan], etc.), nitrosoureas (e.g., carmustine, lomustine, and semustine, etc.) and other alkylating agents (such as dacarbazine, Hydroxymethyhnelamine, thiotepa and mitocycin, etc.); 3) non-covalent DNA-binding agents [antitumor antibiotics], including nucleic acid inhibitors (e.g., actinomycin D [dactinomycin], etc.), anthracyclines (e.g., daunorubicin [daunomycin and Cerubidine], doxorubicin [adriamycin] and idarubicin [demethoxydaunorubicin], etc.), anthraquinones (e.g., anthracycline analogs such as [mitoxantrone], etc.), bleomycin (bleomycin), etc., and plicamycin (mithramycin), etc.; 4) antimetabolites, including antifolates (e.g., methotrexate, folex and methotrexate sodium, etc.), purine antimetabolites (e.g., 6-mercaptopurine [6-MP, mercaptopurine], 6-thioguanine [6-TG], azathioprine, acyclovir, ganciclovir, chlorodeoxyadenosine, 2-chlorodeoxyadenosine [CdA] and 2'-deoxycoformycin [pentostatin], etc.), pyrimidine antagonists (e.g., fluoropyrimidines [e.g., 5-fluorouracil (Adrucil), 5-fluorodeoxyuridine (FdUrd)(fluorouridine), etc.) and cytosine arabinosides (e.g., Cytosar [ara-C] and fludarabine, etc.); 5) enzymes, including L-asparaginase; 6) hormones, including glucocorticoids, such as anti-estrogens (such as tamoxifen, etc.), non-steroidal antiandrogens (such as flutamide, etc.) and aromatase inhibitors (e.g., anastrozole [Arimidex], etc.); 7) platinum compounds (e.g., cisplatin and carboplatin, etc.); 8) monoclonal antibodies conjugated with anticancer drugs, toxins and/or radionuclides, etc.; 9) biological response modifiers (e.g., interferon [e.g., IFN-α, etc.] and interleukin [e.g., IL-2, etc.], etc.); 10) adoptive immunotherapy; 11) hematopoietic growth factors; 12) active agents that induce tumor cell differentiation (e.g., all-trans retinoic acid, etc.); 13) gene therapy techniques; 14) antisense therapy techniques; 15) tumor vaccines; 16) therapy directed to a metastasis tumor (e.g., Batimistat, etc.); and 17) angiogenesis inhibitors.

The pharmaceutical compositions and methods disclosed herein may further comprise other therapeutically active compounds as described herein which are commonly employed in the treatment of the above mentioned pathologies. Examples of other therapeutic agents include the following: cyclosporins (e.g., cyclosporin A); CTLA4-Ig; antibodies such as ICAM-3, anti-IL-2 receptor (anti-Tac), anti-CD45RB, anti-CD2, anti-CD₃(OKT-3), anti-CD4, anti-CD80, anti-CD86; an active agent that blocks the interaction of CD40 with gp39, such as an antibody specific for CD40 and/or gp39 (i.e., CD154), fusion proteins constructed from CD40 and gp39 (CD40Ig and CD8gp39), inhibitors of NF-κB function, such as nuclear translocation inhibitors, such as deoxyspergualin (DSG); cholesterol biosynthesis inhibitors, such as HMG CoA reducase inhibitors (lovastatin and simvastatin); non-steroidal anti-inflammatory drugs (NSAIDs) such as ibuprofen and cyclooxygenase inhibitors such as rofecoxib; steroids such as prednisone or dexamethasone; Gold compounds; antiproliferative drugs, such as methotrexate, FK506 (tacrolimus, prograf), mycophenolate mofetil, cytotoxic drugs such as azathioprine and cyclophosphamide; TNF-a inhibitor, such as tenidap; an anti-TNF antibody or soluble TNF receptor and rapamycin (sirolimus or rapamune) or a derivative thereof.

Other active agents that can be administered in combination with the compounds disclosed herein include protein therapeutics such as cytokines, immunomodulators and antibodies. The term "cytokine" as used herein includes chemokines, interleukins, lymphokines, mononuclear factors, colony stimulating factors and receptor-associated proteins and functional fragments thereof. The term "functional fragment" as used herein means a polypeptide or peptide having biological function or activity identified by a defined functional assay.

Cytokines include endothelial monocyte activation polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12 and IL-13, interferons, etc. and are associated with specific biological, morphological or phenotypic alterations in cellular or cellular mechanisms.

When other therapeutic agents are used in combination with the compounds disclosed herein, they can be used, for example, in the amounts indicated in the Physician Desk Reference (PDR), otherwise determined by those skilled in the art.

In the treatment or prevention of a condition involving cell proliferation, an appropriate dosage level is generally from about 0.01 to about 1000 mg per 1 kg of patient body weight per day, which may be administered in single or multiple doses. For example, the dosage level can range from about 0.01 to about 250 mg/kg/day; more narrowly from about 0.5 to about 100 mg/kg/day. Suitable dosage levels can range from about 0.01 to about 250 mg/kg/day, from about 0.05 to about 100 mg/kg/day or from about 0.1 to about 50 mg/kg/day or about 1.0 mg/kg/day. For example, within this range, the dosage can be from about 0.05 to about 0.5 mg/kg/day or from about 0.5 to about 5 mg/kg/day or from about 5 to about 50 mg/kg/day. For oral administration, the compositions are formulated to comprise from about 1.0 to about 1,000 mg of the active component, for example, about 1.0, about 5.0, about 10.0, about 15.0, about 20.0, about 25.0, about 50.0, about 75.0, about 100.0, about 150.0, about 200.0, about 250.0, about 300.0, about 400.0, about 500.0, about 600.0, about 750.0, about 800.0, about 900.0 and about 1,000.0 mg of the active component in a tablet form so as to adjust the dose according to the symptoms of the patient being treated. The compound can be administered in a regimen of from 1 to 4 times per day, such as once or twice per day. There may be periods of no dosing followed by another dosing regimen.

However, it will be appreciated that the particular dosage level and dosage frequency for any particular patient may vary, and depend on various factors, including the activity of the particular compound employed, the metabolic stability and duration of action of the compound, age, weight, general health, gender, diet, mode of administration and timing, rate of excretion, combination of drugs, severity of the specific condition, and ongoing therapy of the host.

The compounds disclosed herein may be used alone or in combination with an effective amount of a therapeutic antibody (or a therapeutic fragment thereof), a chemotherapeutic agent or an immunotoxic agent to treat a tumor. Illustrative examples of chemotherapeutic agents that can be used for this purpose include doxorubicin, docetaxel or taxol. It is to be further understood that the present disclosure encompasses combination therapies comprising the compound disclosed herein, including, but not limited to, vasculostatic agents, such as tyrosine, serine or threonine kinase inhibitors, and any chemotherapeutic agent or a therapeutic antibody.

The compounds disclosed herein have a number of advantages over non-deuterated compounds known in the art. The advantages of the present disclosure include: first, the compounds and compositions of the technical solutions disclosed herein provide a more advantageous therapeutic tool for the treatment of JAK2-mediated diseases; second, the metabolism of the compound in organisms is improved, giving the compound better pharmacokinetic characteristics; in this case, the dosage can be changed and a long-acting formulation can be formed, thereby improving the applicability; third, the drug concentration of a compound in the animal is increased, and the drug efficacy is improved; and fourth, certain metabolites are inhibited, and the safety of the compound is increased.

EXAMPLES

The present disclosure is further illustrated below in conjunction with specific examples. It is to be understood that the examples are used to illustrate the present disclosure, and not intended to limit the scope of present disclosure. In the following examples, the experimental methods wherein the particular conditions are not specified are usually in accordance with conventional conditions or according to the conditions recommended by the manufacturer. Parts and percentages are parts by weight and percentage by weight unless otherwise stated.

Usually, in the preparation process, each reaction is usually carried out in an inert solvent at room temperature to reflux temperature (e.g., 0° C. to 100° C., preferably 0° C. to 80° C.). The reaction time is usually from 0.1 to 60 hours, preferably from 0.5 to 24 hours.

Example 1. Preparation of N-(tert-butyl)-3-((5-methyl-2-((4-(2-(pyrrolidin-1-yl)ethoxy-1,1,2,2-d$_4$)phenyl)amino)pyrimidin-4-yl)amino)benzenesulfonamide (Compound T-1)

The synthesis was carried out using the following route:

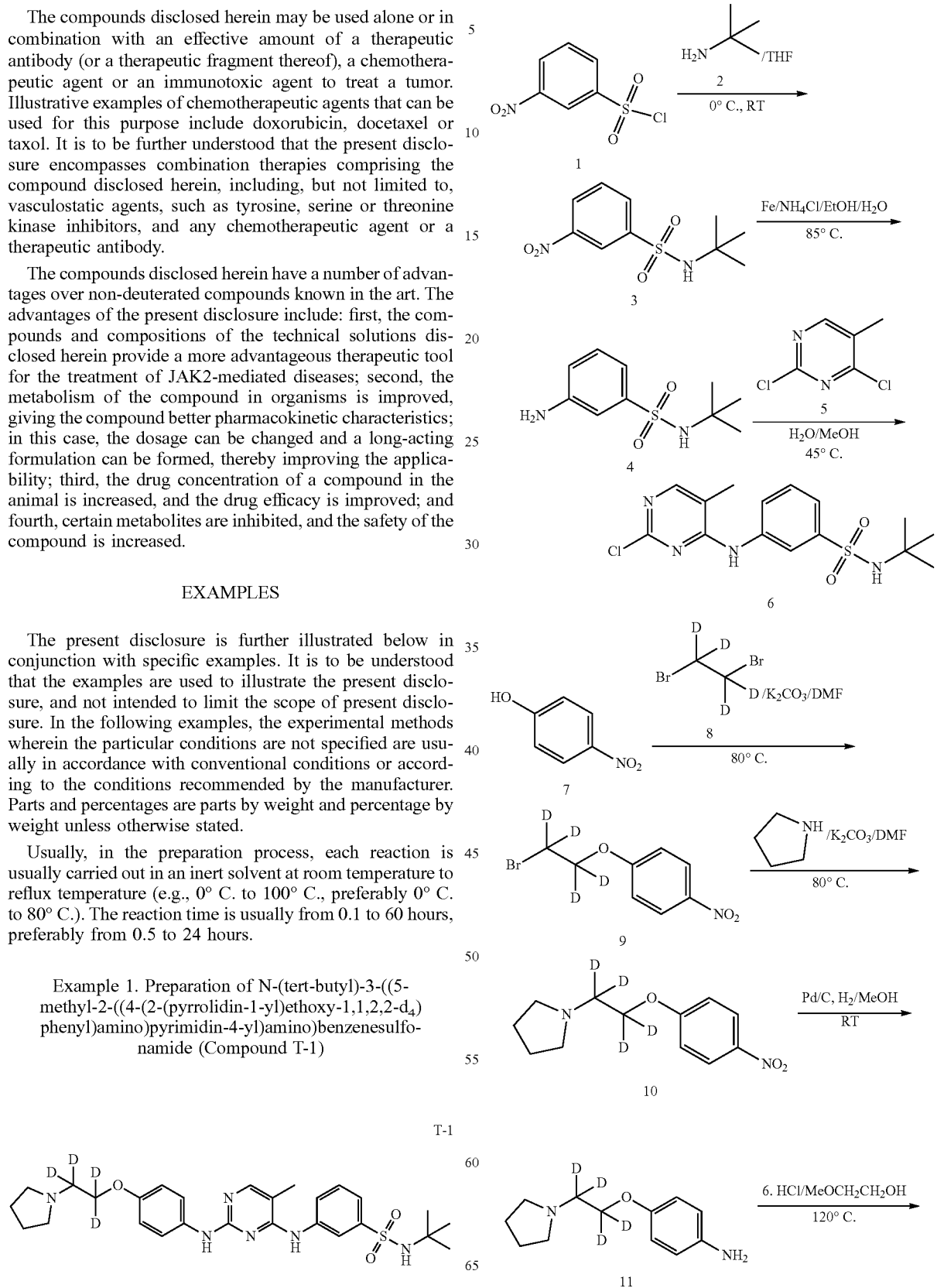

-continued

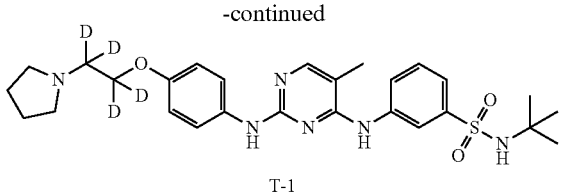

T-1

Step 1 Synthesis of Compound 3.

Compound 1 (10.0 g, 45.12 mmol) and THF (100 mL) were sequentially added to a 250 mL single-necked flask with a magnetic stirrer. The mixture was stirred and dissolved. A solution of tert-butylamine (9.9 g, 135.37 mmol) in THF (20 mL) was slowly added dropwise to the mixture in an ice water bath. After completion of the dropwise addition, the ice water bath was removed, and the reaction was stirred at room temperature for 1 hour under a nitrogen atmosphere. The organic solvent was evaporated under reduced pressure. To the resulting residue was added water (50 mL). The mixture was extracted with dichloromethane (50 mL×3). The organic phases were combined, washed with saturated brine, dried over anhydrous sodium sulfate, filtered, concentrated and separated by silica gel column chromatography to give 9.5 g of a white solid in a yield of 81.6%. LC-MS (APCI): m/z=259.1 (M+1)$^+$. $^1$H NMR (500 MHz, CDCl$_3$) δ ppm: 8.75 (t, J=2.0 Hz, 1H), 8.40 (dd, J=8.0 Hz, J=2.0 Hz, 1H), 8.24 (dd, J=8.0 Hz, J=2.0 Hz, 1H), 7.73 (t, J=8.0 Hz, 1H), 4.99 (s, 1H), 1.27 (s, 9H).

Step 2 Synthesis of Compound 4.

An ethanol/water mixture (60 mL, 2/1) and Compound 3 (3.0 g, 11.66 mmol) were added to a 100 mL single-necked flask equipped with a magnetic stirrer and a condensing tube. Reduced iron powder (6.51 g, 116.6 mmol) and ammonium chloride (3.12 g, 58.3 mmol) were added to the mixture with stirring. The mixture was heated to 85° C. under nitrogen, and stirred for 1 h at this temperature.

After cooling to room temperature, insoluble solid was filtered off, and the organic solvent was evaporated under reduced pressure. To the resulting residue was added saturated aqueous NaHCO$_3$ (5 mL), and the mixture was extracted with ethyl acetate (50 mL×3). The organic phases were combined, dried over anhydrous sodium sulfate, filtered, and concentrated to give 2.55 g of a white solid in a yield of 95.79%. LC-MS (APCI): m/z=229.1 (M+1)$^+$.

Step 3 Synthesis of Compound 6.

Compound 5 (1.0 g, 6.13 mmol) and methanol/water mixture (15 mL, 1/1) were sequentially added to a 50 mL single-necked flask with a magnetic stirrer at room temperature. The mixture was stirred and dissolved. Compound 4 (1.26 g, 5.52 mmol) was added to the mixture. The reaction mixture was heated to 45° C. under nitrogen and stirred to react overnight at this temperature. After cooling to room temperature, a large amount of a white solid was precipitated, which was filtered. The filter cake was washed with methanol/water (3.4 mL/4.0 mL), dried by suction, and dried under vacuum at 50° C. to give 1.31 g of a white solid in a yield of 60.17%. LC-MS (APCI): m/z=354.1 (M+1)$^+$. $^1$H NMR (500 MHz, DMSO-D$_6$) δ ppm: 9.11 (s, 1H), 8.11-8.09 (m, 2H), 7.88-7.86 (m, 1H), 7.55-7.52 (m, 3H), 2.18 (s, 3H), 1.12 (s, 9H).

Step 4 Synthesis of Compound 9.

Compound 7 (300 mg, 2.16 mmol) and DMF (6 ml) were added sequentially to a 50 mL single-necked flask with a magnetic stirrer. The mixture was stirred and dissolved. Potassium carbonate (894 mg, 6.47 mmol) and Compound 8 (827 mg, 4.31 mmol) were added to the mixture. The reaction mixture was heated to 80° C. under a nitrogen atmosphere and stirred to react for 4 hours at this temperature. After cooling to room temperature, 30 mL of water was added. The mixture was extracted with ethyl acetate (30 mL×3). The organic phases were combined, washed with water (60 mL×3) and saturated brine (30 mL), dried over anhydrous sodium sulfate, filtered, concentrated and separated by silica gel column to give 450 mg of a white solid in a yield of 83.4%. LC-MS (APCI): m/z=250.0 and 252.0 (M+1)$^+$.

Step 5 Synthesis of Compound 10

Compound 9 (450 mg, 1.8 mmol) and DMF (6 ml) were sequentially added to a 50 mL single-necked flask with a magnetic stirrer. The mixture was stirred and dissolved. Potassium carbonate (746 mg, 5.4 mmol) and pyrrolidine (256 mg, 3.6 mmol) were added to the mixture. The reaction mixture was heated to 80° C. under a nitrogen atmosphere and stirred to react for 4 hours at this temperature. After cooling to room temperature, 30 mL of water was added. The mixture was extracted with ethyl acetate (30 mL×3). The organic phases were combined, washed with water (60 mL×3) and saturated brine (30 mL), dried over anhydrous sodium sulfate, filtered, concentrated and separated by silica gel column to give 250 mg of a yellow oil in a yield of 57.8%. LC-MS (APCI): m/z=241 (M+1)$^+$.

Step 6 Synthesis of Compound 11

Compound 10 (250 mg, 1.04 mmol) and methanol (10 mL) were added to a 50 mL single-necked flask with a magnetic stirrer. The mixture was stirred and dissolved. Pd/C (25 mg, 10%) was added. The atmosphere was vacuumed and replaced with hydrogen under a hydrogen balloon for three times. The reaction was carried out overnight under a hydrogen atmosphere. The catalyst was filtered off, and the filter cake was washed with methanol (3 mL). The filtrates were combined and concentrated to give 220 mg of a yellow oil in a yield of 98.6%. LC-MS (APCI): m/z=211.1 (M+1)$^+$.

Step 7 Synthesis of Compound T-1

Compound 6 (200 mg, 0.56 mmol), Compound 11 (107 mg, 0.51 mmol) and ethylene glycol monomethyl ether (6 mL) were added to a 25 mL single-necked flask with a magnetic stirrer and a condensing tube. The mixture was stirred and dissolved. A solution of hydrogen chloride in isopropanol (1.41 mmol, 0.28 mL, 5 M) was added dropwise. The mixture was heated to 120° C. under a nitrogen atmosphere and stirred to react overnight at this temperature. After cooling to room temperature, water (10 mL) and saturated sodium bicarbonate (5 mL) were added. The mixture was extracted with dichloromethane (15 mL×3). The organic phases were combined, washed with saturated brine, dried over anhydrous sodium sulfate, filtered, and concentrated. The residue was separated by silica gel column to give 150 mg of a white solid in a yield of 50.3%. LC-MS (APCI): m/z=529.2 (M+1)$^+$. $^1$H NMR (500 MHz, CDCl$_3$) δ ppm: 8.11 (s, 1H), 7.92-7.89 (m, 2H), 7.57 (d, J=8.0 Hz, 1H), 7.41-7.38 (m, 3H), 6.91 (d, J=8.0 Hz, 1H), 6.81 (s, 1H), 6.44 (s, 1H), 4.60 (s, 1H), 4.13 (t, J=6.0 Hz, 2H), 2.94 (t, J=6.0 Hz, 2H), 2.13 (s, 3H), 1.22 (s, 9H).

Example 2 Preparation of N-(tert-butyl)-3-((5-(methyl-d₃)-2-((4-(2-(pyrrolidin-1-yl)ethoxy)phenyl)amino)pyrimidin-4-yl-6-d)amino)benzenesulfonamide (Compound T-2)

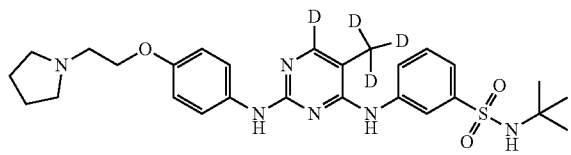

T-2

The synthesis was carried out using the following route:

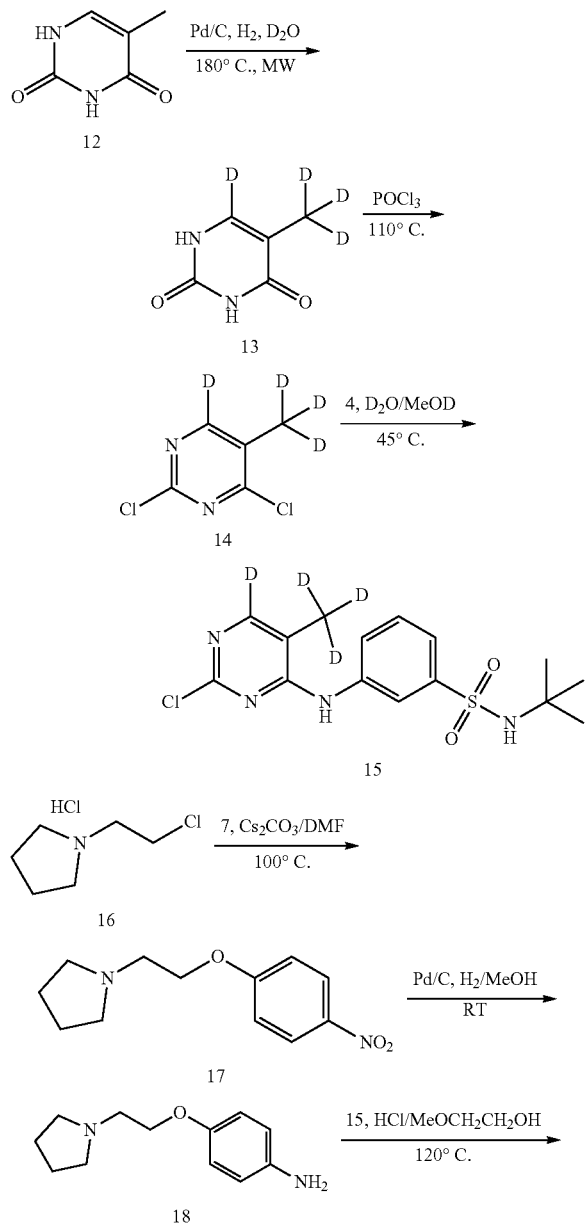

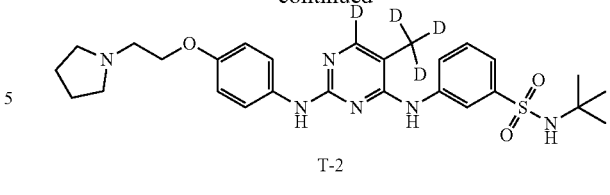

T-2

Step 1 Synthesis of Compound 13

Compound 12 (1.0 g, 7.93 mmol), Pd/C (200 mg, 10%) and heavy water (15 mL) were added to a 20 mL microwave tube containing a magnetic stirrer. The mixture was bubbled with a hydrogen gas for 2 minutes. The microwave tube was sealed, placed in a microwave reactor and heated to 180° C. to react for 1 hour. After cooling to room temperature, the catalyst was filtered off. The filtrate was extracted with ethyl acetate (30 mL×3). The organic phases were combined, dried over anhydrous sodium sulfate, filtered, concentrated and separated by silica gel column to give 700 mg of a white solid in a yield of 67.8%. LC-MS (APCI): m/z=131.1 (M+1)⁺. ¹H NMR (300 MHz, DMSO-d₆) δ ppm: 11.00 (s, 1H), 10.58 (s, 1H).

Step 2 Synthesis of Compound 14

Compound 13 (360 mg, 2.77 mmol) and phosphorus oxychloride (5 mL) were sequentially added to a 50 mL three-necked flask with a magnetic stirrer, heated to 110° C. under a nitrogen atmosphere and stirred to react overnight at this temperature. The unreacted phosphorus oxychloride was evaporated under reduced pressure. The residue was dissolved in ethyl acetate (40 mL). A saturated aqueous solution of sodium bicarbonate (10 mL) was added to the mixture, stirred for 5 minutes and allowed to separate into layers. The organic phase was dried over anhydrous sodium sulfate, filtered, concentrated and separated by silica gel column to give 400 mg of a white solid in a yield of 86.5%. LC-MS (APCI): m/z=168.1 (M+1)⁺.

Step 3 Synthesis of Compound 15

Compound 14 (400 mg, 2.39 mmol) and MeOD/heavy water mixture (10 mL, 1/1) were sequentially added to a 50 mL single-necked flask with a magnetic stirrer at room temperature, stirred and dissolved. Compound 4 (382 mg, 1.68 mmol) was added to the mixture. The reaction mixture was heated to 45° C. under nitrogen and stirred to react overnight at this temperature. After cooling to room temperature, a large amount of a white solid was precipitated, which was filtered. The filter cake was washed with MeOD/heavy water (2 mL/2 mL), dried by suction, and dried under vacuum at 50° C. to give 400 mg of a white solid in a yield of 46.7%. LC-MS (APCI): m/z=358.1 (M+1)⁺. ¹H NMR (400 MHz, DMSO-D₆) δ/ppm: 9.11 (s, 1H), 8.11-8.09 (m, 1H), 7.88-7.86 (m, 1H), 7.55-7.52 (m, 3H), 1.12 (s, 9H).

Step 4 Synthesis of Compound 17

Compound 7 (1.0 g, 7.19 mmol), Compound 16 (1.58 g, 9.35 mmol) and DMF (20 ml) were sequentially added to a 50 mL single-necked flask with a magnetic stirrer. Cs₂CO₃ (cesium carbonate, 7.0 g, 21.6 mmol) was added to the mixture with stirring. The reaction mixture was heated to 100° C. under a nitrogen atmosphere and stirred to react overnight at this temperature. After cooling to room temperature, 30 mL of water was added. The mixture was extracted with ethyl acetate (30 mL×3). The organic phases were combined, washed with water (60 mL×3) and saturated brine (30 mL), dried over anhydrous sodium sulfate, filtered, concentrated and separated by silica gel column to give 1.2 g of a white solid in a yield of 70.4%. LC-MS (APCI): m/z=237.1 (M+1)⁺. ¹H NMR (300 MHz, CDCl₃) δ ppm:

8.20 (d, J=9.0 Hz, 2H), 6.98 (d, J=9.0 Hz, 2H), 4.21 (t, J=6.0 Hz, 2H), 2.96 (t, J=6.0 Hz, 2H), 2.67-2.64 (m, 4H), 1.88-1.82 (m, 4H).

Step 5 Synthesis of Compound 18

Compound 17 (250 mg, 1.04 mmol) and methanol (10 mL) were added to a 50 mL single-necked flask with a magnetic stirrer, stirred and dissolved. Pd/C (25 mg, 10%) was added to the mixture. The atmosphere was vacuumed and replaced with hydrogen under a hydrogen balloon for three times. The reaction was carried out overnight under a hydrogen atmosphere. The catalyst was filtered off, and the filter cake was washed with methanol (3 mL). The filtrates were combined and concentrated to give 220 mg of a yellow oil in a yield of 98.6%. LC-MS (APCI): m/z=207.1 (M+1)$^+$.

Step 6 Synthesis of Compound T-2

Compound 15 (200 mg, 0.56 mmol), Compound 18 (107 mg, 0.51 mmol) and ethylene glycol monomethyl ether (6 mL) were added to a 25 mL single-necked flask with a magnetic stirrer and a condensing tube, stirred and dissolved. A solution of hydrogen chloride in isopropanol (1.41 mmol, 0.28 mL, 5 M) was added dropwise. The mixture was heated to 120° C. under a nitrogen atmosphere and stirred to react overnight at this temperature. After cooling to room temperature, water (10 mL) and saturated sodium bicarbonate (5 mL) were added to the mixture. The mixture was extracted with dichloromethane (15 mL×3). The organic phases were combined, washed with saturated brine, dried over anhydrous sodium sulfate, filtered, concentrated and separated by silica gel column to give 150 mg of a white solid in a yield of 50.3%. LC-MS (APCI): m/z=529.2 (M+1)$^+$. $^1$H NMR (500 MHz, CDCl$_3$) δ/ppm: 8.11 (s, 1H), 7.90 (dd, J=8.0 Hz, J=1.0 Hz, 1H), 7.57 (d, J=8.0 Hz, 1H), 7.41-7.38 (m, 3H), 6.91 (d, J=8.0 Hz, 1H), 6.81 (s, 1H), 6.44 (s, 1H), 4.75 (s, 1H), 4.13 (t, J=6.0 Hz, 2H), 2.94 (t, J=6.0 Hz, 2H), 2.69-2.64 (m, 4H), 1.85-1.81 (m, 4H), 1.22 (s, 9H).

Example 3 Preparation of 3-((5-methyl-2-((4-(2-(pyrrolidin-1-yl)ethoxy)phenyl)amino)pyrimidin-4-yl)amino)-N-(2-methylpropan-2-yl-1,1,1,3,3,3-d$_6$)benzenesulfonamide (Compound T-3)

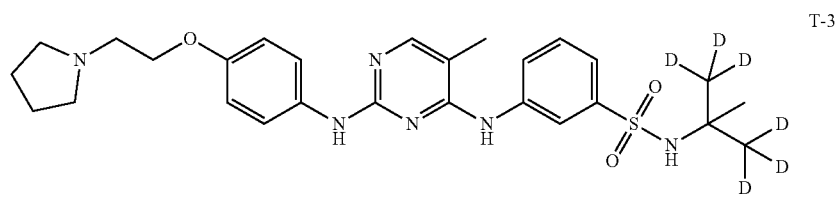 [SMILES: [2H]C([2H])([2H])C(C)(NS(=O)(=O)c1cccc(Nc2nc(Nc3ccc(OCCN4CCCC4)cc3)ncc2C)c1)C([2H])([2H])[2H]]

The synthesis was carried out using the following route:

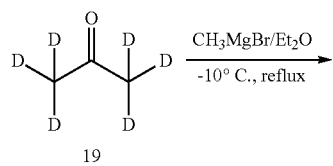

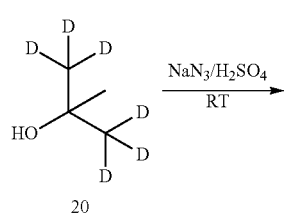

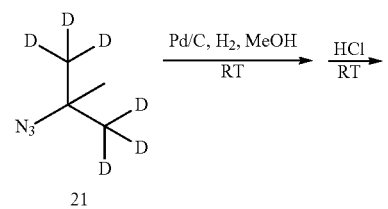

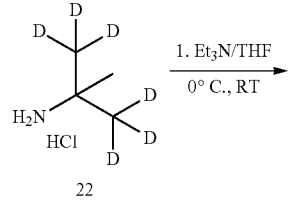

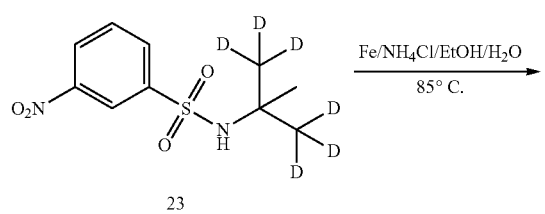

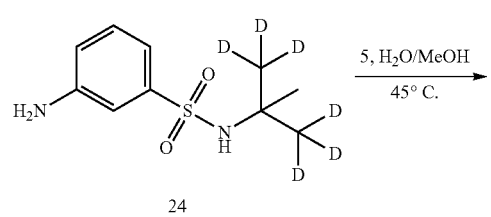

Step 1 Synthesis of Compound 20

Compound 19 (4.0 g, 62.39 mmol) and diethyl ether (40 mL) were added sequentially to a 100 mL three-necked flask with a magnetic stirrer and a condensing tube. The mixture was cooled to −10° C. under a nitrogen atmosphere, and methyl magnesium bromide (20.80 mL, 62.39 mmol, 3 M) was slowly added dropwise at this temperature. After completion of the dropwise addition, the mixture was slowly warmed to room temperature and then heated to reflux for 2 hours. After cooling to room temperature, the reaction was quenched by dropwise addition of saturated aqueous NH₄Cl (10 mL) in an ice water bath. The mixture was stirred for 10 minutes and then the layers were separated. The aqueous layer was extracted with diethyl ether (20 mL×2). The organic phases were combined, dried over anhydrous sodium sulfate, filtered, and then carefully distilled under reduced pressure at room temperature to give 1.7 g of a colorless liquid in a yield of 33.99%, which was directly used in the next step.

Step 2 Synthesis of Compound 21

Under an ice water bath, concentrated sulfuric acid (10 g) was slowly added dropwise to water (10 g), the temperature was controlled to no higher than 5° C., and sodium azide (1.52 g, 23.33 mmol) was slowly added in portions. The mixture was stirred and dissolved. Compound 20 (1.7 g, 21.21 mmol) was added. The reaction was stirred at room temperature under a nitrogen atmosphere overnight. Diethyl ether (20 mL) was added, and the mixture was stood to allow the layers to be separated. The upper organic phase was separated. The lower layer was again extracted with diethyl ether (20 mL). The organic phases were combined, washed with saturated NaHCO₃ (5 mL), dried over anhydrous sodium sulfate, and carefully evaporated to remove the solvent at room temperature to give 1.2 g of a yellow liquid in a yield of 53.80%, which was directly used in the next step.

Step 3 Synthesis of Compound 22

Compound 21 (1.2 g, 11.41 mmol) and methanol (20 mL) were added to a 50 mL single-necked flask with a magnetic stirrer, stirred and dissolved. Pd/C (120 mg, 10%) was added. The atmosphere was vacuumed and replaced with hydrogen under a hydrogen balloon for three times. The reaction was carried out overnight under a hydrogen atmosphere. The catalyst was filtered off. A solution of hydrogen chloride in isopropanol (5 M) was slowly added dropwise to adjust the pH to about 2, and stirred for 10 minutes. The solvent was evaporated under reduced pressure to give 1.04 g of a yellow solid in a yield of 79.23%, which was directly used in the next step.

Step 4 Synthesis of Compound 23

Compound 1 (2.0 g, 9.02 mmol) and THF (30 mL) were sequentially added to a 50 mL one-neck flask with a magnetic stirrer, and the mixture was stirred and dissolved. Compound 22 (1.04 g, 9.02 mmol) and triethylamine (3.65 g, 36.08 mmol) were slowly added dropwise in an ice water bath. After the addition, the ice water bath was removed, and the reaction was stirred at room temperature for 1 hour under a nitrogen atmosphere. The organic solvent was evaporated under reduced pressure. To the resulting residue was added water (50 mL). The mixture was extracted with dichloromethane (50 mL×3). The organic phases were combined, washed with saturated brine, dried over anhydrous sodium sulfate, filtered, concentrated and separated by silica gel column chromatography to give 700 mg of a white solid in a yield of 29.34%. LC-MS (APCI): m/z=265.1 (M+1)⁺. ¹H NMR (500 MHz, CDCl₃) δ 8.75 (t, J=2.0 Hz, 1H), 8.40 (dd, J=8.0 Hz, J=2.0 Hz, 1H), 8.24 (dd, J=8.0 Hz, J=2.0 Hz, 1H), 7.73 (t, J=8.0 Hz, 1H), 4.99 (s, 1H), 1.27 (s, 3H).

Step 5 Synthesis of Compound 24

Ethanol/water mixture (15 mL, 2/1) and compound 23 (300 mg, 1.17 mmol) were added to a 50 mL single-necked flask with a magnetic stirrer and a condensing tube. Reduced iron powder (651 mg, 11.67 mmol) and ammonium chloride (0.31 mg, 5.83 mmol) were added with stirring. The mixture was heated to 85° C. under a nitrogen atmosphere and stirred to react for 1 h at this temperature. After cooling to room temperature, insoluble solid was filtered off, and the organic solvent was evaporated under reduced pressure. To the resulting residue was added saturated aqueous NaHCO₃ (5 mL), and the mixture was extracted with ethyl acetate (20 mL×3). The organic phases were combined, dried over anhydrous sodium sulfate, filtered, and concentrated to give 250 mg of a white solid in a yield of 95.79%. LC-MS (APCI): m/z=235.1 (M+1)⁺.

Step 6 Synthesis of Compound 25

Compound 24 (200 mg, 1.23 mmol) and methanol/water mixture (15 mL, 1/1) were sequentially added to a 50 mL single-necked flask with a magnetic stirrer at room temperature, stirred and dissolved. Compound 5 (250 mg, 1.10 mmol) was added to the mixture. The reaction mixture was heated to 45° C. under a nitrogen atmosphere and stirred to react overnight at this temperature. After cooling to room temperature, a large amount of white solid was precipitated, which was filtered. The filter cake was washed with methanol/water (3.4 mL/4.0 mL), dried by suction, and dried under vacuum at 50° C. to give 230 mg of a white solid in a yield of 52.83%. LC-MS (APCI): m/z=361.1 (M+1)⁺. ¹H NMR (500 MHz, DMSO-d₆) δ9.11 (s, 1H), 8.11-8.09 (m, 2H), 7.88-7.86 (m, 1H), 7.55-7.52 (m, 3H), 2.18 (s, 3H), 1.12 (s, 3H).

Step 7 of Synthesis of Compound T-3

Compound 25 (200 mg, 0.56 mmol), Compound 18 (107 mg, 0.51 mmol) and ethylene glycol monomethyl ether (6 mL) were added to a 25 mL single-necked flask with a magnetic stirrer and a condensing tube, stirred and dissolved. A solution of hydrogen chloride in isopropanol (1.41 mmol, 0.28 mL, 5 M) was added dropwise. The mixture was heated to 120° C. under a nitrogen atmosphere and stirred to react overnight at this temperature. After cooling to room temperature, water (10 mL) and saturated sodium bicarbonate (5 mL) were added. The mixture was extracted with dichloromethane (15 mL×3). The organic phases were combined, washed with saturated brine, dried over anhydrous sodium sulfate, filtered, and concentrated. The residue was separated by silica gel column to give 150 mg of a white solid in a yield of 50.3%. LC-MS (APCI): m/z=531.2 (M+1)⁺. ¹H NMR (300 MHz, CDCl₃) δ8.11 (s, 1H), 7.92-7.89 (m, 2H), 7.57 (d, J=8.1 Hz, 1H), 7.41-7.38 (m, 3H), 6.91 (d, J=8.1 Hz, 1H), 6.81 (s, 1H), 6.44 (s, 1H), 4.60 (s, 1H), 4.13 (t, J=6.0 Hz, 2H), 2.94 (t, J=6.0 Hz, 2H), 2.69-2.64 (m, 4H), 2.13 (s, 3H), 1.85-1.81 (m, 4H), 1.22 (s, 3H).

Example 4 Preparation of 3-((5-methyl-2-((4-(2-(pyrrolidin-1-yl)ethoxy)phenyl)amino)pyrimidin-4-yl)amino)-N-(2-(methyl-d$_3$)propan-2-yl-1,1,1,3,3,3-d$_6$)benzenesulfonamide (Compound T-4)

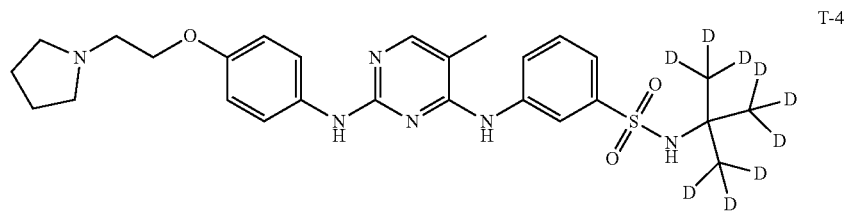 [SMILES: [2H]C([2H])([2H])C(NS(=O)(=O)c1cccc(Nc2nc(Nc3ccc(OCCN4CCCC4)cc3)ncc2C)c1)(C([2H])([2H])[2H])C([2H])([2H])[2H]]

The synthesis was carried out using the following route:

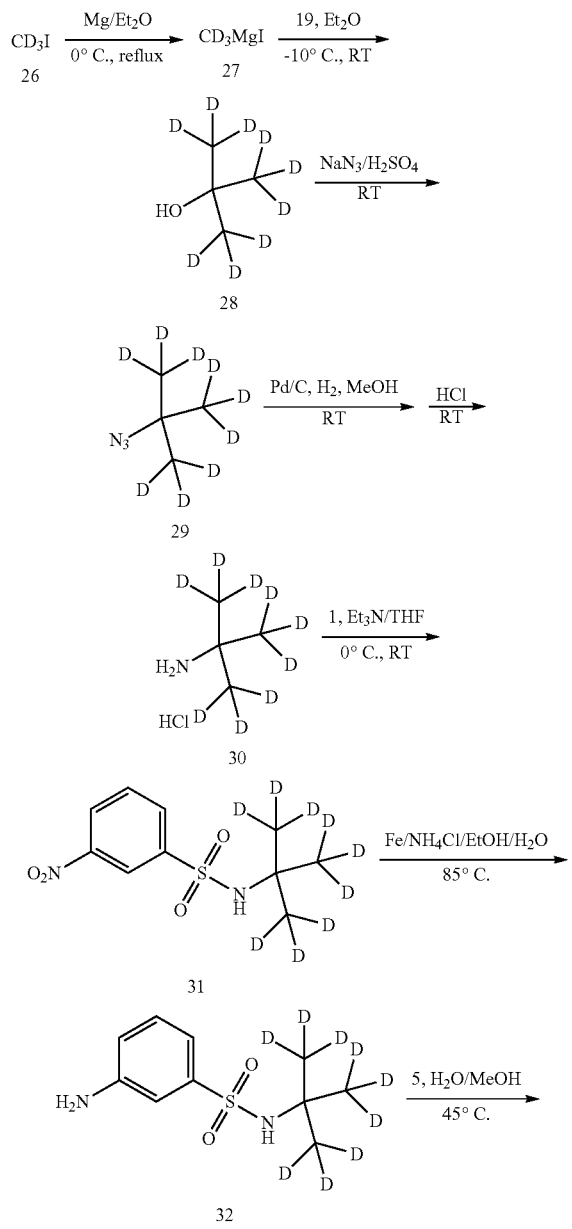

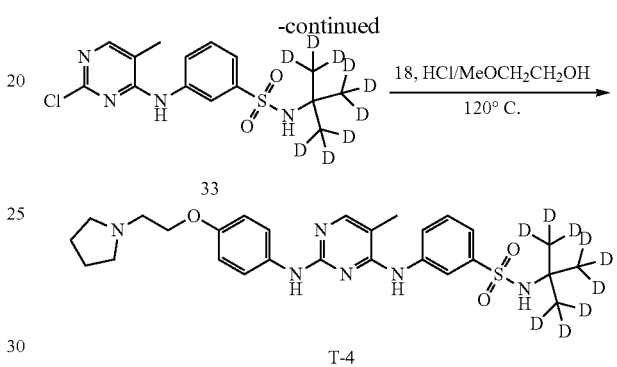

Step 1 Synthesis of Compound 28

Magnesium powder (1.80 g, 74.87 mmol) was added to a 100 mL three-necked flask equipped with a magnetic stirrer and a condensing tube. The atmosphere was vacuumed and replaced with nitrogen for three times. Diethyl ether (30 mL) and CD$_3$I (10.0 g, 68.96 mmol) were added under a nitrogen atmosphere. After the dropwise addition, the mixture was heated to reflux for 2 hours. After cooling to −10° C., a solution of compound 19 (4.0 g, 62.39 mmol) in diethyl ether (10 mL) was added dropwise. After the dropwise addition, the mixture was slowly warmed to room temperature and then heated to reflux for 2 hours. After cooling to room temperature, the reaction was quenched by dropwise addition of saturated aqueous saturated aqueous NH$_4$Cl (10 mL) in an ice water bath. The mixture was stirred for 10 min and then layers were separated. The aqueous layer was extracted with diethyl ether (20 mL×2). The organic phases were combined, dried over anhydrous sodium sulfate, filtered and then carefully distilled under reduced pressure at room temperature to give 1.7 g of a colorless liquid in a yield of 33.99%, which was directly used in the next step.

Step 2 Synthesis of Compound 29

Under an ice water bath, concentrated sulfuric acid (10 g) was slowly added dropwise to water (10 g), the temperature was controlled to no higher than 5° C., and sodium azide (1.52 g, 23.33 mmol) was slowly added in portions. The mixture was stirred and dissolved, and Compound 28 (1.7 g, 21.21 mmol) was added. The reaction was stirred at room temperature under a nitrogen atmosphere overnight. Diethyl ether (20 mL) was added, and the mixture was stood to allow the layers be separated. The upper organic phase was separated. The lower layer was again extracted with diethyl ether (20 mL). The organic phases were combined, washed with saturated NaHCO$_3$ (5 mL), dried over anhydrous sodium sulfate, and carefully evaporated to remove the solvent at room temperature to give 1.2 g of a yellow liquid in a yield of 53.80%, which was directly used in the next step.

Step 3 Synthesis of Compound 30

Compound 29 (1.2 g, 11.41 mmol) and methanol (20 mL) were added to a 50 mL single-necked flask with a magnetic stirrer, stirred and dissolved. Pd/C (120 mg, 10%) was added. The atmosphere was vacuumed and replaced with hydrogen under a hydrogen balloon for three times. The reaction was carried out overnight under a hydrogen atmosphere. The catalyst was filtered off. A solution of hydrogen chloride in isopropanol (5 M) was slowly added dropwise to adjust the pH to about 2. The mixture was stirred for 10 minutes. The solvent was evaporated under reduced pressure to give 1.04 g of a yellow solid in a yield of 79.23%, which was directly used in the next step.

Step 4 Synthesis of Compound 31

Compound 1 (2.0 g, 9.02 mmol) and THF (30 mL) were sequentially added to a 50 mL single-necked flask with a magnetic stirrer, and the mixture was stirred and dissolved. Compound 30 (1.04 g, 9.02 mmol) and triethylamine (3.65 g, 36.08 mmol) were slowly added dropwise in an ice water bath. After the addition, the ice water bath was removed, and the reaction was stirred at room temperature for 1 hour under a nitrogen atmosphere. The organic solvent was evaporated under reduced pressure. To the resulting residue was added water (50 mL). The mixture was extracted with dichloromethane (50 mL×3). The organic phases were combined, washed with saturated brine, dried over anhydrous sodium sulfate, filtered, concentrated and separated by silica gel column chromatography to give 700 mg of a white solid in a yield of 29.34%. LC-MS (APCI): m/z=268.1 (M+1)$^+$. $^1$H NMR (500 MHz, CDCl$_3$) δ8.75 (t, J=2.0 Hz, 1H), 8.40 (dd, J=8.0 Hz, J=2.0 Hz, 1H), 8.24 (dd, J=8.0 Hz, J=2.0 Hz, 1H), 7.73 (t, J=8.0 Hz, 1H), 4.99 (s, 1H).

Step 5 Synthesis of Compound 32

Ethanol/water mixture (15 mL, 2/1) and Compound 31 (300 mg, 1.17 mmol) were added to a 50 mL single-necked flask equipped with a magnetic stirrer and a condensing tube. Reduced iron powder (651 mg, 11.67 mmol) and ammonium chloride (0.31 mg, 5.83 mmol) were added with stirring. The mixture was heated to 85° C. under a nitrogen atmosphere and stirred to react for 1 h at this temperature. After cooling to room temperature, insoluble solid was filtered off, and the organic solvent was evaporated under reduced pressure. To the resulting residue was added saturated aqueous NaHCO$_3$ (5 mL), and the mixture was extracted with ethyl acetate (20 mL×3). The organic phases were combined, dried over anhydrous sodium sulfate, filtered, and concentrated to give 250 mg of a white solid in a yield of 95.79%. LC-MS (APCI): m/z=238.1 (M+1)$^+$.

Step 6 Synthesis of Compound 33

Compound 32 (200 mg, 1.23 mmol) and methanol/water mixture (15 mL, 1/1) were sequentially added to a 50 mL single-necked flask with a magnetic stirrer at room temperature, stirred and dissolved. Compound 5 (250 mg, 1.10 mmol) was added to the mixture. The reaction mixture was heated to 45° C. under nitrogen and stirred to react overnight at this temperature. After cooling to room temperature, a large amount of a white solid was precipitated, which was filtered. The filter cake was washed with methanol/water (3.4 mL/4.0 mL), dried by suction, and dried under vacuum at 50° C. to give 230 mg of a white solid in a yield of 52.83%. LC-MS (APCI): m/z=364.1 (M+1)$^+$. $^1$H NMR (500 MHz, DMSO-d$_6$) δ9.11 (s, 1H), 8.11-8.09 (m, 2H), 7.88-7.86 (m, 1H), 7.55-7.52 (m, 3H), 2.18 (s, 3H).

Step 7 Synthesis of Compound T-4

Compound 33 (200 mg, 0.56 mmol), Compound 18 (107 mg, 0.51 mmol) and ethylene glycol monomethyl ether (6 mL) were added to a 25 mL single-necked flask with a magnetic stirrer and a condensing tube. The mixture was stirred and dissolved. A solution of hydrogen chloride in isopropanol (1.41 mmol, 0.28 mL, 5 M) was added dropwise. The mixture was heated to 120° C. under a nitrogen atmosphere and stirred to react overnight at this temperature. After cooling to room temperature, water (10 mL) and saturated sodium bicarbonate (5 mL) were added. The mixture was extracted with dichloromethane (15 mL×3). The organic phases were combined, washed with saturated brine, dried over anhydrous sodium sulfate, filtered, and concentrated. The residue was separated by silica gel column to give 150 mg of a white solid in a yield of 50.3%. LC-MS (APCI): m/z=534.2 (M+1)$^+$. $^1$H NMR (300 MHz, CDCl$_3$) δ8.11 (s, 1H), 7.92-7.89 (m, 2H), 7.57 (d, J=8.1 Hz, 1H), 7.41-7.38 (m, 3H), 6.91 (d, J=8.1 Hz, 1H), 6.81 (s, 1H), 6.44 (s, 1H), 4.60 (s, 1H), 4.13 (t, J=6.0 Hz, 2H), 2.94 (t, J=6.0 Hz, 2H), 2.69-2.64 (m, 4H), 2.13 (s, 3H), 1.85-1.81 (m, 4H).

Example 5 Preparation of N-(tert-butyl)-3-((5-methyl-2-((4-(2-(pyrrolidin-1-yl-d$_8$)ethoxy)phenyl)amino)pyrimidin-4-yl)amino)benzenesulfonamide (Compound T-5)

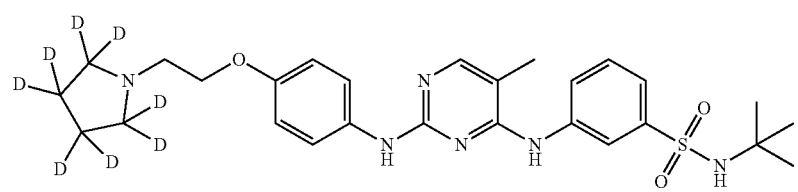

T-5

The synthesis was carried out using the following route:

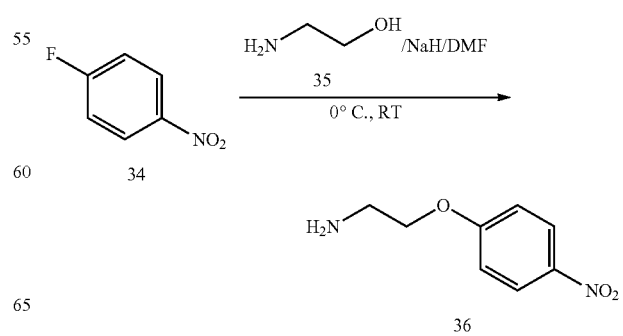

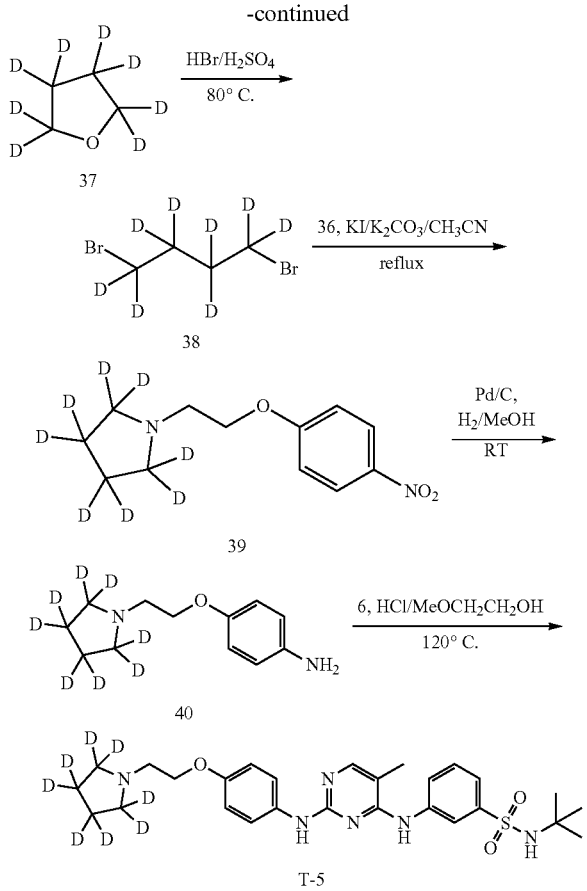

Step 1 Synthesis of Compound 36

NaH (595 mg, 14.88 mmol, 60%) was added to a 50 mL three-necked flask with a magnetic stirrer. The atmosphere was vacuumed and replaced with hydrogen under nitrogen for three times. Under a nitrogen atmosphere, anhydrous THF (20 mL) was added to the mixture. A solution of 2-ethanolamine (909 mg, 14.88 mmol) in anhydrous THF (2 mL) was added dropwise under an ice-water bath. The reaction was stirred for 10 minutes. Then a solution of Compound 34 (2.0 g, 14.17 mmol) in anhydrous THF (3 mL) was added. After the addition, the ice water bath was removed, and the reaction was stirred at room temperature for 2 hours. The reaction was quenched by the addition of saturated aqueous ethyl acetate (50 mL) and filtered. The filtrate was dried over anhydrous sodium sulfate, filtered, concentrated and separated by silica gel column to give 1.6 g of a yellow oil in a yield of 61.69%. LC-MS (APCI): m/z=183.1 (M+1)$^+$. $^1$H NMR (300 MHz, CDCl$_3$) δ8.21 (d, J=9.3 Hz, 2H), 6.97 (d, J=9.3 Hz, 2H), 4.09 (t, J=5.1 Hz, 2H), 3.15 (t, J=5.1 Hz, 2H).

Step 2 Synthesis of Compound 38

An aqueous hydrobromic acid solution (7.57 g, 93.57 mmol, 48%) and concentrated sulfuric acid (3.67 g) were added to a 50 mL one-necked flask equipped with a magnetic stirrer and a condensing tube in an ice water bath, and stirred well. Compound 37 (3.0 g, 37.43 mmol) was added dropwise. After completion, the reaction mixture was heated to 90° C. and stirred to react for 2 hours at this temperature. After cooling to room temperature, the mixture was extracted with ethyl acetate (20 mL×2). The organic phases were combined, dried over anhydrous sodium sulfate, concentrated and separated by silica gel column to give 1.5 g of an anhydrous oil in a yield of 17.89%.

Step 3 Synthesis of Compound 39

Compound 36 (420 mg, 2.31 mmol), Compound 38 (640 mg, 2.86 mmol) and acetonitrile (15 mL) were added to a 50 mL single-necked flask with a magnetic stirrer and a condensing tube, stirred and dissolved. Potassium iodide (76 mg, 0.46 mmol) and potassium carbonate (382 mg, 2.77 mmol) were added. The reaction mixture was heated to reflux under a nitrogen atmosphere and then allowed to react overnight at this temperature. After cooling to room temperature, the solvent was evaporated under reduced pressure. Water (15 mL) and ethyl acetate (20 mL) were added. The organic layer was separated. The aqueous layer was extracted with ethyl acetate (20 mL×2). The organic phases were combined, dried over anhydrous sodium sulfate, filtered, concentrated and separated by silica gel column to give 250 mg of a yellow oil in a yield of 44.2%. LC-MS (APCI): m/z=245.1 (M+1)$^+$. $^1$H NMR (300 MHz, CDCl$_3$) δ8.20 (d, J=9.0 Hz, 2H), 6.98 (d, J=9.0 Hz, 2H), 4.21 (t, J=6.0 Hz, 2H), 2.96 (t, J=6.0 Hz, 2H).

Step 4 Synthesis of Compound 40

Compound 39 (250 mg, 1.04 mmol) and methanol (10 mL) were added to a 50 mL single-necked flask with a magnetic stirrer, stirred and dissolved. Pd/C (25 mg, 10%) was added. The atmosphere was vacuumed and replaced with hydrogen under a hydrogen balloon for three times. The reaction was carried out overnight under a hydrogen atmosphere. The catalyst was filtered off, and the filter cake was washed with methanol (3 mL). The filtrates were combined and concentrated to give 220 mg of a yellow oil in a yield of 98.6%. LC-MS (APCI): m/z=215.1 (M+1)$^+$.

Step 5 Synthesis of Compound T-5

Compound 40 (200 mg, 0.56 mmol), Compound 6 (107 mg, 0.51 mmol) and ethylene glycol monomethyl ether (6 mL) were added to a 25 mL single-necked flask with a magnetic stirrer and a condensing tube, stirred and dissolved. A solution of hydrogen chloride in isopropanol (1.41 mmol, 0.28 mL, 5 M) was added dropwise. The mixture was heated to 120° C. under a nitrogen atmosphere and stirred to react overnight at this temperature. After cooling to room temperature, water (10 mL) and saturated sodium bicarbonate (5 mL) were added. The mixture was extracted with dichloromethane (15 mL×3). The organic phases were combined, washed with saturated brine, dried over anhydrous sodium sulfate, filtered, and concentrated. The residue was separated by silica gel column to give a white solid of 150 mg in a yield of 50.3%. LC-MS (APCI): m/z=533.2 (M+1)$^+$. $^1$H NMR (500 MHz, CDCl$_3$) δ8.11 (s, 1H), 7.92-7.89 (m, 2H), 7.57 (d, J=8.0 Hz, 1H), 7.41-7.38 (m, 3H), 6.91 (d, J=8.0 Hz, 1H), 6.81 (s, 1H), 6.44 (s, 1H), 4.60 (s, 1H), 4.13 (t, J=5.5 Hz, 2H), 2.94 (t, J=5.5 Hz, 2H), 2.13 (s, 3H), 1.22 (s, 9H).

Biological Activity Test (1) Kinase Inhibition

Reagents and Materials:

JAK2, JAK2/V617F, ATP (Sigma, Cat. No. A7699-1G), DMSO (Sigma, Cat. No. D2650), 96-well plate (Corning, Cat. No. 3365), 384-well plate (Greiner, Cat. No. 784076), HTRF Kinase TK Kit (Cisbio), 5×Kinase Buffer A (Life Technologies, Cat. No. PV3186), Kinase Tracer 199 (Life Technologies, Cat. No. PV5830), LanthaScreen® Eu-anti-GST Antibody (Life Technologies, Cat. No. PV5594).

Particular Experimental Method:

Formulation of Compound: The test compounds were dissolved in DMSO to make 20 mM stock solutions. Then, they were diluted with a 3-fold gradient dilution in DMSO for ten times. When using, they were diluted 10-fold with buffer.

JAK2 and JAK2 [V617F] Kinase Assay: In 5× Kinase Buffer A, JAK2 or JAK2 [V617F] kinase was mixed with pre-diluted compounds at different concentrations in duplicate for 10 minutes. The corresponding substrate and ATP were added and reacted at room temperature for 20 minutes (in which negative and positive controls were set: the negative control was a blank control and the positive control was erlotinib). After the reaction was completed, a detection reagent (the reagent in the HTRF Kinase TK kit) was added. After incubation at room temperature for 30 minutes, the enzyme activities in the presence of the compounds disclosed herein at each concentration were measured by an Evnvision microplate reader, and inhibitory activities of compounds at different concentrations on the enzyme activity were calculated. The inhibitory activities of compounds at different concentrations on enzyme activity were then fitted according to the four-parameter equation using Graphpad 5.0 software, and the $IC_{50}$ values were calculated.

The compounds disclosed herein and the non-deuterated compound Fedratinib were tested in the above kinase inhibition assay. The compounds disclosed herein were found to have more potent or comparable activities on JAK2 kinase and JAK2/V617F kinase. The results of inhibition of kinase by representative example compounds are summarized in Table 1 below.

TABLE 1

| Example compound | JAK2 $IC_{50}$ (nM) | JAK2/V617F $IC_{50}$ (nM) |
| --- | --- | --- |
| Fedratinib | 3.08 | 4.05 |
| T-1 | 3.16 | 4.06 |
| T-2 | 2.89 | 3.69 |
| T-3 | 3.06 | 3.78 |
| T-4 | 3.24 | 4.05 |
| T-5 | 3.47 | 4.55 |

(2) Cytotoxicity Assay

The inhibitory effects of example compounds on the activity of BaF3-EpoR-JAK2 and BaF3-EpoR-JAK2/V617F cells were determined.

Materials and reagents: RPMI-1640 medium (GIBCO, Cat. No. A10491-01), fetal bovine serum (GIBCO, Cat. No. 10099-141), antibiotics (GIBCO, Cat. No. 10010-031), IL-3 (CST, Cat. No. 8923SF), phosphate buffer solution PBS (GIBCO, Cat. No. 10010-0312), penicillin-streptomycin (GIBCO, Cat. No. 15140-122);

Cell lines: BaF3-EpoR-JAK2 cells (Pharmaron), BaF3-EpoR-JAK2/V617F cells (Pharmaron), live cell assay kit CellTiter-Glo4 (Promega, Cat. No. G7572), 96-well blackwall clear flat-bottom cell culture plate (Corning, Cat. No. 3340).

Assay method: 1. Preparation of cell plates. BaF3-EpoR-JAK2 cells and BaF3-EpoR-JAK2/V617F cells were seeded in 96-well plates, respectively, and 1 ng/ml IL-3 was added to Ba/F3 cells. The cell plates were placed in a carbon dioxide incubator for overnight culture. 2. The test compounds were dissolved in DMSO and subjected to 3-fold gradient dilution, 9 compound concentrations were obtained in duplicate. 3. Treatments of Cells with Compounds. The compounds were transferred to cell plates, and the starting concentration of the compounds was 10 µM. The cell plates were incubated in a carbon dioxide incubator for 3 days. 4. Detection. A CellTiter-Glo reagent was added to the cell plates and incubated for 30 minutes at room temperature to stabilize the luminescence signal. Reading was obtained using a PerkinElmer Envision multi-label analyzer.

The compounds disclosed herein and the non-deuterated compound Fedratinib were tested in the above cytotoxicity assay. The compounds disclosed herein were found to have more potent or comparable activities on BaF3-EpoR-JAK2 cells and BaF3-EpoR-JAK2/V617F cells. The results of in vitro inhibition of the proliferation of cancer cells by representative example compounds are summarized in Table 2 below.

TABLE 2

| Example compound | BaF3-EpoR-JAK2 cells $IC_{50}$ (nM) | BaF3-EpoR-JAK2/V617F cells $IC_{50}$ (nM) |
| --- | --- | --- |
| Fedratinib | 652.75 | 211.18 |
| T-1 | 535.86 | 205.93 |
| T-2 | 725.03 | 195.83 |
| T-3 | 603.63 | 243.63 |
| T-4 | 586.81 | 237.71 |
| T-5 | 689.79 | 269.36 |

(3) Metabolic Stability Evaluation

Microsomal experiment: human liver microsomes: 0.5 mg/mL, Xenotech; rat liver microsomes: 0.5 mg/mL, Xenotech; mouse liver microsomes: 0.5 mg/mL, Xenotech; coenzyme (NADPH/NADH): 1 mM, Sigma Life Science; magnesium chloride: 5 mM, 100 mM phosphate buffer (pH 7.4).

Preparation of a stock solution: A certain amount of the powder of the example compounds was accurately weighed and dissolved in DMSO to a 5 mM concentration.

Preparation of phosphate buffer (100 mM, pH 7.4): 150 mL of a pre-prepared 0.5 M potassium dihydrogen phosphate and 700 mL of a pre-prepared 0.5 M dipotassium hydrogen phosphate were mixed. The mixture was then adjusted to pH 7.4 with a 0.5 M dipotassium hydrogen phosphate solution. The mixture was diluted 5-fold with ultrapure water before use, and magnesium chloride was added to obtain a phosphate buffer (100 mM) containing 100 mM potassium phosphate, 3.3 mM magnesium chloride, and a pH of 7.4.

A solution of NADPH regeneration system (containing 6.5 mM NADP, 16.5 mM G-6-P, 3 U/mL G-6-P D, 3.3 mM magnesium chloride) was prepared and placed on wet ice before use.

Preparation of a stop solution: an acetonitrile solution containing 50 ng/mL propranolol hydrochloride and 200 ng/mL tolbutamide (internal standard). 25057.5 µL of phosphate buffer (pH 7.4) was added into a 50 mL centrifuge tube, 812.5 µL of human liver microsomes, rat liver microsomes and mouse liver microsomes were then added into the 50 mL centrifuge tube, respectively, and the mixtures were mixed evenly to obtain liver microsome dilutions with a protein concentration of 0.625 mg/mL. Incubation of samples: The stock solutions of the corresponding compounds were diluted to 0.25 mM with an aqueous solution containing 70% acetonitrile, respectively, and used as working solutions ready for use. 398 µL of dilutions of human liver microsomes or rat liver microsomes or mouse liver microsome were added to 96-well incubation plates (N=2), and then 2 µL of 0.25 mM working solutions were added and mixed, respectively.

Determination of metabolic stability: 300 µL of a pre-cooled stop solution was added to each well of a 96-well deep well plate and placed on ice as a stop plate. The 96-well incubation plate and the NADPH regeneration system were placed in a 37° C. water bath, shaken at 100 rpm, and pre-incubated for 5 min. 80 μL of an incubation solution was taken from each well of the incubation plate and added to the stop plate, mixed evenly, and replenished with 20 μL of NADPH regeneration system solution as a 0 min sample. 80 μL of NADPH regeneration system solution was then added to each well of the incubation plate to start the reaction, and timing was started. The corresponding compounds had a reaction concentration of 1 μM and the protein had a concentration of 0.5 mg/mL. 100 μL of the reaction solution was taken at 10, 30, and 90 min after reaction, respectively, added to the stop plate, and vortexed for 3 minutes to terminate the reaction. The stop plate was centrifuged for 10 min at 5000×g at 4° C. 100 μL of the supernatant was added to a 96-well plate to which 100 μL of distilled water was previously added, mixed evenly, and analyzed by LC-MS/MS.

Data analysis: The peak areas of the corresponding compounds and internal standard were detected by LC-MS/MS system, and the ratio of the peak areas of the compounds to the internal standard was calculated. The slope was measured by plotting the natural logarithm of the percent of remained compound versus time, and $t_{1/2}$ and $CL_{int}$ were calculated according to the formula below, where V/M is equal to 1/protein concentration.

$$t_{1/2} = -\frac{0.693}{\text{slope}}, \; CL_{int} = \frac{0.693}{t_{1/2}} \cdot \frac{V}{M}, \; t_{1/2}(\text{min}); \; CL_{int}(\mu L/\text{min/mg}).$$

The compounds disclosed herein and the non-deuterated compound Fedratinib were tested in the above metabolic stability evaluation experiment. The compounds disclosed herein were found to have a longer half-life, a lower clearance rate, and a more excellent metabolic stability. The metabolic stability results of representative example compounds are summarized in Table 3.

TABLE 3

| No. | Human liver microsome experiment | | Rat liver microsome experiment | | Mouse liver microsome experiment | |
| --- | --- | --- | --- | --- | --- | --- |
| | $t_{1/2}$ (min) | $CL_{int}$ (μL/min/mg) | $t_{1/2}$ (min) | $CL_{int}$ (μL/min/mg) | $t_{1/2}$ (min) | $CL_{int}$ (μL/min/mg) |
| Fedratinib | 111.3 | 12.5 | 17.0 | 81.3 | 5.8 | 237.5 |
| T-1 | 203.0 | 6.8 | 18.7 | 73.9 | 8.8 | 156.9 |
| T-2 | — | — | — | — | 8.0 | 174.3 |
| T-3 | — | — | 17.2 | 80.4 | 6.7 | 205.8 |
| T-4 | — | — | 18.1 | 76.6 | 7.1 | 194.0 |
| T-5 | 120.7 | 11.5 | 18.0 | 77.0 | 8.8 | 158.0 |

(4) Rat Pharmacokinetic Experiment 6 male Sprague-Dawley rats (7-8 weeks old, and weighted approximately 210 g) were divided into 2 groups with 3 rats in each group. The rats were intravenously or orally administered a single dose of compound (3 mg/kg intravenously, 10 mg/kg orally) to compare pharmacokinetic differences.

The rats were raised on standard food and water. Fasting was started 16 hours before the test. The drug was dissolved with PEG400 and dimethyl sulfoxide. The blood samples were collected from eyelids at the time points of 0.083 hours, 0.25 hours, 0.5 hours, 1 hour, 2 hours, 4 hours, 6 hours, 8 hours, 12 hours, and 24 hours after administration. Rats were briefly anesthetized after inhalation of diethyl ether and 300 μL of blood sample was collected from the eyelids into test tubes. There was 30 μL of 1% heparin salt solution in the test tube. Tubes were dried at 60° C. overnight before use. After the blood sample was collected at the last time point, the rats were sacrificed after ether anesthesia.

Immediately after the collection of the blood sample, the test tube was gently inverted at least 5 times to ensure sufficient mixing and then placed on ice. The blood sample was centrifuged at 5000 rpm at 4° C. for 5 minutes to separate the plasma from the red blood cells. 100 μL of plasma was aspirated into a clean plastic centrifuge tube with a pipette, marking with the name of the compound and time point. Plasma was stored at −80° C. prior to analysis. The concentration of the compound disclosed herein in plasma was determined by LC-MS/MS. The pharmacokinetic parameters were calculated based on the drug concentration in blood of each animal at different time points.

The compounds disclosed herein and the non-deuterated compound Fedratinib were tested in the above rat pharmacokinetic experiment. The compounds disclosed herein were found to have better oral availability. The oral availability results of the representative example compounds are summarized in Table 4.

TABLE 4

| Example compound | Fedratinib | T-5 |
| --- | --- | --- |
| Oral availability (%) | 7.24 | 7.48 |

The above content is a further detailed description of the present disclosure in combination with specific preferred embodiments, and it cannot be assumed that the specific implementation of the present disclosure is limited to these descriptions. For a person of ordinary skill in the art to which the present disclosure belongs, a number of simple deductions or substitutions can be made without departing from the concept of the present disclosure, and should all be considered as falling within the protection scope of the present disclosure.

What is claimed is:

1. A compound of Formula (I):

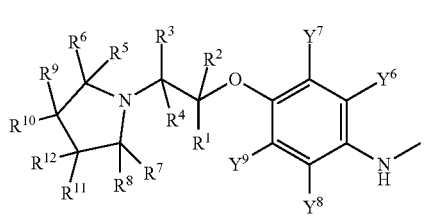

Formula (I)

-continued

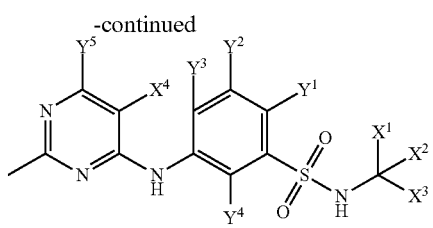

wherein,
$R^1, R^2, R^3, R^4, R^5, R^6, R^7, R^8, R^9, R^{10}, R^{11}, R^{12}, Y^1, Y^2, Y^3, Y^4, Y^5, Y^6, Y^7, Y^8$ and $Y^9$ are each independently selected from hydrogen or deuterium; and $X^1, X^2, X^3$, and $X^4$ are each independently selected from $CH_3$, $CD_3$, $CHD_2$, and $CH_2D$;

provided that if $X^1, X^2, X^3$, and $X^4$ are each $CH_3$, then at least one of $R^1, R^2, R^3, R^4, R^5, R^6, R^7, R^8, R^9, R^{10}, R^{11}, R^{12}, Y^1, Y^2, Y^3, Y^4, Y^5, Y^6, Y^7, Y^8$, and $Y^9$ is deuterium;

wherein the deuterium or D means a content of deuterium isotope in the deuterated position is more than 50%;

or a pharmaceutically acceptable salt, a prodrug, a hydrate or a solvate, a crystalline form, a N-oxide and various diastereoisomers thereof.

2. The compound of claim 1, which is a compound of Formula (II):

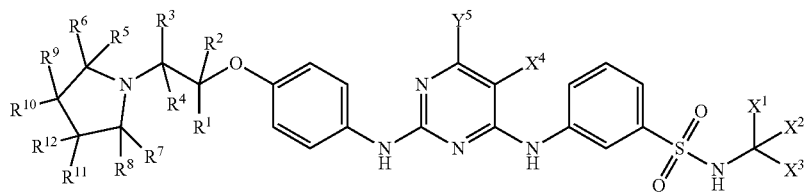

Formula (II)

wherein,
$R^1, R^2, R^3, R^4, R^5, R^6, R^7, R^8, R^9, R^{10}, R^{11}, R^{12}, Y^5, X^1, X^2, X^3$, and $X^4$ are as defined in claim 1;

or a pharmaceutically acceptable salt, a prodrug, a hydrate or a solvate, a crystalline form, a N-oxide and various diastereoisomers thereof.

3. The compound of claim 2, wherein $R^5, R^6, R^7, R^8, R^9, R^{10}, R^{11}$, and $R^{12}$ are deuterium.

4. The compound of claim 2, wherein $X^1, X^2$ and $X^3$ are $CD_3$.

5. The compound of claim 2, wherein $Y^5$ is deuterium and $X^4$ is $CD_3$.

6. The compound of claim 2, wherein $X^1$ and $X^3$ are $CD_3$.

7. The compound of claim 2, wherein $R^1, R^2, R^3$ and $R^4$ are deuterium.

8. The compound of claim 1, wherein the compound is selected from the group consisting of:

Formula (1)

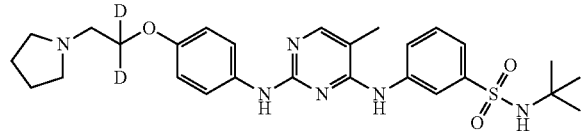

Formula (2)

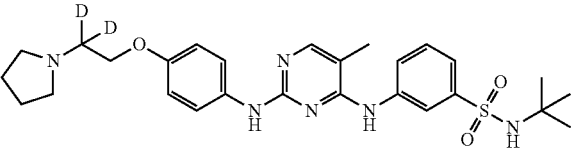

Formula (3)

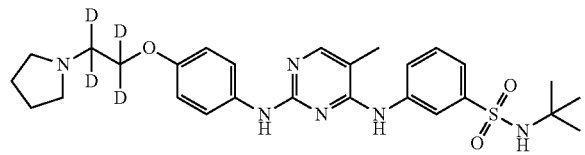

Formula (4)

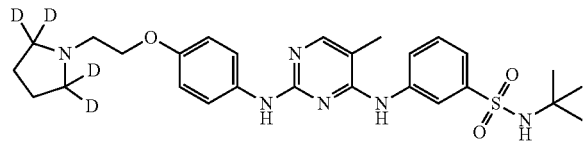

Formula (5)

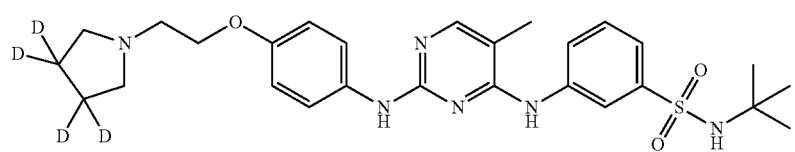

-continued
Formula (6)
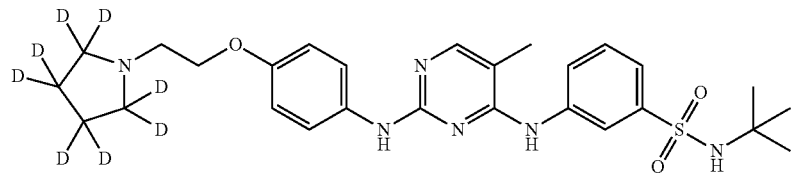
Formula (7)
Formula (8)
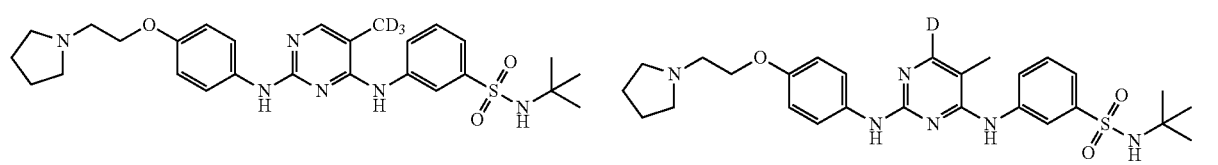
Formula (9)
Formula (10)
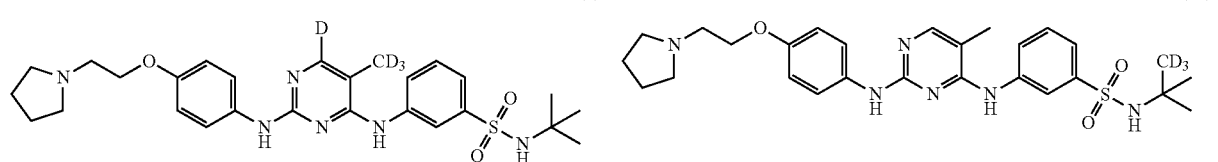
Formula (11)
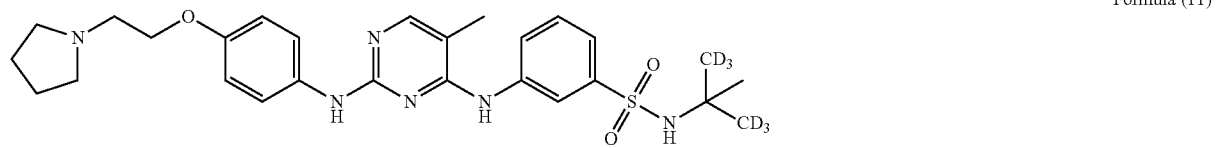
Formula (12)
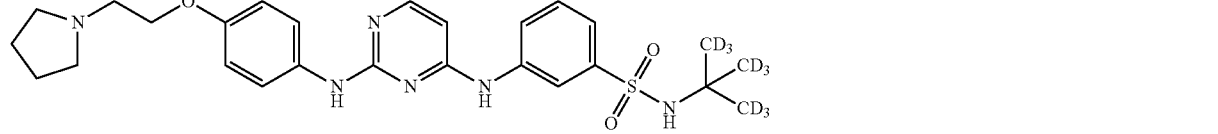
Formula (13)
Formula (14)
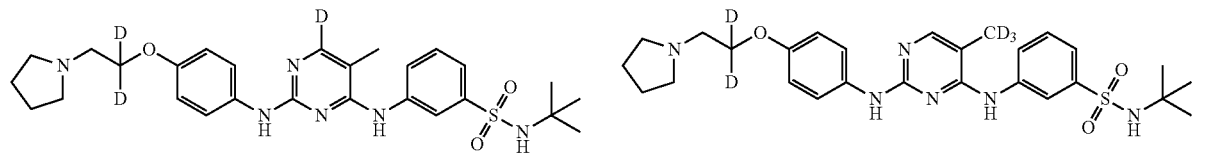
Formula (15)
Formula (16)
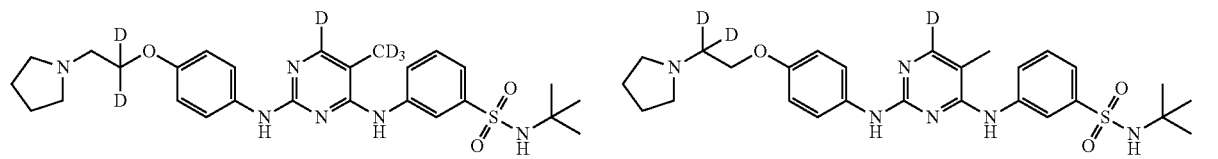
Formula (17)
Formula (18)
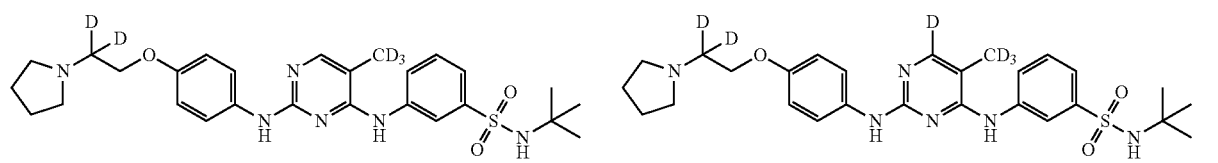
Formula (19)
Formula (20)
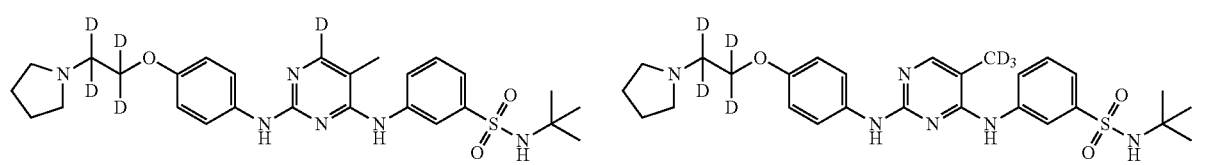

Formula (21)
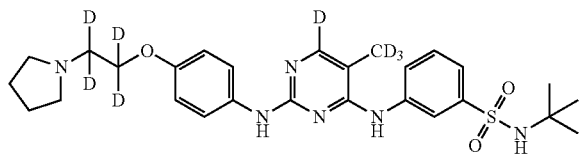
Formula (22)
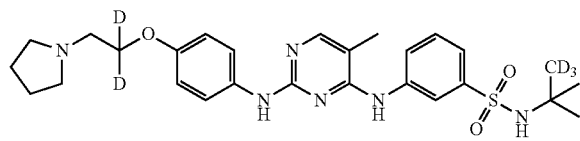
Formula (23)
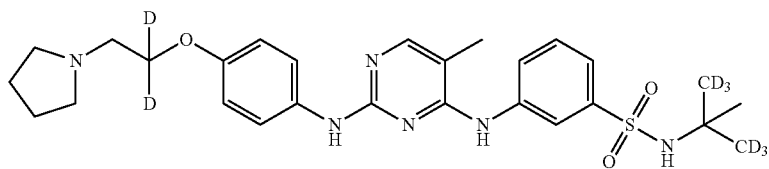
Formula (24)
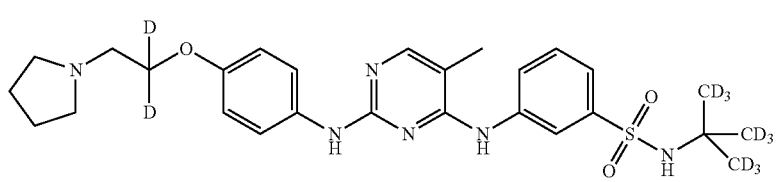
Formula (25)
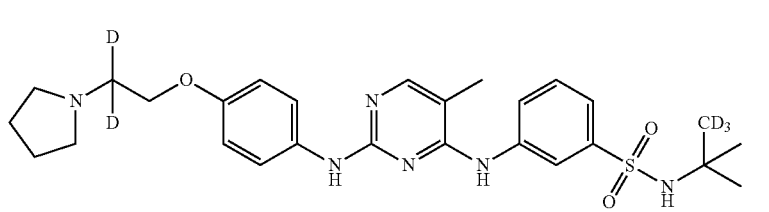
Formula (26)
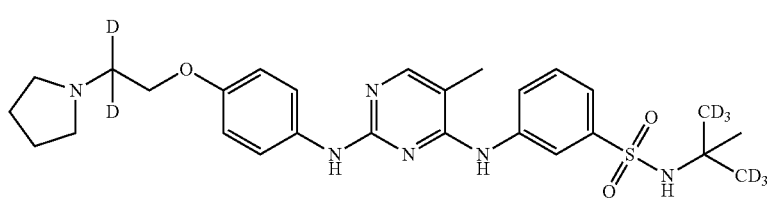
Formula (27)
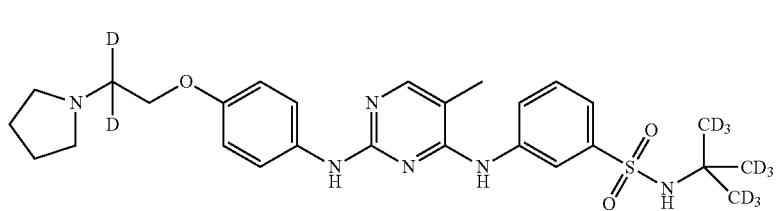
Formula (28)
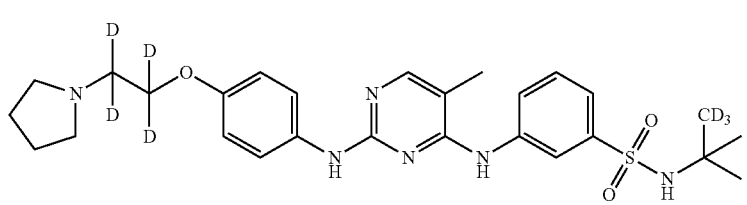
Formula (29)
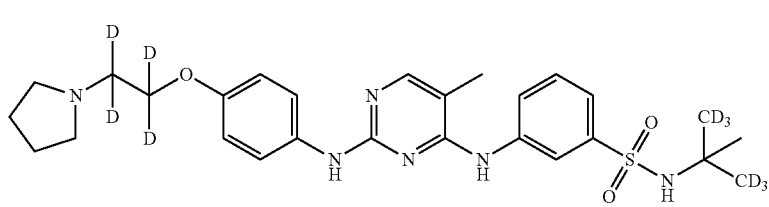

-continued
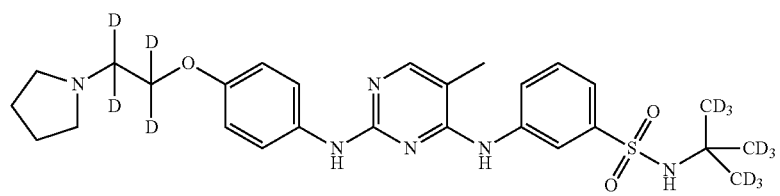
Formula (30)
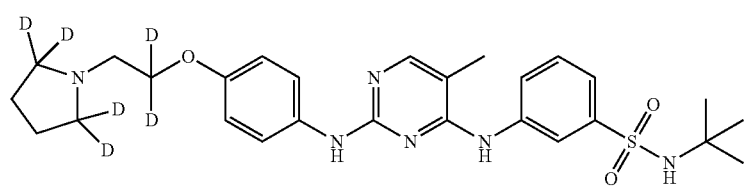
Formula (31)
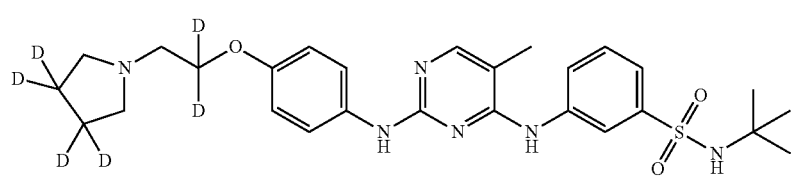
Formula (32)
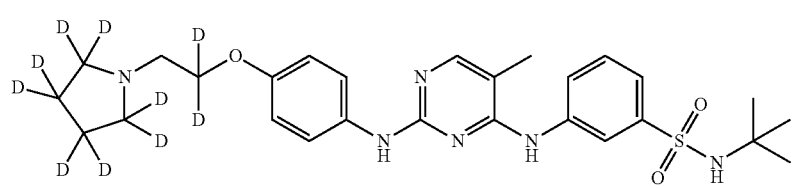
Formula (33)
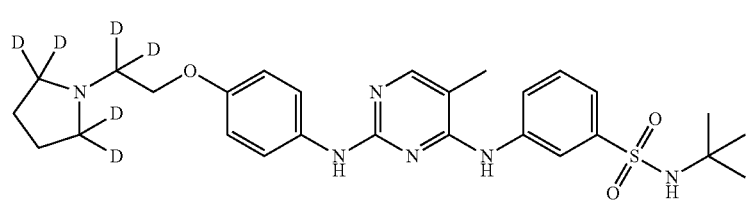
Formula (34)
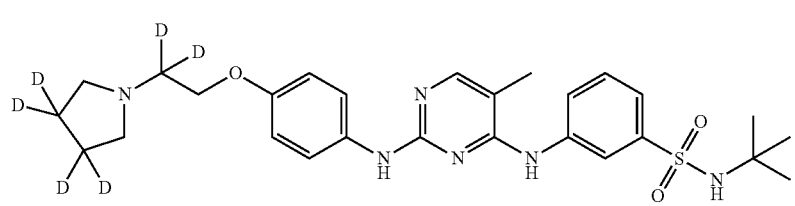
Formula (35)
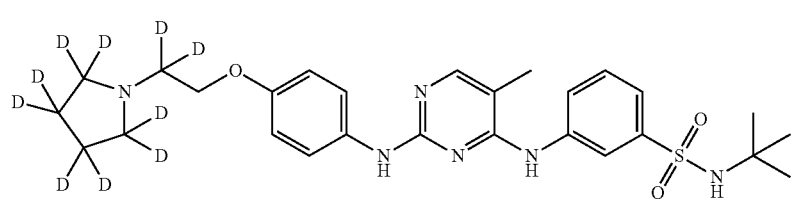
Formula (36)
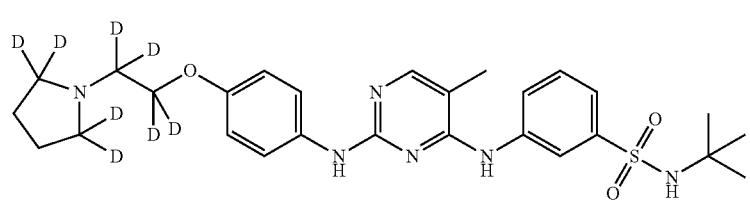
Formula (37)

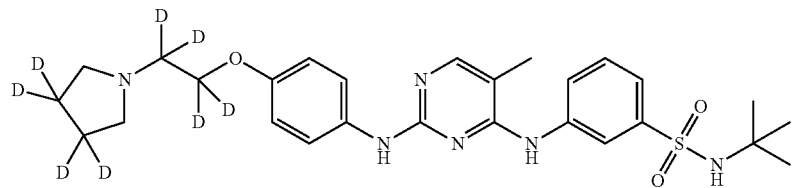
Formula (38)
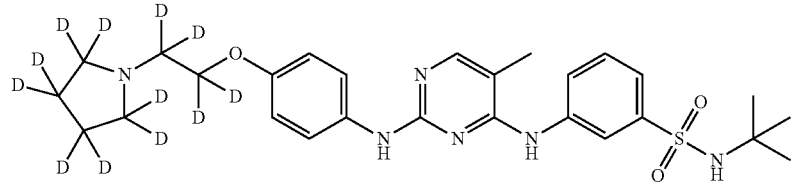
Formula (39)
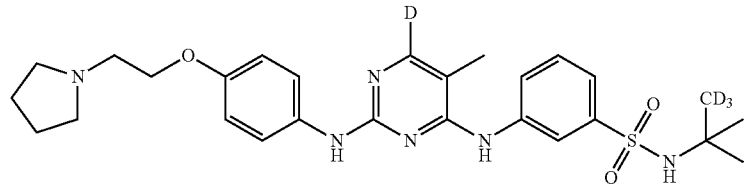
Formula (40)
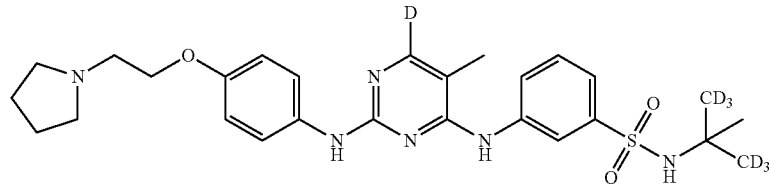
Formula (41)
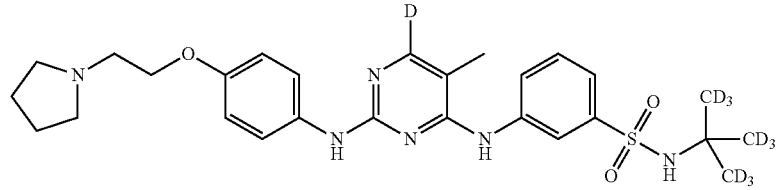
Formula (42)
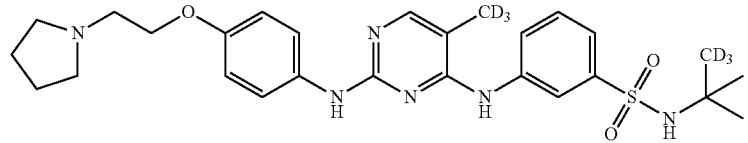
Formula (43)
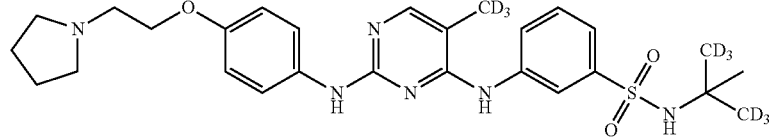
Formula (44)
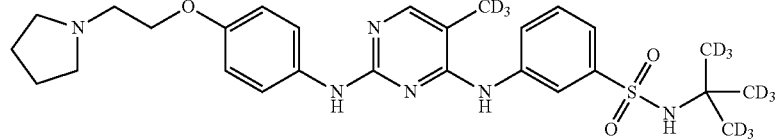
Formula (45)

-continued
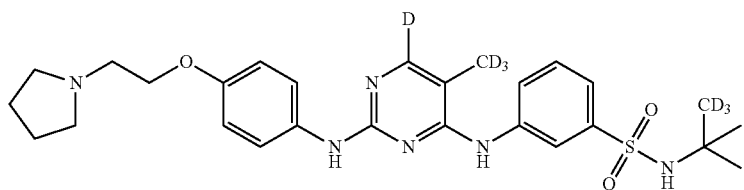
Formula (46)
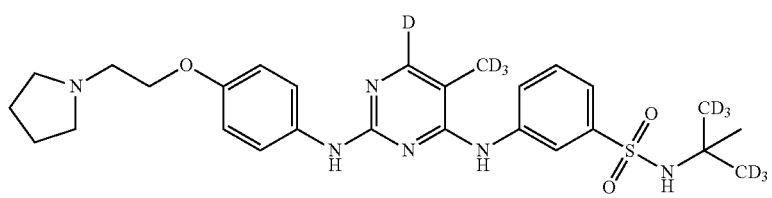
Formula (47)
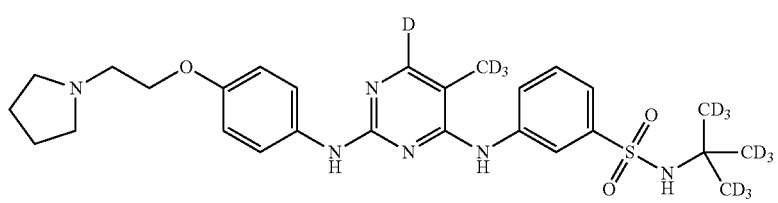
Formula (48)
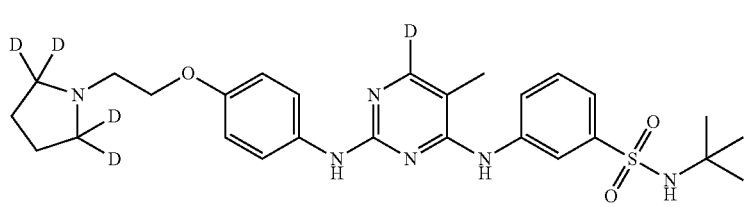
Formula (49)
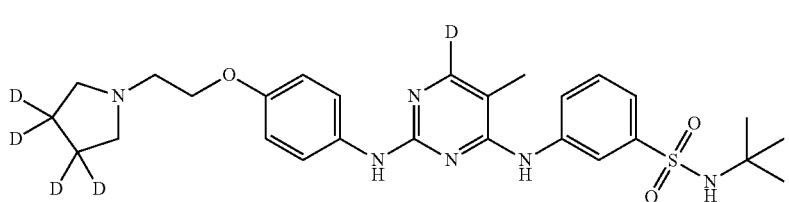
Formula (50)
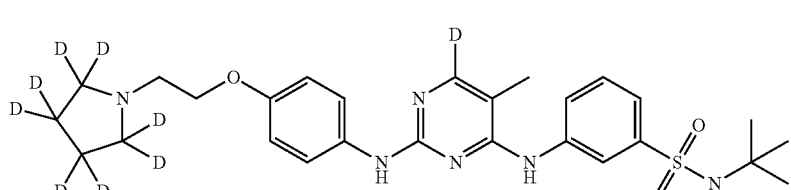
Formula (51)
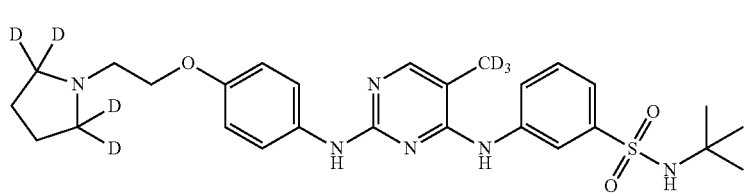
Formula (52)
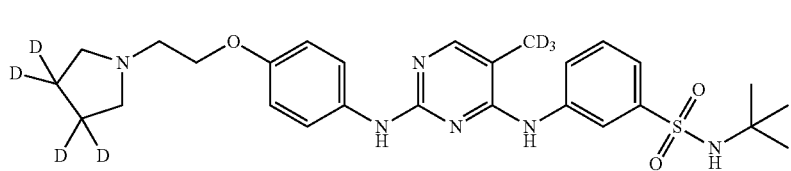
Formula (53)

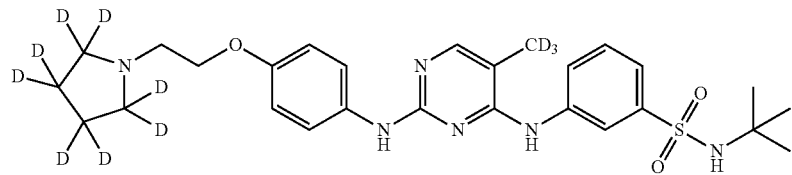
Formula (54)
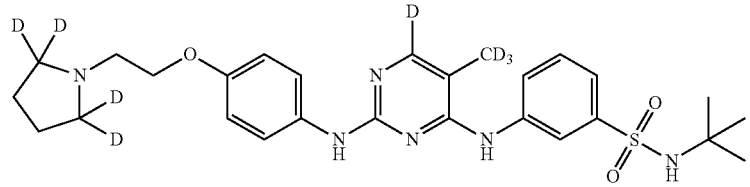
Formula (55)
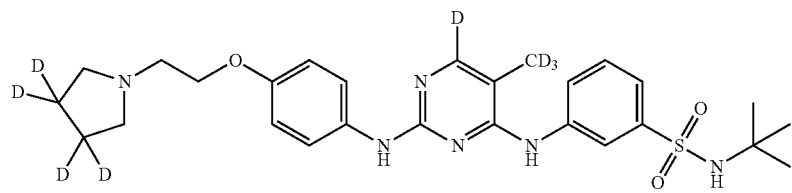
Formula (56)
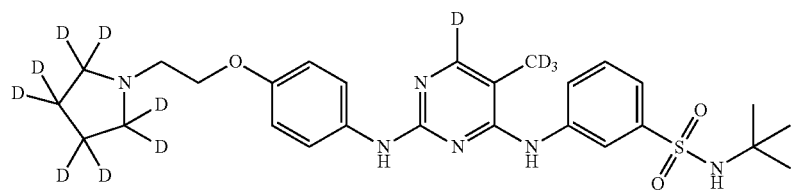
Formula (57)
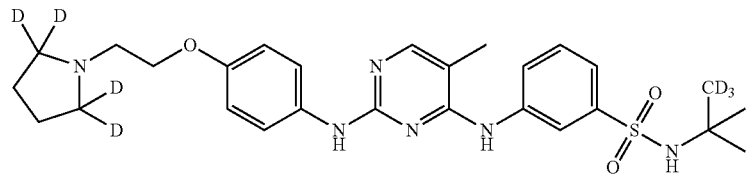
Formula (58)
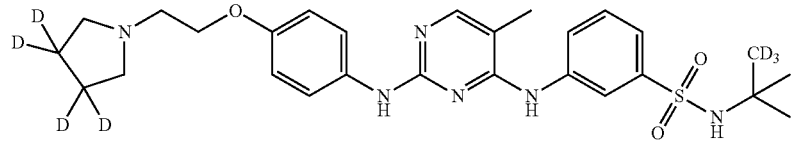
Formula (59)
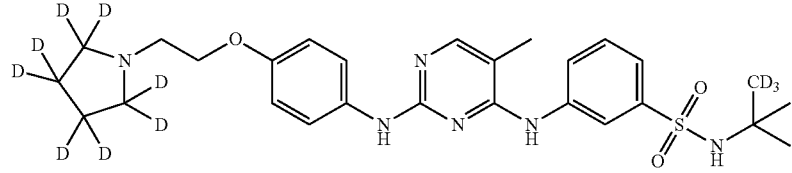
Formula (60)
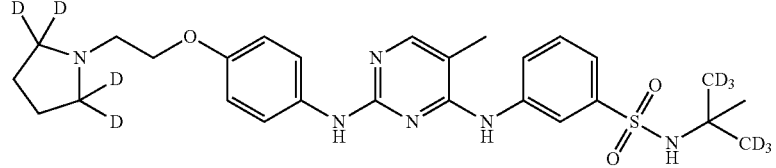
Formula (61)
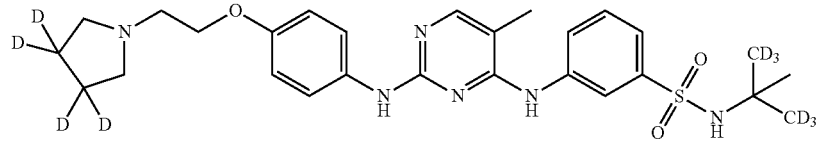
Formula (62)

-continued
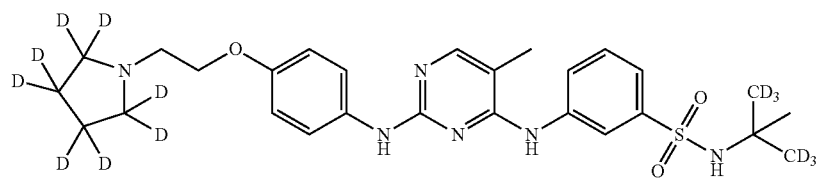
Formula (63)
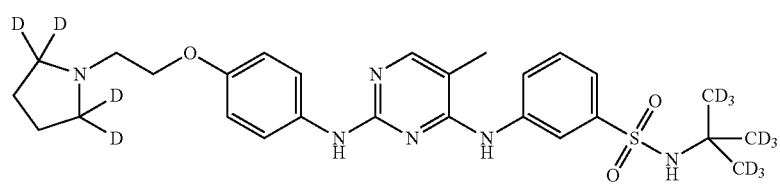
Formula (64)
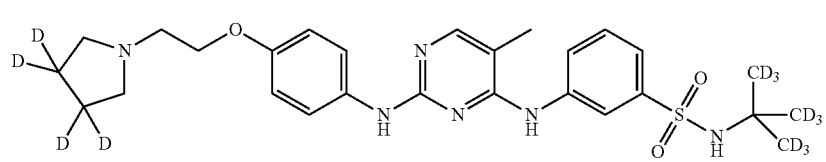
Formula (65)
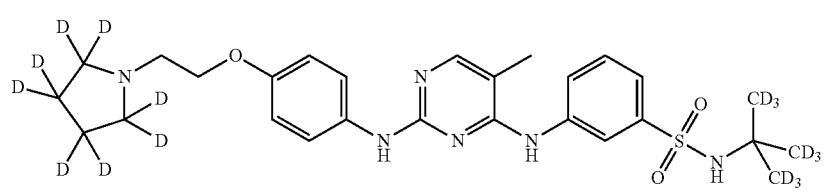
Formula (66)
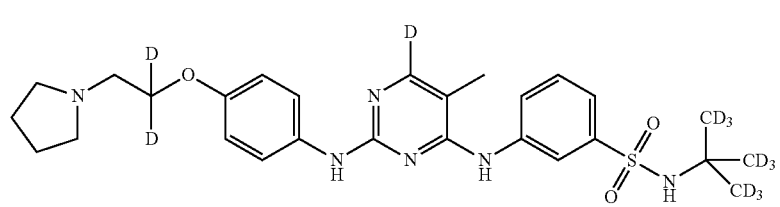
Formula (67)
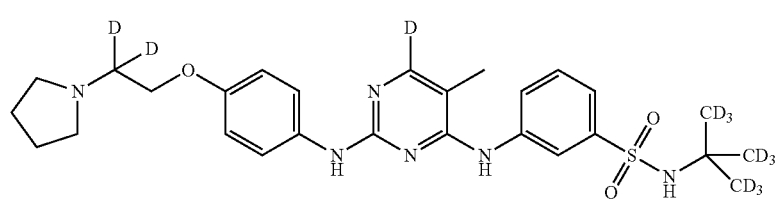
Formula (68)
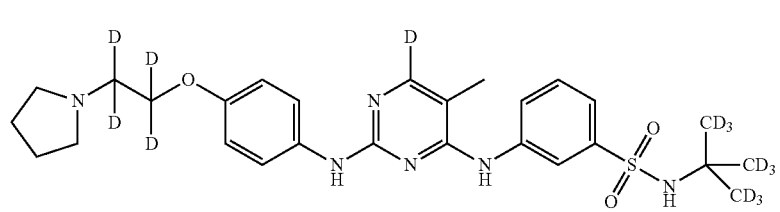
Formula (69)
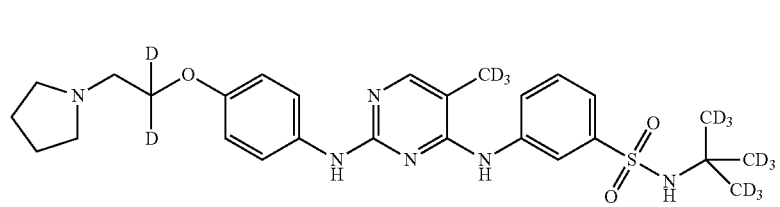
Formula (70)

-continued
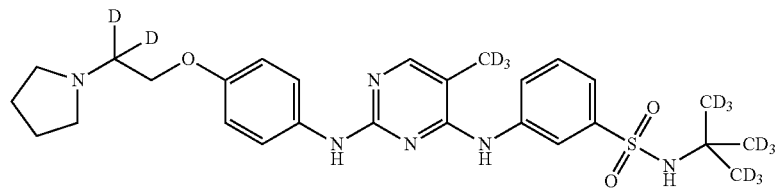
Formula (71)
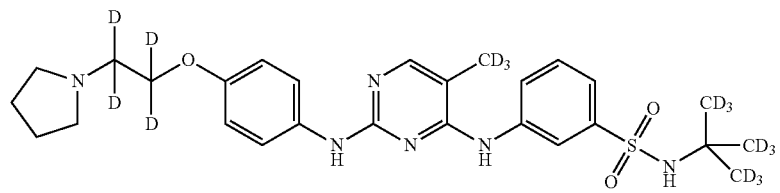
Formula (72)
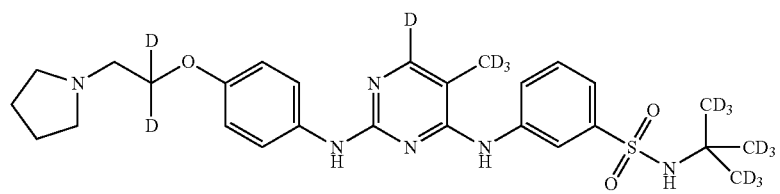
Formula (73)
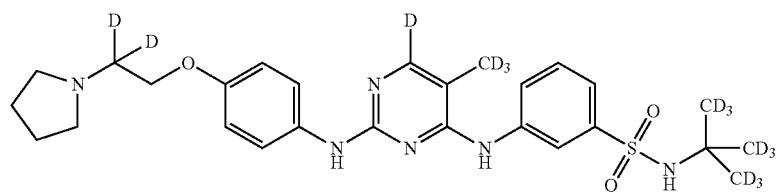
Formula (74)
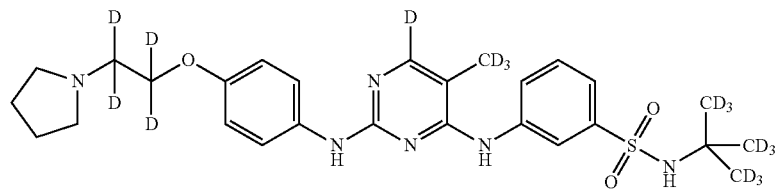
Formula (75)
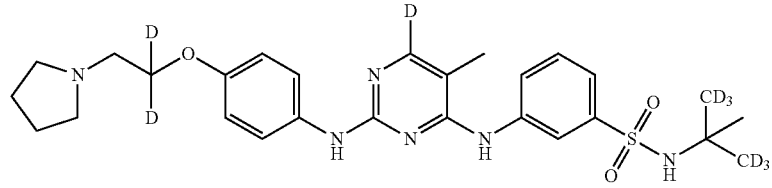
Formula (76)
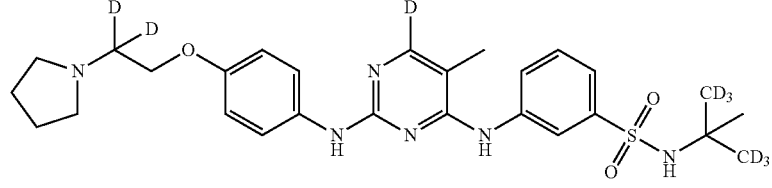
Formula (77)
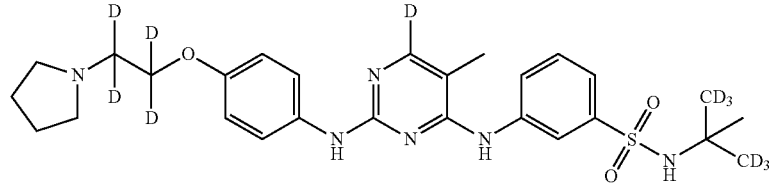
Formula (78)

-continued
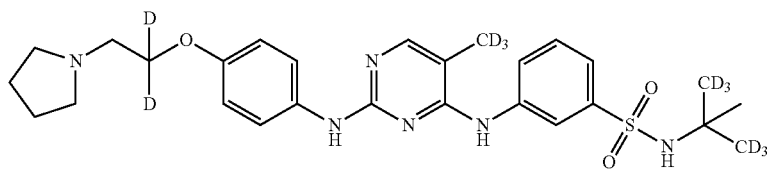
Formula (79)
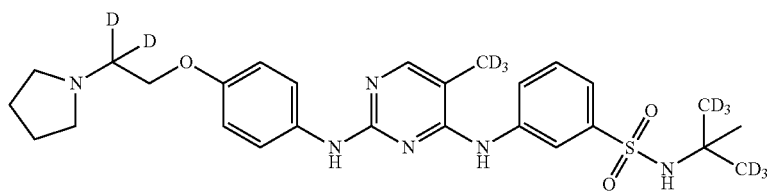
Formula (80)
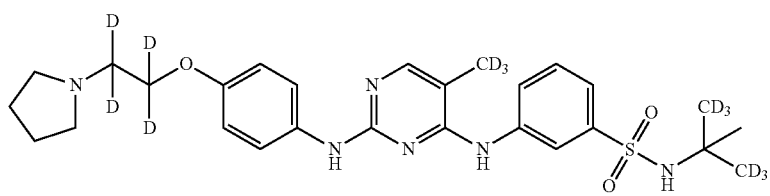
Formula (81)
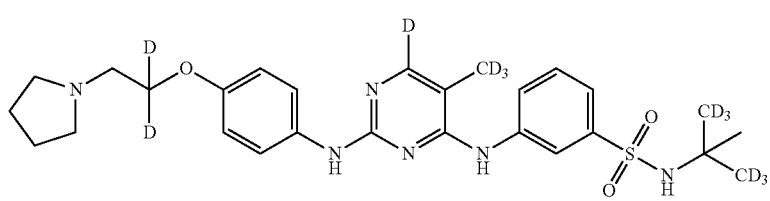
(Formula (82)
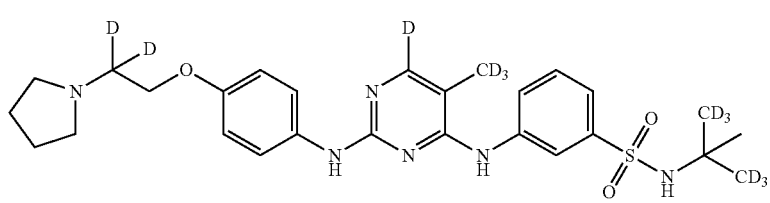
Formula (83)
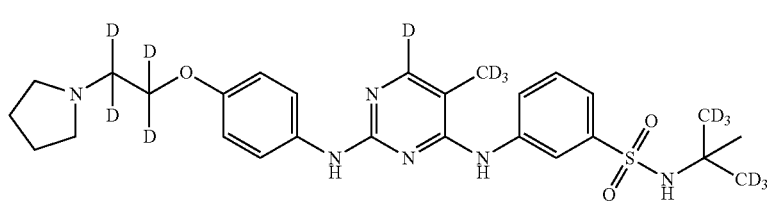
Formula (84)
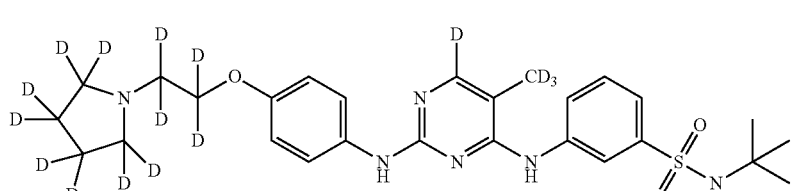
Formula (85)
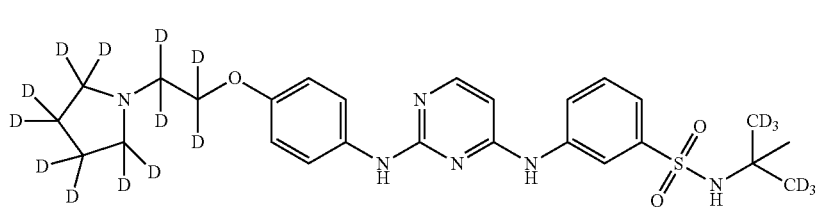
Formula (86)

Formula (87)
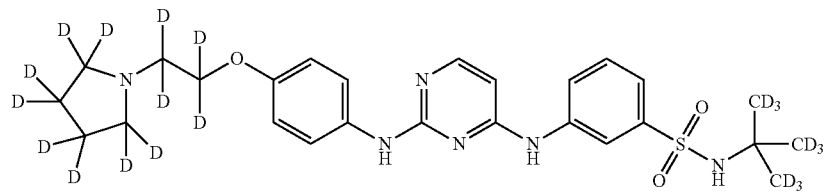
Formula (88)
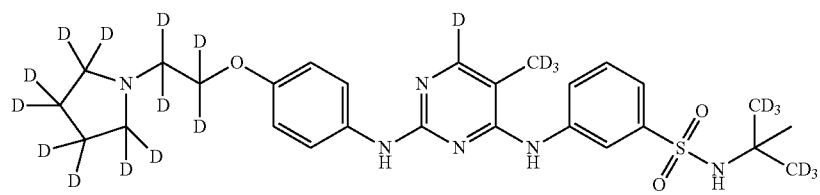
Formula (89)
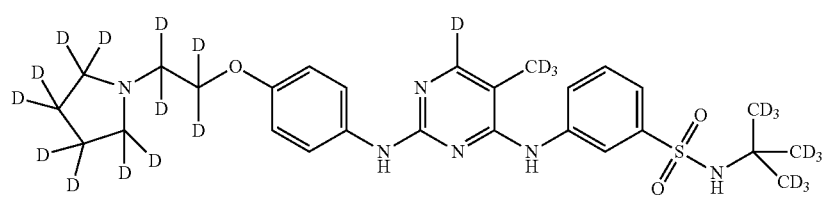
Formula (90)
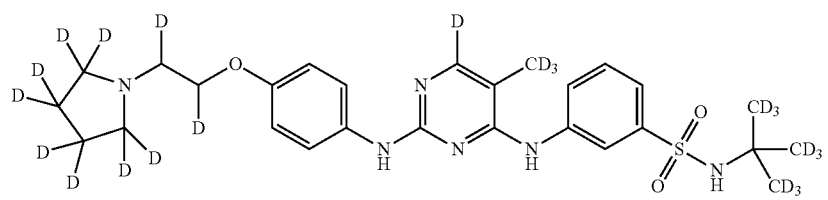
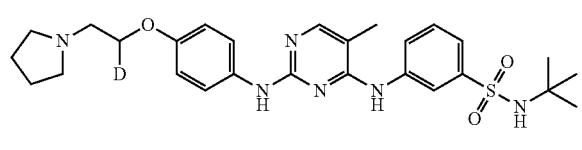
Formula (91)
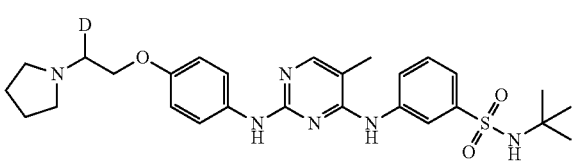
Formula (92)
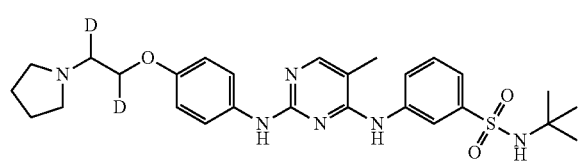
Formula (93)
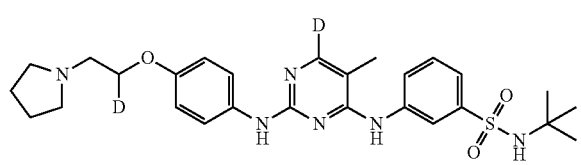
Formula (94)
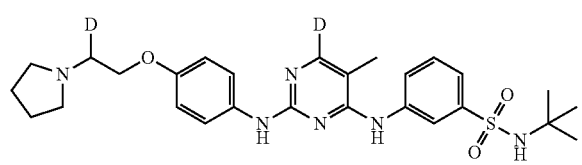
Formula (95)
Formula (96)
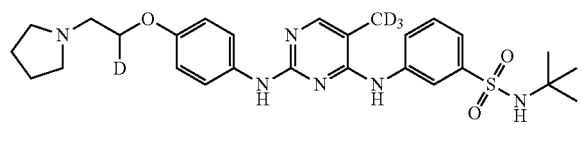
Formula (97)
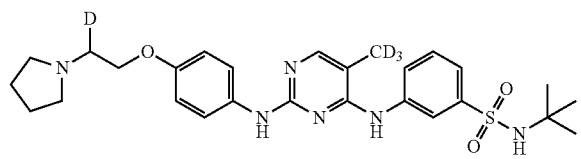
Formula (98)

-continued
Formula (99)
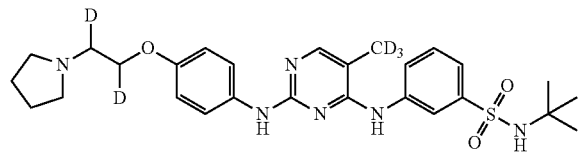
Formula (100)
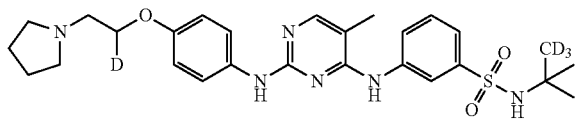
Formula (101)
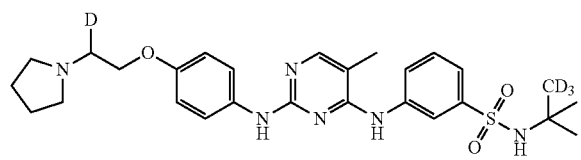
Formula (102)
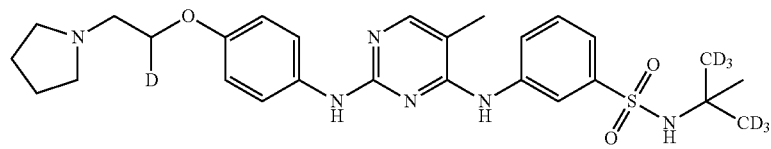
Formula (103)
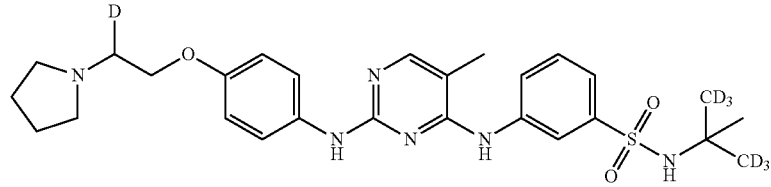
Formula (104)
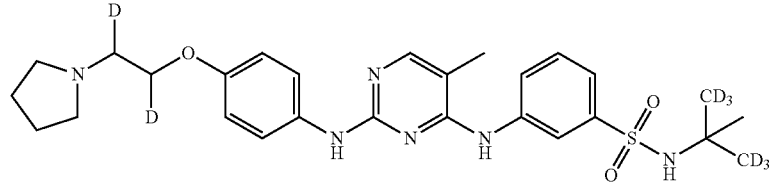
Formula (105)
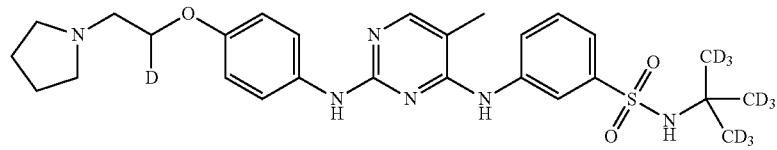
Formula (106)
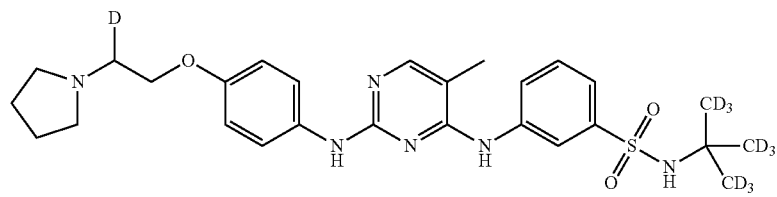
Formula (107)
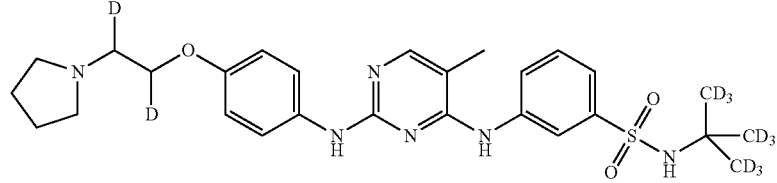
Formula (108)

-continued
Formula (109)
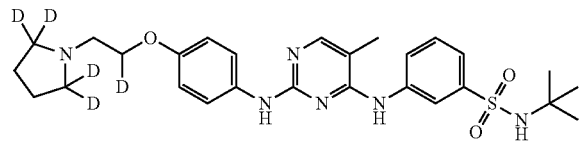
Formula (110)
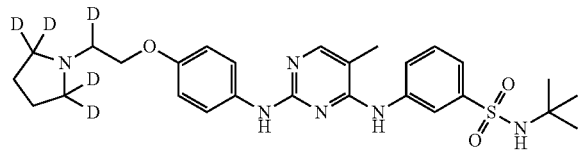
Formula (111)
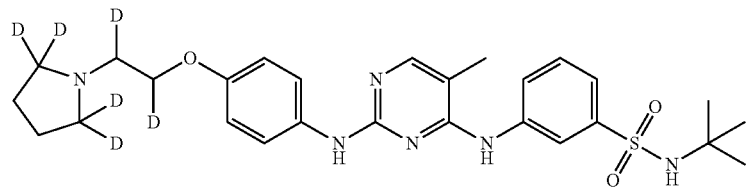
Formula (112)
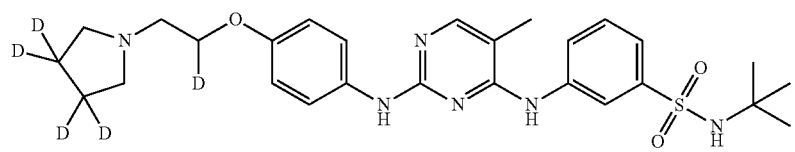
Formula (113)
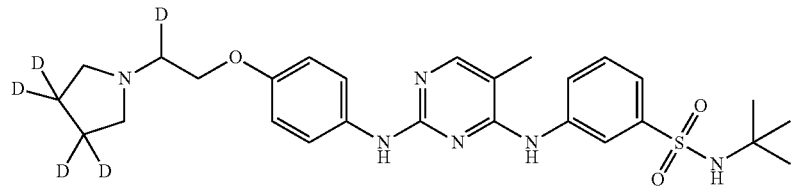
Formula (114)
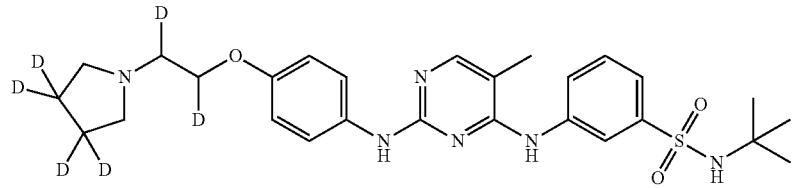
Formula (115)
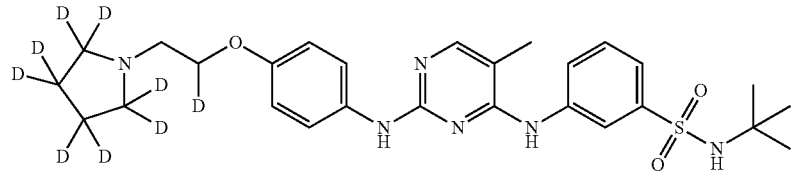
Formula (116)
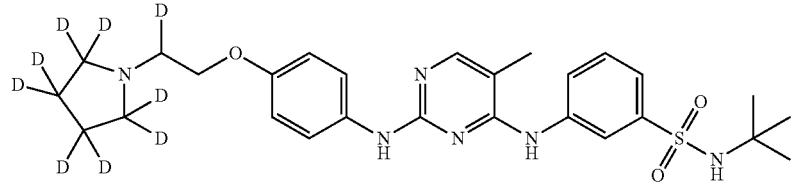

Formula (117)

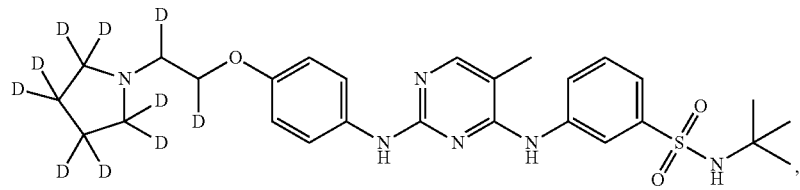

or a pharmaceutically acceptable salt, a prodrug, a hydrate or a solvate, a crystalline form, a N-oxide and various diastereoisomers thereof.

9. The compound of claim 8, which is

T-1

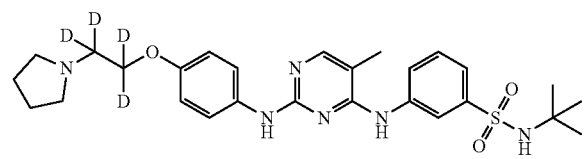

or a pharmaceutically acceptable salt thereof.

10. The compound of claim 8, which is

T-2

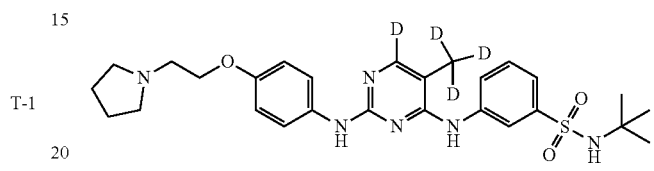

or a pharmaceutically acceptable salt thereof.

11. The compound of claim 8, which is

T-3

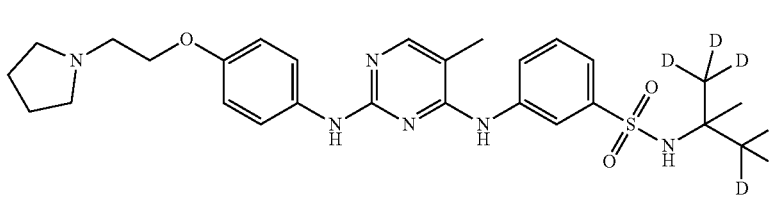

or a pharmaceutically acceptable salt thereof.

12. The compound of claim 8, which is

T-4

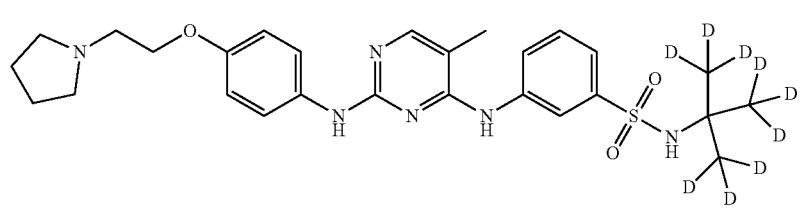

or a pharmaceutically acceptable salt thereof.

13. The compound of claim 8, which is

T-5

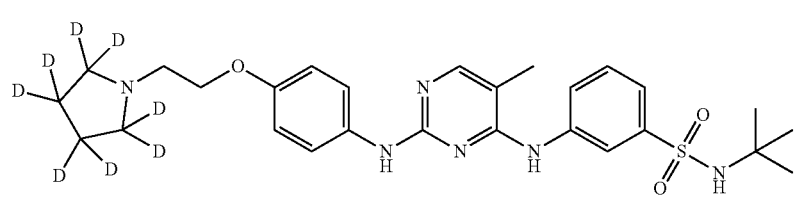

or a pharmaceutically acceptable salt thereof.

14. A pharmaceutical composition, comprising:
pharmaceutically acceptable excipients, and
a compound of claim 1, or a pharmaceutically acceptable salt, a prodrug, a hydrate or a solvate, a crystalline form, a N-oxide and various diastereoisomers thereof.

15. A method of non-prophylactic treatment of a disease in a subject, comprising administering to the subject the compound of claim 1, wherein the disease is selected from a proliferative disorder of bone marrow tissue, polycythemia vera, cancer, and psoriasis.

16. The method of claim 15, wherein the disease is polycythemia vera.

* * * * *